United States Patent
Kai et al.

(10) Patent No.: US 12,312,327 B2
(45) Date of Patent: May 27, 2025

(54) CRYSTAL OF 1,3,5-TRIAZINE DERIVATIVE OR SOLVATE THEREOF AND METHOD FOR PRODUCING SAME

(71) Applicant: Shionogi & Co., Ltd., Osaka (JP)

(72) Inventors: Hiroyuki Kai, Osaka (JP); Yuki Murakami, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 721 days.

(21) Appl. No.: 17/761,498

(22) PCT Filed: Sep. 18, 2020

(86) PCT No.: PCT/JP2020/035378
§ 371 (c)(1),
(2) Date: Mar. 17, 2022

(87) PCT Pub. No.: WO2021/054421
PCT Pub. Date: Mar. 25, 2021

(65) Prior Publication Data
US 2022/0396561 A1 Dec. 15, 2022

(30) Foreign Application Priority Data
Sep. 19, 2019 (JP) .................. 2019-170340
Jul. 17, 2020 (JP) .................. 2020-122749

(51) Int. Cl.
C07D 401/12 (2006.01)

(52) U.S. Cl.
CPC ........ C07D 401/12 (2013.01); *C07B 2200/05* (2013.01); *C07B 2200/13* (2013.01)

(58) Field of Classification Search
CPC .............. C07D 401/12; C07B 2200/05; C07B 2200/13
See application file for complete search history.

(56) References Cited

U.S. PATENT DOCUMENTS

| | | | |
|---|---|---|---|
| 2016/0115151 A1* | 4/2016 | Kai | A61K 31/53 544/212 |
| 2017/0362199 A1 | 12/2017 | Kai | |

FOREIGN PATENT DOCUMENTS

| | | |
|---|---|---|
| CN | 103476770 | 12/2013 |
| EP | 2 399 910 | 12/2011 |
| EP | 2 604 595 | 6/2013 |
| EP | 3 009 432 | 4/2016 |
| EP | 3 862 000 | 8/2021 |
| WO | 02/094767 | 11/2002 |
| WO | 2006/012639 | 2/2006 |
| WO | 2010/092966 | 8/2010 |
| WO | 2010/149578 | 12/2010 |
| WO | 2012/020749 | 2/2012 |
| WO | 2012/121764 | 9/2012 |
| WO | 2013/089212 | 6/2013 |
| WO | 2014/200078 | 12/2014 |
| WO | 2015/027212 | 2/2015 |
| WO | 2017/058645 | 4/2017 |
| WO | 2020/071530 | 4/2020 |

OTHER PUBLICATIONS

Office Action issued Dec. 21, 2023 in corresponding Russian Patent Application No. 2022109980 with English-language translation.
English language translation of Search Report issued Dec. 7, 2023 in corresponding Russian Patent Application No. 2022109980.
Mino R. Caira, "Crystalline Polymorphism of Organic Compounds", Topics in Current Chemistry, vol. 198, pp. 163-208 (1998).
Sherry L. Morissette et al., "High-throughput crystallization: polymorphs, salts, co-crystals and solvates of pharmaceutical solids", Advanced Drug Delivery Reviews, vol. 56, pp. 275-300 (2004).
Fang Tian et al., "Factors affecting crystallization of hydrates", Journal of Pharmacy and Pharmacology, vol. 62, pp. 1534-1546 (2010).
I.G. Smirnova et al., "Clinical pharmacokinetics: theoretical, applied and analytical aspects: a guide", Ed. by V.G. Kukes, Chapter 11.2. Relationship of the Crystal Structure of the Substance, Pharmacokinetics and Effectiveness of the Drug, pp. 235-248 (2009).
Naga K. Duggirala et al., "Pharmaceutical cocrystals: along the path to improved medicines", Chem. Commun., vol. 52, pp. 640-655 (2016).
G.A. Kuznetsova, "Methodological instructions," Irkutsk State University (Seihveisu), Dept. General Physics, p. 3, $2^{nd}$ para. (2005).
J. Bernstein, "Polymorphism of molecular crystals," Moscow, Nauka, Chapter 7.3.2. Bioavailability, pp. 324-330 (2007).

(Continued)

Primary Examiner — Timothy R Rozof
(74) Attorney, Agent, or Firm — Wenderoth, Lind & Ponack, L.L.P.

(57) ABSTRACT

A crystal of a 1,3,5-triazine derivative or a solvate thereof, and a method for producing the same are provided. The present invention relates to a crystal of a compound represented by Formula (I) or a solvate thereof:

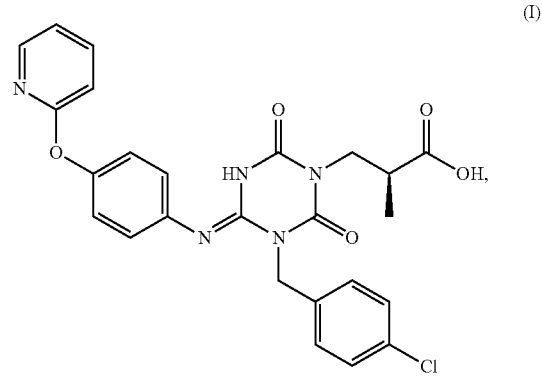

(I)

and relates to a pharmaceutical composition containing the same. The present invention also relates to a crystal of a compound represented by Formula (I), or a solvate thereof.

8 Claims, 13 Drawing Sheets

(56) References Cited

OTHER PUBLICATIONS

Monia Aparecida Lemos Pinto et al., "Thermoanalytical studies of carbamazepine: hydration/dehydration, thermal decomposition, and solid phase transitions", Brazilian Journal of Pharmaceutical Sciences, vol. 50, No. 4, pp. 877-884 (2014).
Klaus Kümmerer, "Pharmaceuticals in the Environment", Annual Review of Environment and Resources, 2010, vol. 35, pp. 57-75 (2010).
Barbara Rodríguez-Spong et al., "General principles of pharmaceutical solid polymorphism: a supramolecular perspective", Advanced Drug Delivery Reviews, vol. 56, pp. 241-274 (2004).
Search Report issued Feb. 5, 2024 in corresponding Taiwanese Patent Application No. 109132334, with English translation.
Sarma B. et al., "Solid forms of pharmaceuticals: Polymorphs, salt and Cocrystals", Korean J. Chem. Eng. (2011), vol. 28, No. 2, pp. 315-322.
Narayan Variankaval et al., "From Form to Function: Crystallization of Active Pharmaceutical Ingredients", AIChE Journal (2008), vol. 54, No. 7, pp. 1682-1688.
Jaakko Aaltonen et al., "Solid form screening—A review", European Journal of Pharmaceutics and Biopharmaceutics (2009), vol. 71, No. 1, pp. 23-37.
Stephen Byrn et al., "Pharmaceutical Solids: A Strategic Approach to Regulatory Considerations", Pharmaceutical Research (1995), vol. 12, No. 7, pp. 945-954.
Notification of Transmittal of Translation of International Preliminary Report on Patentability and Written Opinion of the International Searching Authority mailed Mar. 31, 2022 in International (PCT) Application No. PCT/JP2020/035378.
Stork et al., "Preparation of Ethyl β-Benzylaminopropionate and Benzyl-di-(β-carbethoxyethyl)-amine", Journal of American Chemical Society, 1947, vol. 69, No. 4, pp. 971-972.
Mallesha et al., "A Simple and Convenient Protocol for the Selective Mono Debenzylation of Dibenzylamines Using 10% Pd/C and HCOONH$_4$", International Journal of Chemistry Research, 2011, Vo. 2, Issue 4, pp. 26-28.
International Search Report dated Nov. 10, 2020 in International (PCT) Application No. PCT/JP2020/035378.
Kennedy, C., "P2X Receptors: Targets for Novel Analgesics?", The Neuroscientist, 2005, vol. 11, No. 4, pp. 345-356.
Cockayne, D.A., et al., "P2X2 knockout mice and P2X2/P2X3 double knockout mice reveal a role for the P2X2 receptor subunit in mediating multiple sensory effects of ATP", J. Physiol., vol. 567, No. 2, 2005, pp. 621-639.
Shieh, C., et al., "P2X receptor ligands and pain", Expert Opinion on Therapeutic Patents, 2006, vol. 16, No. 8, pp. 1113-1127.
North, R.A., "P2X3 receptors and peripheral pain mechanisms", J. Physiol, 2003, vol. 554, No. 2, pp. 301-308.
Kennedy, C., et al., "Crossing the pain barrier: P2 receptors as targets for novel analgesics", J. Physiol, 2003, vol. 553, No. 3, pp. 683-694.
Gever, J.R., et al., "Pharmacology of P2X channels", Pflungers Arch—Eur J Physiol 2006, vol. 452, pp. 513-537.
Jarvis, M.F., et al., "A-317491, a novel potent and selective non-nucleotide antagonist of P2X3 and P2X2/3 receptors, reduces chronic inflammatory and neuropathic pain in the rat", PNAS, 2002, vol. 99, No. 26, pp. 17179-17184.
Brouns, I., et al., "Intraepithelial Vagal Sensory Nerve Terminals in Rat Pulmonary Neuroepithelial Bodies Express P2X3 Receptors", Am. J. Respir. Cell Mol. Biol., 2000, vol. 23, pp. 52-61.
Basoglu, O.K., et al., "Effects of Aerosolized Adenosine 5'-Triphosphate vs Adenosine 5'-Monophosphate on Dyspnea and Airway Caliber in Healthy Nonsmokers and Patients With Asthma", Chest, 2005, vol. 128, No. 4, pp. 1905-1909.
Adriaensen, D., et al., "Functional Morphology of Pulmonary Neuroepithelial Bodies: Extremely Complex Airway Receptors", The Anatomical Record Part A, 2003, vol. 270A, pp. 25-40.
Abdulqawi, R., et al., "P2X3 receptor antagonist (AF-219) in refractory chronic cough: a randomized, double-blind, placebo-controlled phase 2 study", Lancet, 2015, vol. 385, pp. 1198-1205.
Pijacka, W., et al., "Purinergic receptors in the carotid body as a new drug target for controlling hypertension", Nature Medicine, 2016, vol. 22, No. 10, pp. 1151-1159.
Wang, S., et al., "Adrenergic signaling mediates mechanical hyperalgesia through activation of P2X3 receptors in primary sensory neurons of rats with chronic pancreatitis", Am J Physiol Gastrointest Liver Physiol, 2015, vol. 308, pp. G710-G719.
Ding, S., et al., "P2X3 receptor involvement in endometriosis pain via ERK signaling pathway", PLOS ONE, 2017, vol. 12, No. 9, pp. 1-17.
Yuan, M., et al., "Effect of A-317491 delivered by glycolipid-like polymer micelles on endometriosis pain", International Journal of Nanomedicine, 2017, vol. 12, pp. 8171-8183.
Shustov, G.V., et al., "3-Methylazetidin-2-one and Its Precursors: Optical Resolution and Absolute Configurations", Tetrahedron: Asymmetry, 1996, vol. 7, No. 3, pp. 699-708.
Hirayama, N., "Handbook for preparing crystals of organic compound", 2008, vol. 4, pp. 1-28.
Takata, N., "Api form screening and selection in drug discovery stage", Pharm Stage, 2007, vol. 6, No. 10, pp. 20-27.
Office Action issued Sep. 3, 2024, in corresponding Brazilian Patent Application No. BR112022004398-8 with partial English-language translation.
Hirayama Noriaki, "Handbook of organic compounds crystallization—principles and know-how", 2008, pp. 57-84, ISBN 978-4-621-07991-1, XP008183996 [Y] 1-9 4. 1-4. 2.

\* cited by examiner

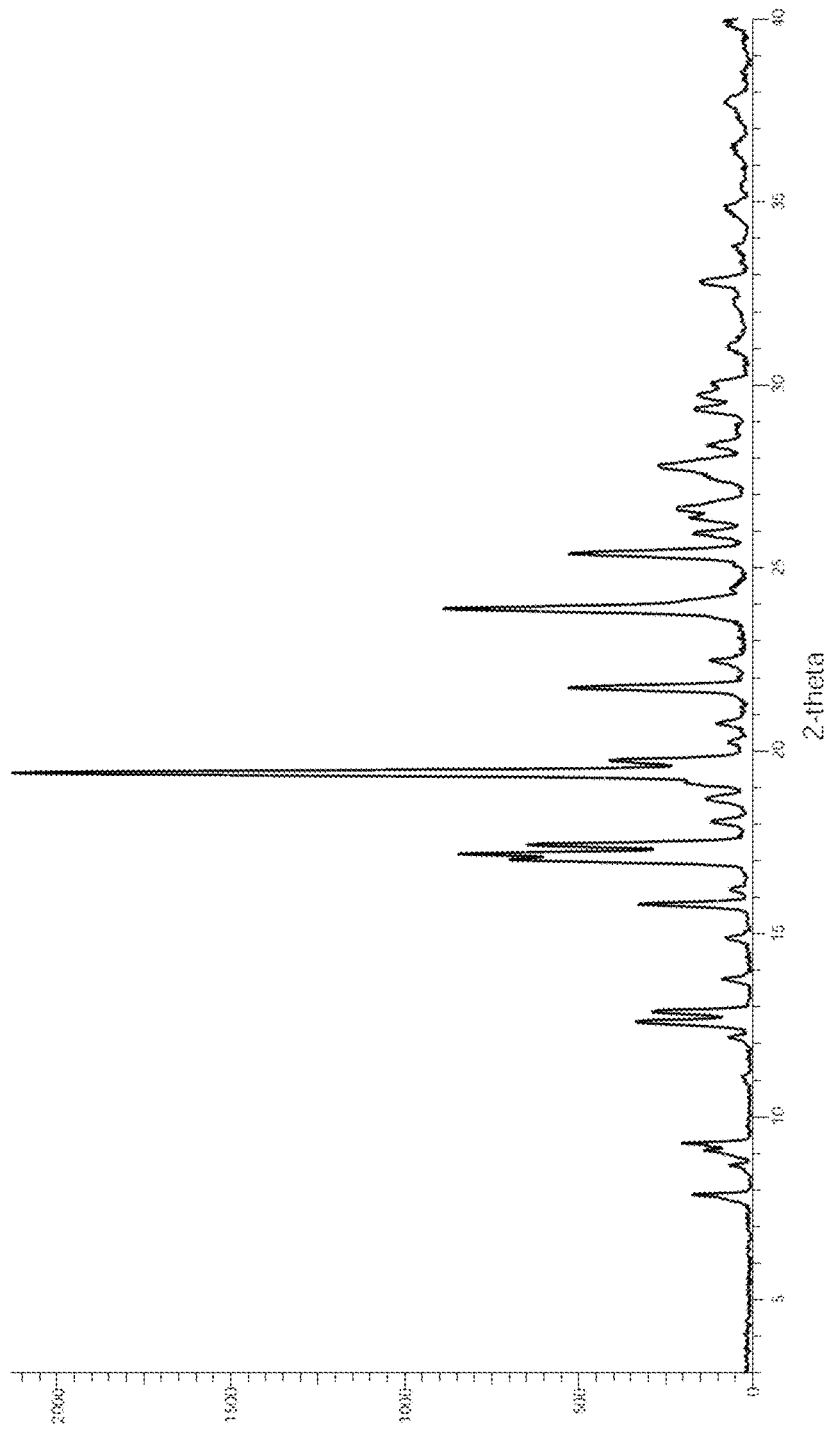
[Figure 1]

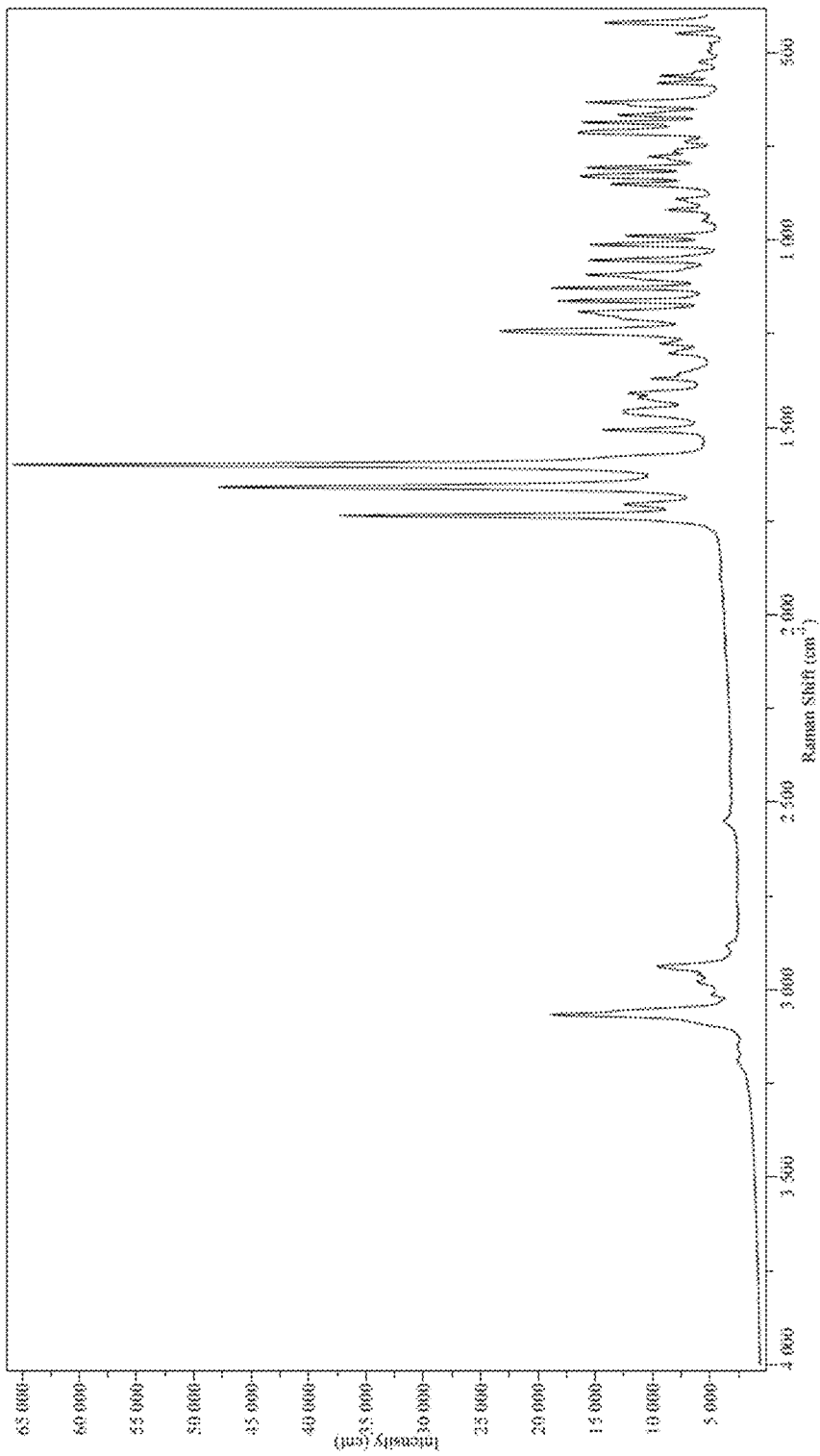
[Figure 2]

[Figure 3]
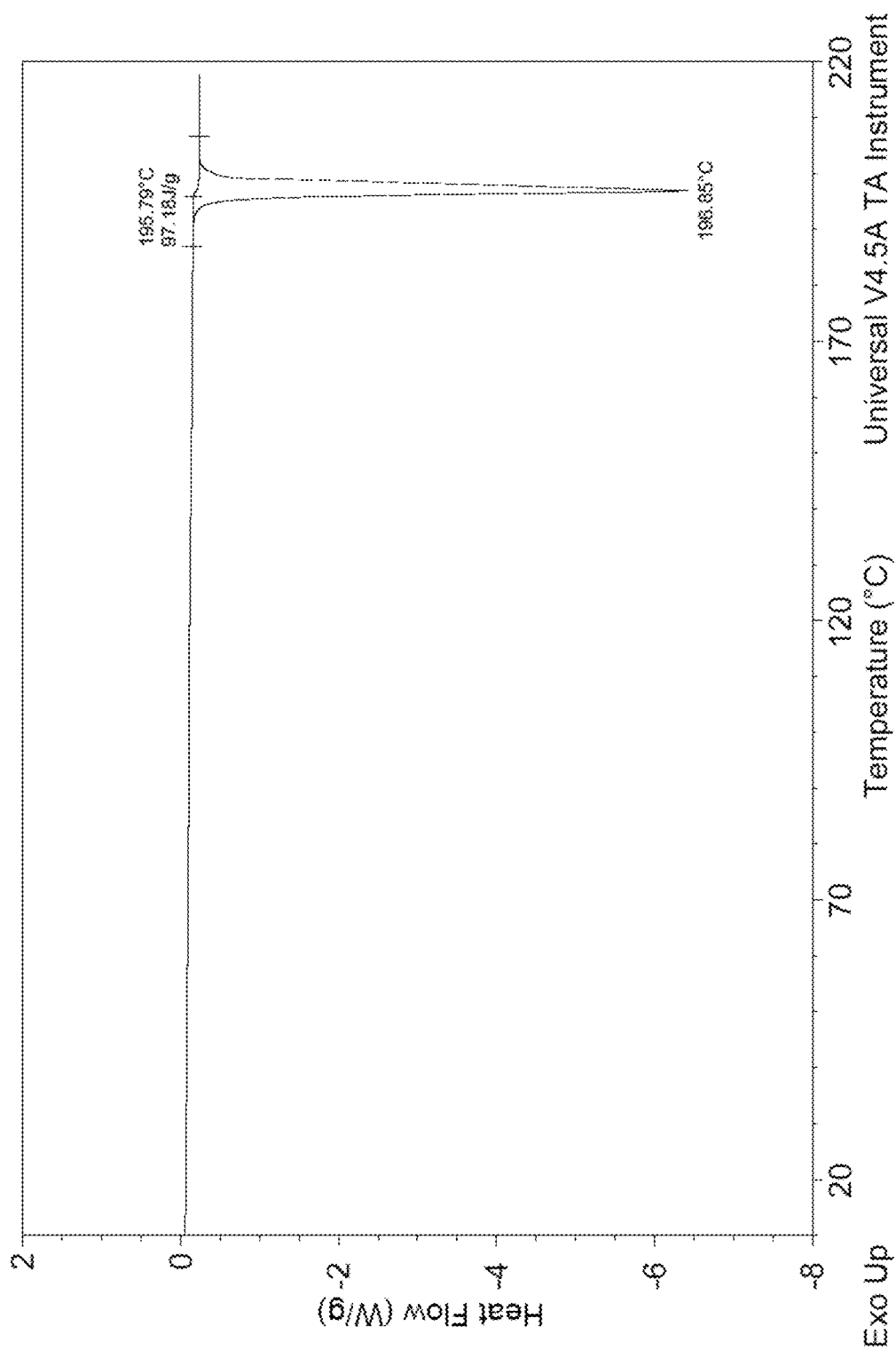

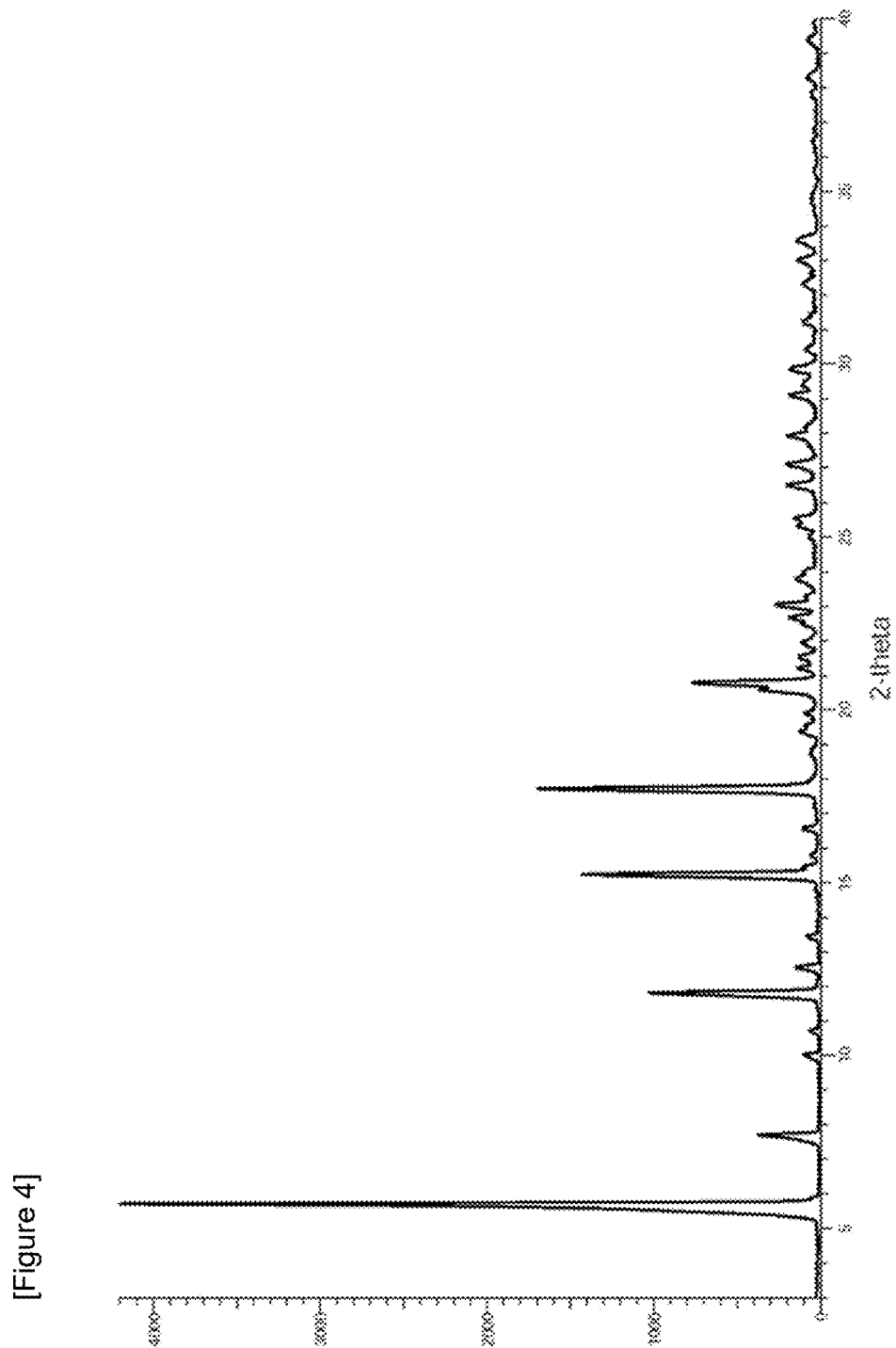
[Figure 4]

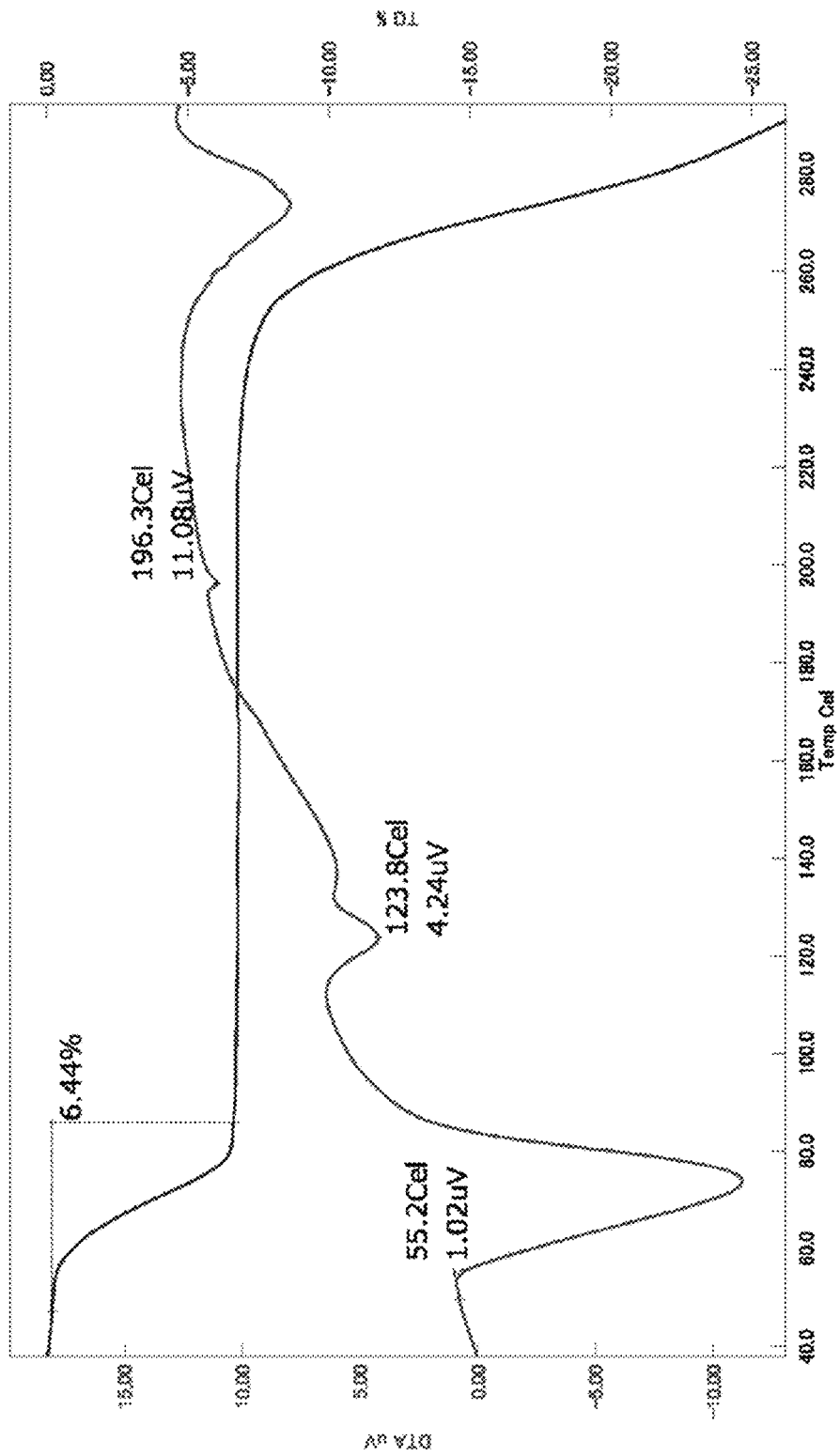
[Figure 5]

[Figure 6]
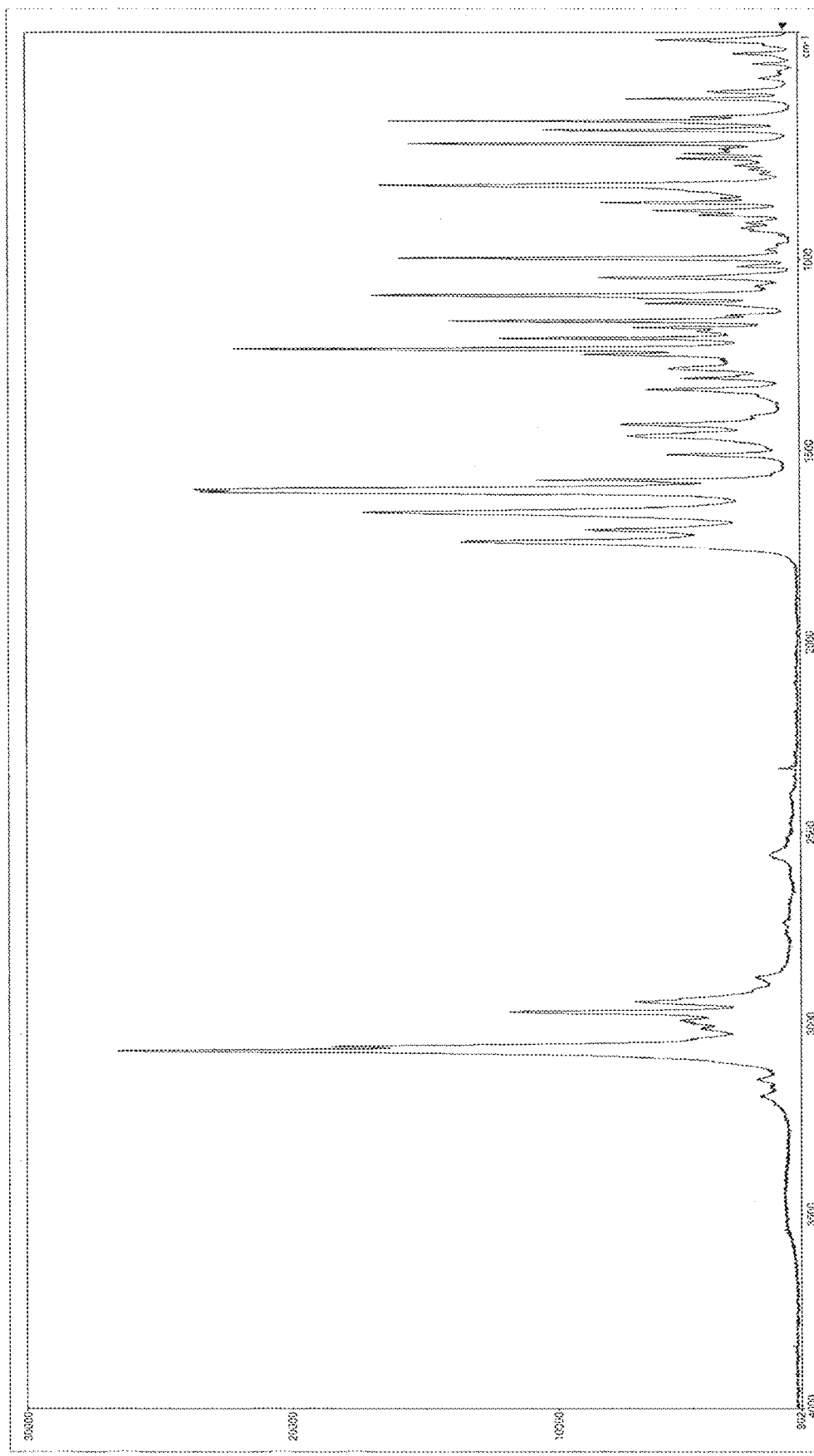

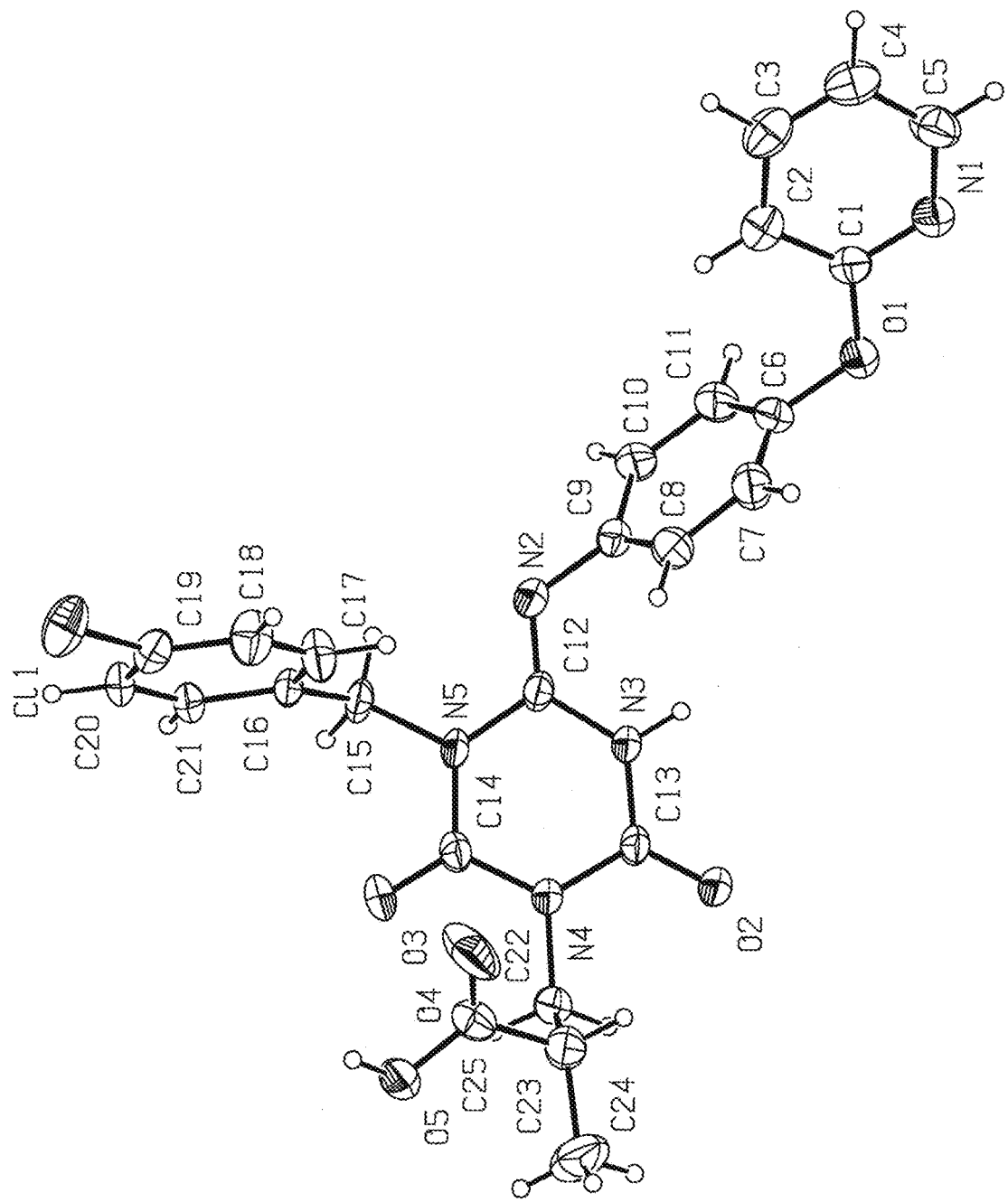
[Figure 7]

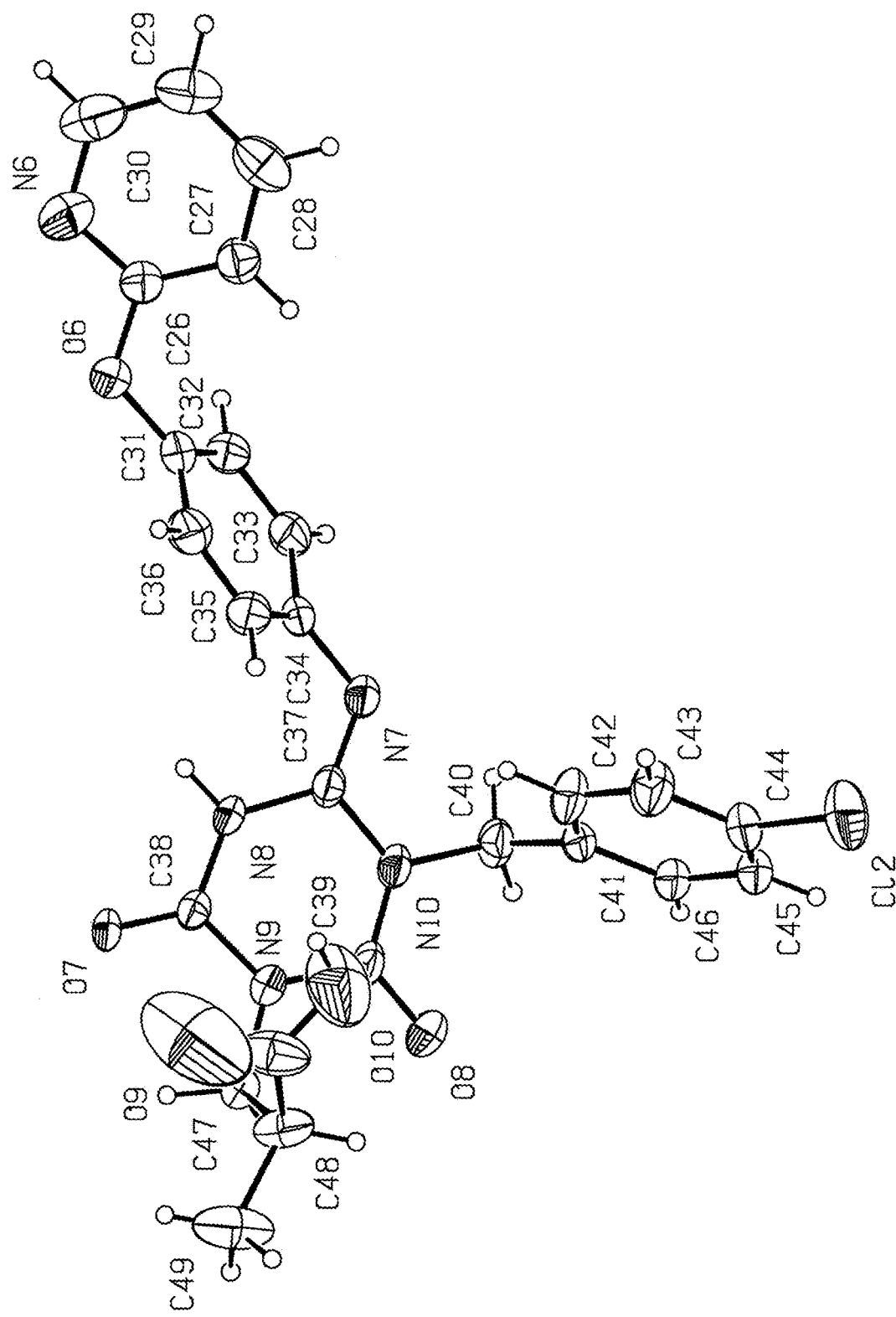
[Figure 8]

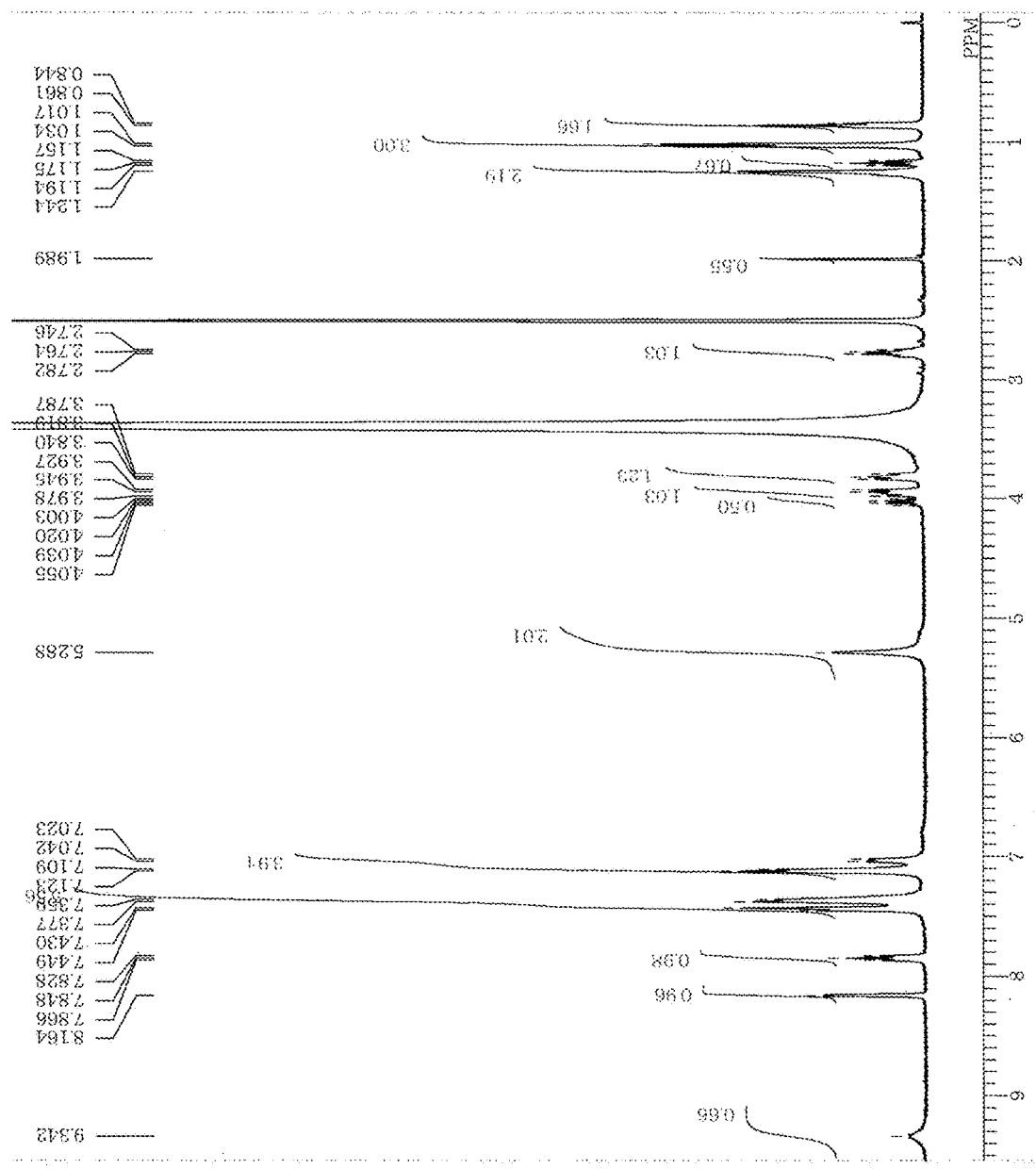
[Figure 9]

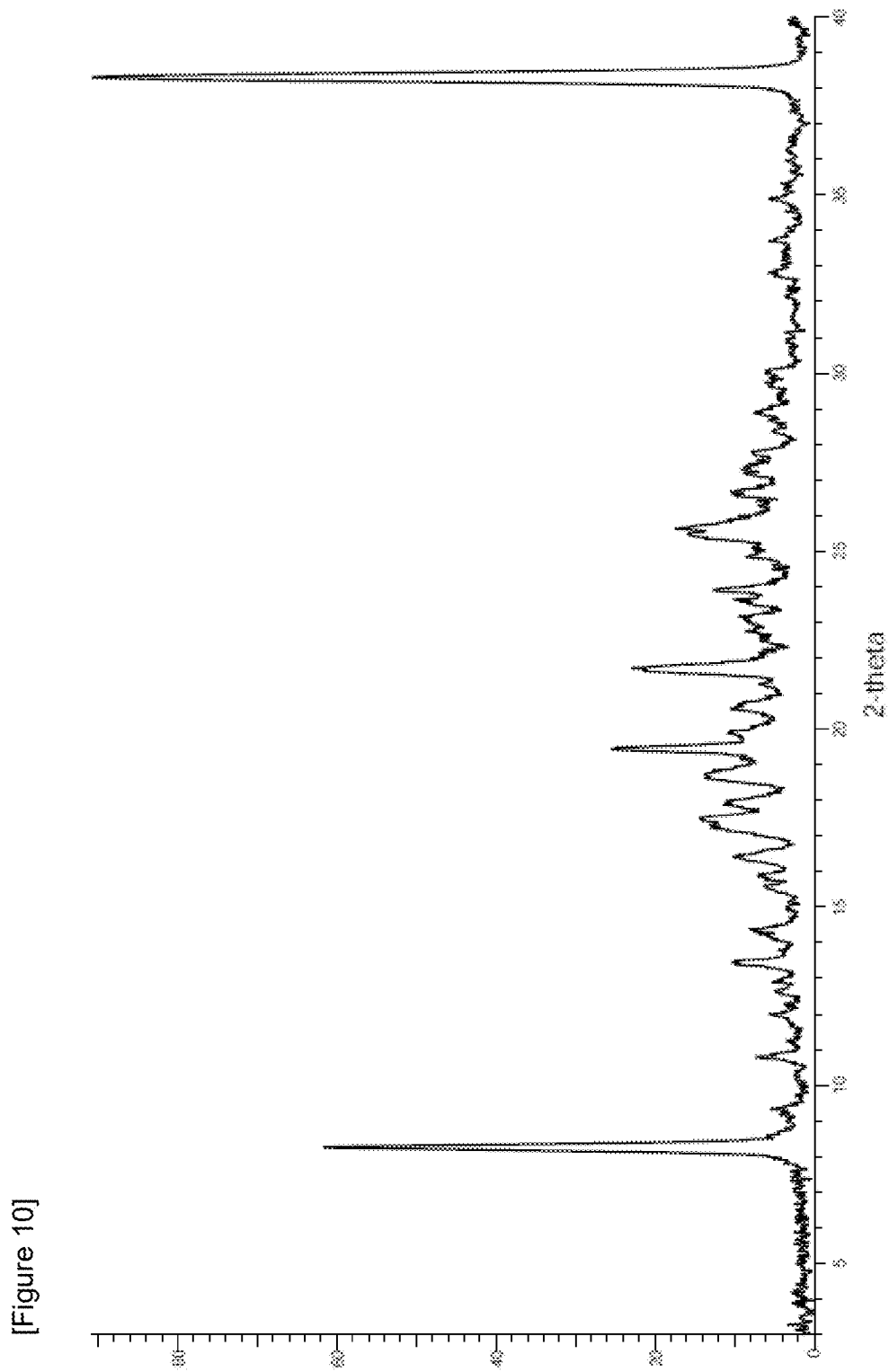
[Figure 10]

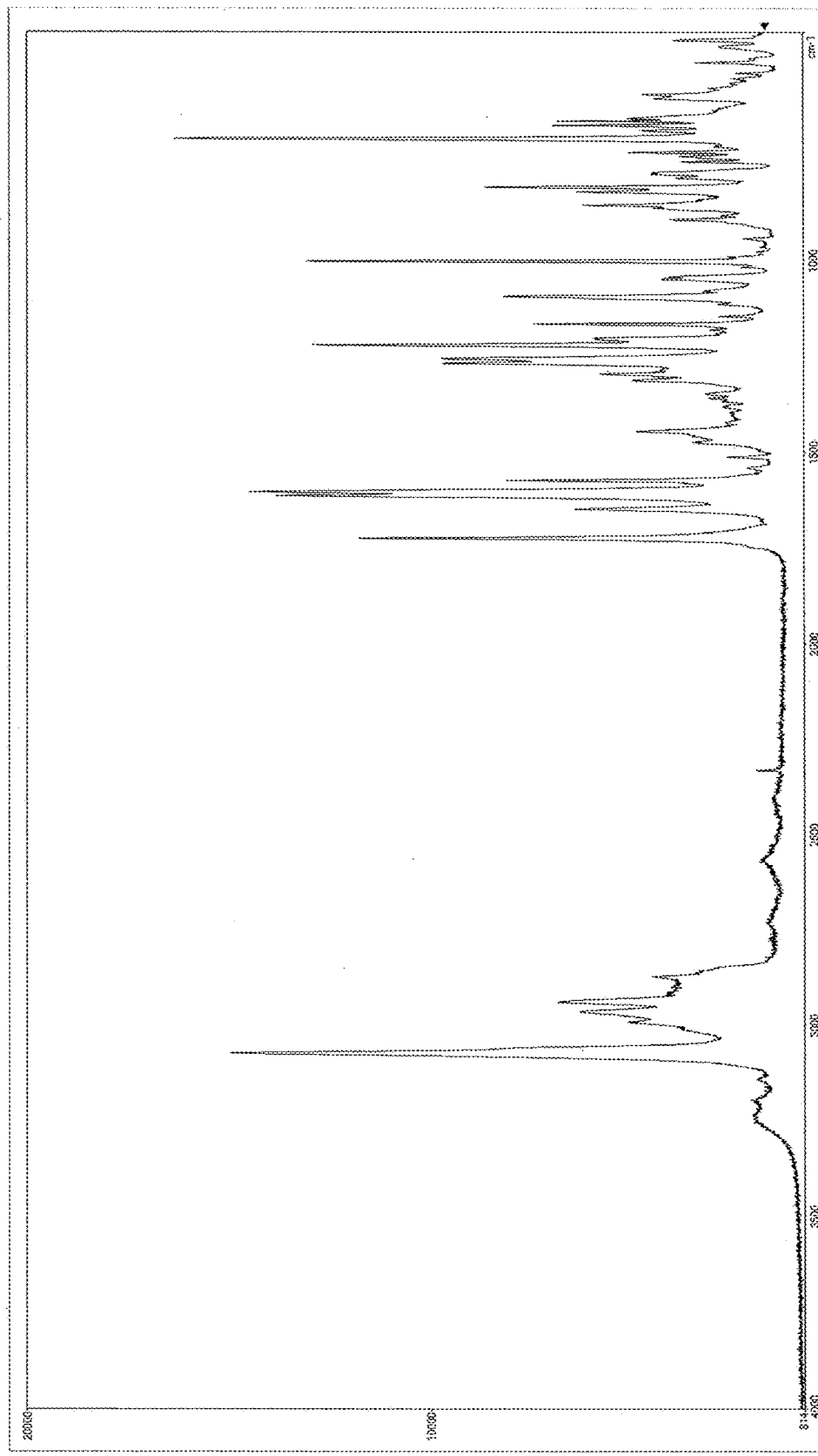
[Figure 11]

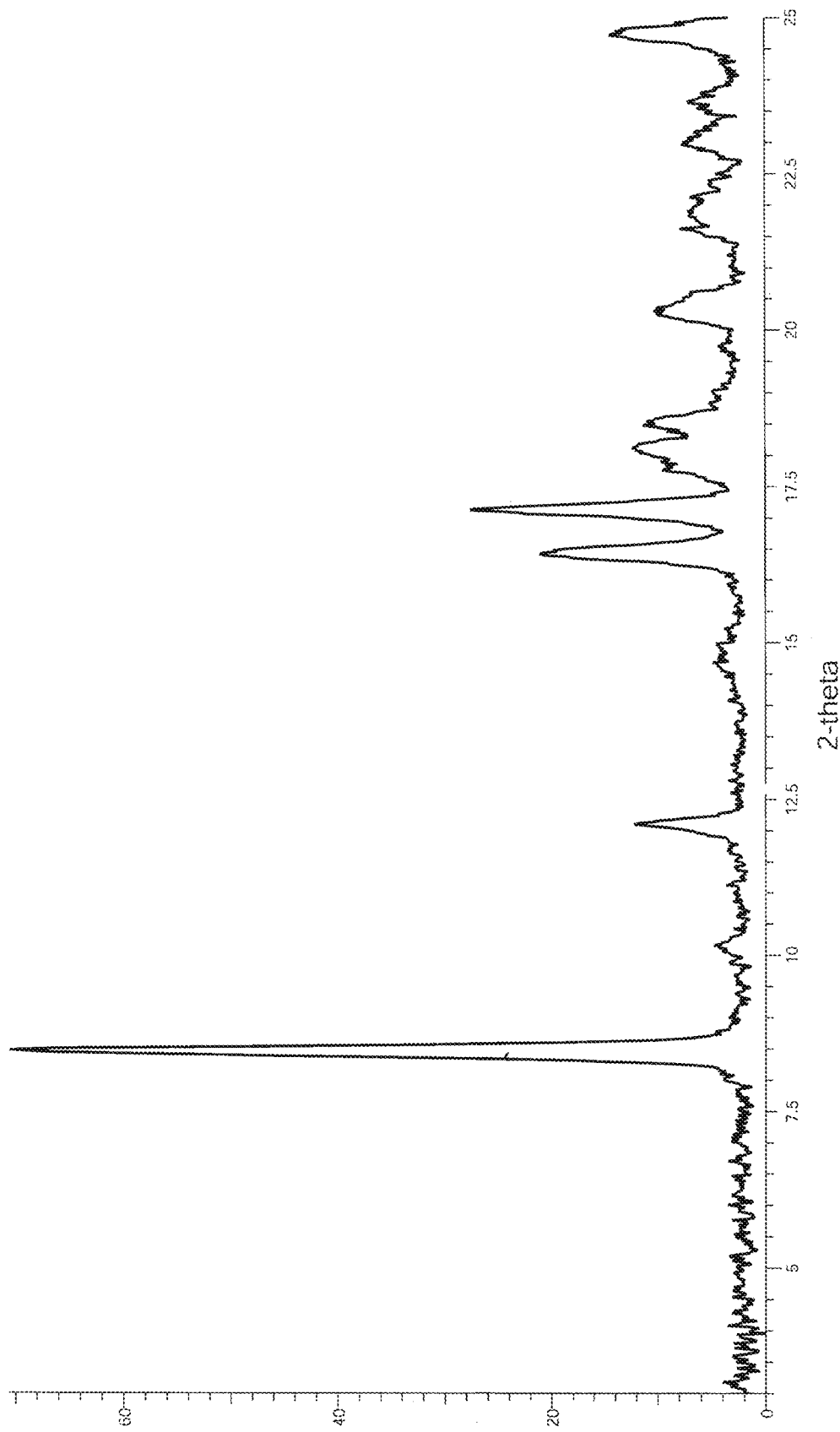
[Figure 12]

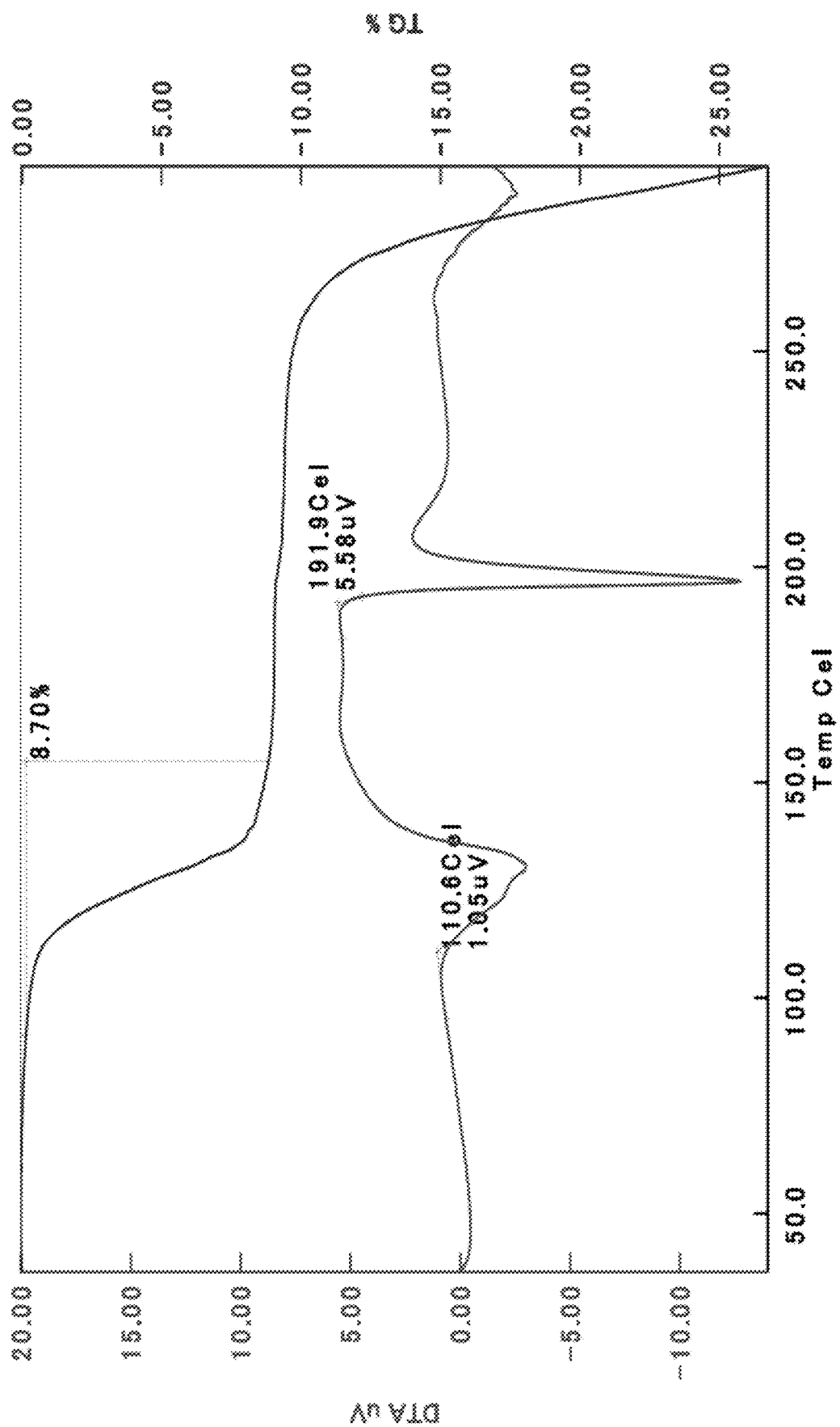
[Figure 13]

CRYSTAL OF 1,3,5-TRIAZINE DERIVATIVE OR SOLVATE THEREOF AND METHOD FOR PRODUCING SAME

TECHNICAL FIELD

The present invention relates to a crystal of a 1,3,5-triazine derivative or a solvate thereof and a pharmaceutical composition containing the same. The present invention relates to a method for producing a crystal of a 1,3,5-triazine derivative or a solvate thereof and a pharmaceutical composition containing the same.

BACKGROUND ART

Adenosine triphosphate (ATP) is known as an intracellular energy source and a phosphorylated substrate. On the other hand, it is also known to act as an extracellular information transmitter. Furthermore, it is known that ATP is released to the outside of cells by various stimuli such as cell damage, inflammation, noxious stimuli, and reduction in blood oxygen level, and that ATP is released to the outside of cells from primary sensory nerve endings together with other neurotransmitters. ATP released to the outside of cells performs various kinds of extracellular information transmission via an ATP receptor (Non-Patent Document 4, Non-Patent Document 5).

ATP receptors are roughly classified in the ion channel P2X family and the G protein coupled P2Y family. The P2X receptor family is reported to have seven subtypes, which form a homotrimer or a heterotrimer with other P2X subtypes to function as a non-selective cation channel (Non-Patent Document 6).

ATP is already known to cause pain, and studies using $P2X_3$ knockout and knockdown techniques have shown that the $P2X_3$ receptor is involved in the transmission of chronic pain. The $P2X_3$ receptor is expressed specifically in peripheral sensory nerves, forming a homo-complex or a hetero-complex with $P2X_2$ ($P2X_{2/3}$). (Non-Patent Document 1)

Subsequently, the compound having $P2X_3$ or $P2X_{2/3}$ receptor antagonistic action is suggested to be useful in: pain treatment (Patent Document 1, Non-Patent Document 3, and Non-Patent Document 7); treatment of diseases associated with dysfunctional voiding (Non-Patent Document 2); treatment of respiratory diseases (Non-Patent Document 8, Non-Patent Document 9, Non-Patent Document 10, Patent Document 2, and Patent Document 3); treatment of chronic cough (Patent Document 4, Patent Document 5, and Non-Patent Document 11); treatment of hypertension (Non-Patent Document 12); Treatment of pain associated with pancreatitis (Non-Patent Document 13); and treatment of pain associated with endometriosis (Non-Patent Document 14, and Non-Patent Document 15).

Next, Patent Document 6 describes that a 1,3,5-triazine derivative represented by the following formula has $P2X_3$ and/or $P2X_{2/3}$ antagonistic action, and is useful for treatment and/or prevention of pain:

[Chemical formula 1]

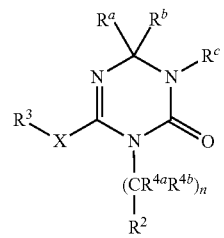

Patent Document 7 describes that a 1,3,5-triazine derivative represented by the following formula has $P2X_3$ and/or $P2X_{2/3}$ antagonistic action, and is useful for treatment and/or prevention of pain:

[Chemical formula 2]

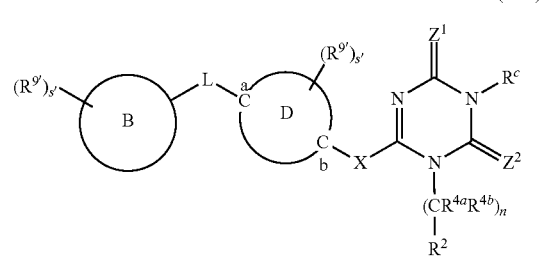

Patent Document 8 describes that a 1,3,5-triazine derivative represented by the following formula has $P2X_3$ and/or $P2X_{2/3}$ antagonistic action, and is useful for treatment and/or prevention of pain:

[Chemical formula 1]

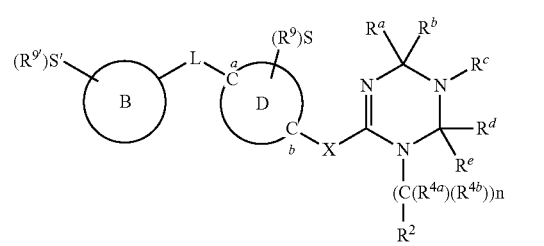

Patent Document 9 describes that a 1,3,5-triazine derivative represented by the following formula has $P2X_3$ and/or $P2X_{2/3}$ antagonistic action, and is useful for treatment and/or prevention of pain:

[Chemical formula 4]

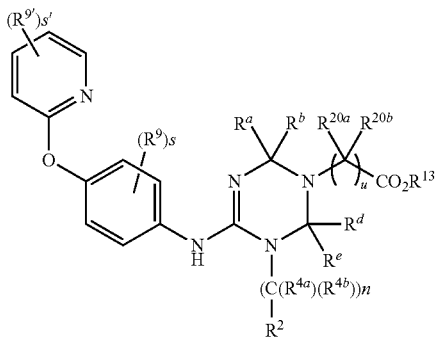

In Examples of Patent Document 9, the following compound (I-127) is disclosed, but a crystal of the compound is not disclosed.

[Chemical formula 5]

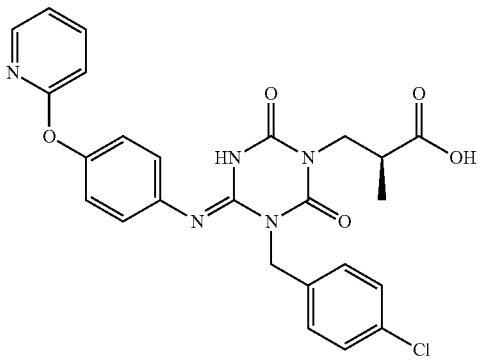

Furthermore, Patent Documents 6, 7, 8, and 9 disclose a method for producing a 1,3,5-triazine derivative, but do not describe the process according to the present invention, and disclose only a method for producing a similar compound. In addition, Patent Document 10 discloses a 1,3,5-triazine derivative exhibiting a therapeutic effect on chronic cough, but does not describe a crystal and a process according to the present invention.

In addition, Non-Patent Document 16 discloses an aza-Michael addition reaction of (S)-1-phenylethylamine and methyl methacrylate.

PRIOR ART REFERENCES

Patent Document

[Patent Document 1] International Publication WO 02/094767 A
[Patent Document 2] International Publication WO 2006/012639 A
[Patent Document 3] International Publication WO 2010/149578 A
[Patent Document 4] International Publication WO 2015/027212 A
[Patent Document 5] International Publication WO 2017/058645 A
[Patent Document 6] International Publication WO 2010/092966A
[Patent Document 7] International Publication WO 2012/020749 A
[Patent Document 8] International Publication WO 2013/089212 A
[Patent Document 9] International Publication WO 2014/200078A
[Patent Document 10] International Publication WO 2020/071530 A Non-Patent Document

[Non-Patent Document 1] Neuroscientist 2005, Vol. 11, pp. 345-356
[Non-Patent Document 2] J. Physiol. 567.2 2005 pp. 621-639
[Non-Patent Document 3] Expert Opin. Ther. Patens 2006 Vol. 16, No. 8, pp. 1113-1127
[Non-Patent Document 4] J. Physiol. 554.2 2003 pp. 301-308
[Non-Patent Document 5] J. Physiol. 553.3 2003 pp. 683-694
[Non-Patent Document 6] Pflungers Arch Eur J physiol 2006, pp. 452, 513-537
[Non-Patent Document 7] PNAS 2002, Vol. 99, No. 26, pp. 17179-17184
[Non-Patent Document 8] Brouns et al. Am J Respir Cell Mol Biol 2000, Vol. 23, pp. 52-61
[Non-Patent Document 9] Basoglu et al. Chest. 2005, Vol. 128, No. 4, pp. 1905-9
[Non-Patent Document 10] Adriaensen et al. THE ANATOMICAL RECORD PART A 2003, Vol. 270A, pp. 25-40
[Non-Patent Document 11] Lancet, 2015, Vol. 385, pp. 1198-205
[Non-Patent Document 12] Nat Med 2016, Vol. 22, pp. 1151-1159
[Non-Patent Document 13] Am J Physiol Gastrointest Liver Physiol 2015, Vol. 308, pp 710-719
[Non-Patent Document 14] PLoS ONE 2017, Vol. 12, No. 9
[Non-Patent Document 15] International Journal of Nanomedicine 2017, Volume 12, 8171-8183
[Non-Patent Document 16] Tetrahedron Asymmetry, Vol. 7, No. 3, pp. 699-708, 1996

SUMMARY OF THE INVENTION

Problems to be Solved by the Invention

The pharmaceutically active ingredients may have substantially different physical properties depending on the respective solid form. Such differences in physical properties may affect, for example, the method of making or administering a pharmaceutically active ingredient, or a pharmaceutical composition comprising the pharmaceutically active ingredient. The present invention relates to crystal of a 1,3,5-triazine derivative or a solvate thereof that is very useful as compared to other solid forms in a method for producing or administering a pharmaceutically active ingredient, or in a pharmaceutical composition comprising a pharmaceutically active ingredient.

In general, physical properties of a crystal of a compound useful as a pharmaceutical have a great influence on bioavailability of drugs, purity of drug substances, formulation of preparations, and the like, and thus are extremely important in development of pharmaceutical products. Therefore, with regard to the compound represented by Formula (I), it is necessary to study which crystalline form is most excellent as a pharmaceutical product. That is, since their physical properties depend on the attributes of individual compounds, it is generally difficult to predict a crystal form of a drug substance having good physical properties, and it is required to actually variously examine each compound.

Therefore, an object of the present invention is to provide a crystalline form having good physical properties as a drug substance for the compound represented by Formula (I).

In addition, Patent Document 9 does not describe a method for producing the compound I-127, but as a similar compound, Reference Example 3 of Patent Document 9 discloses a method for producing a 1,3,5-triazine derivative as shown in the following formula. However, the process is not yet sufficient, and can be improved further.

[Chemical formula 6]

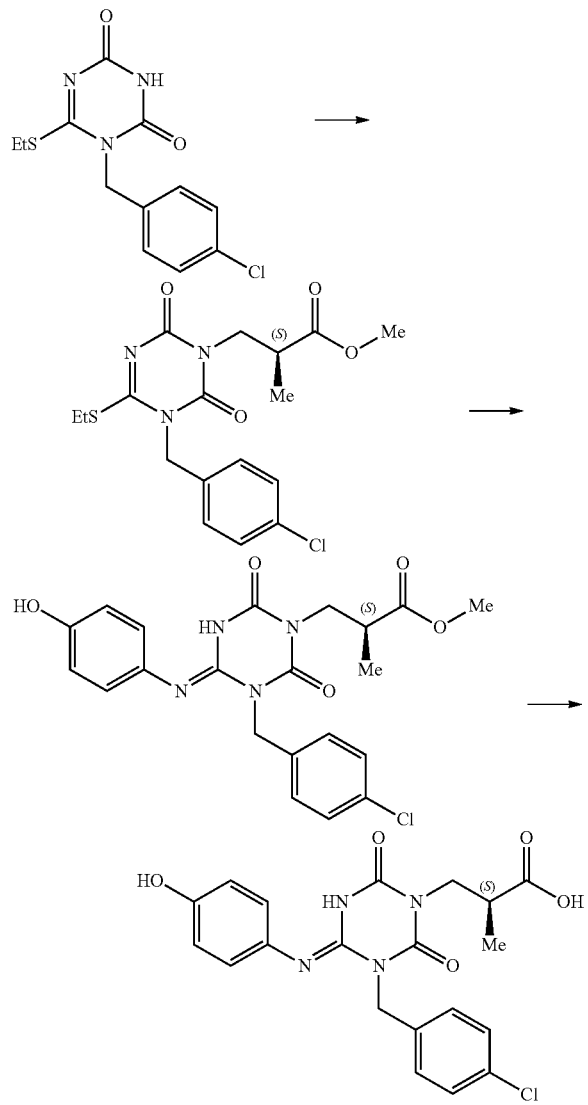

Means for Solving the Problem

As a result of intensive studies, the inventors of the present invention have found that, as crystalline forms of the compound represented by Formula (I), there are crystalline forms of an anhydrous Form I, an anhydrous Form II, and a dihydrate. Furthermore, they have found that the anhydrous crystal Form I and the dihydrate crystal are more stable than other crystal forms. In addition, they have found that the anhydrous crystal Form I has a low Compressibility index (%) of the crystal and has a favorable crystal fluidity as compared with other crystal forms.

In addition, the present inventors have found an intermediate having a high chemical purity and/or optical purity, a method for producing the intermediate, and a method for producing an optically active 1,3,5-triazine derivative having P2X$_3$ and/or P2X$_{2/3}$ antagonistic action.

The present invention relates to the following items (1'), (2'), (2'A), (2'B), (3'), (3'A), (3'B), (4') to (35'), (3"), (5"), and (36") to (42").

(1') A crystal of a compound represented by Formula (I):

[Chemical formula 7]

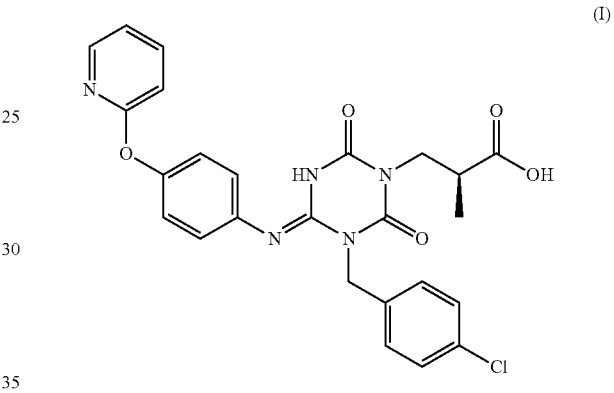

or a solvate thereof.

(2') An anhydrous crystal Form I of the compound according to the above item (1'), having, in a powder X-ray diffraction spectrum, characteristic peaks at:
 diffraction angles (2θ) of 15.8°±0.2°, 19.4°±0.2°, 21.7°±0.2°, 23.9°±0.2°, and 25.4°±0.2°; or
 diffraction angles (2θ) of 7.9°±0.2°, 9.3°±0.2°, 12.9°±0.2°, 15.8°±0.2°, and 19.4°±0.2°.

(2'A) An anhydrous crystal Form I of the compound according to the above item (1'), having characteristic peaks at diffraction angles (2θ) of 15.8°±0.2°, 19.4°±0.2°, 21.7°±0.2°, 23.9°±0.2°, and 25.4°±0.2° in a powder X-ray diffraction spectrum.

(2'B) An anhydrous crystal Form I of the compound according to the above item (1'), having characteristic peaks at diffraction angles (2θ) of 7.9°±0.2°, 9.3°±0.2°, 12.9°±0.2°, 15.8°±0.2°, and 19.4°±0.2° in a powder X-ray diffraction spectrum.

(3') An anhydrous crystal Form I of the compound according to the above item (1'), having, in a powder X-ray diffraction spectrum, characteristic peaks at:
 diffraction angles (2θ) of 12.6°±0.2°, 12.9°±0.2°, 15.8°±0.2°, 19.4°±0.2°, 21.7°±0.2°, 23.9°±0.2°, 25.4°±0.2°, 26.6°±0.2°, 27.8°±0.2°, and 32.8°±0.2°; or
 diffraction angles (2θ) of 7.9°±0.2°, 9.3°±0.2°, 12.9°±0.2°, 15.8°±0.2°, 17.2°±0.2°, 19.4°±0.2°, 21.7°±0.2°, 23.9°±0.2°, 25.4°±0.2°, and 27.8°±0.2°.

(3'A) An anhydrous crystal Form I of the compound according to the above item (1'), having characteristic peaks at diffraction angles (2θ) of 12.6°±0.2°, 12.9°±0.2°, 15.8°±0.2°, 19.4°±0.2°, 21.7°±0.2°, 23.9°±0.2°, 25.4°±0.2°, 26.6°±0.2°, 27.8°±0.2°, and 32.8°±0.2° in a powder X-ray diffraction spectrum.

(3'B) An anhydrous crystal Form I of the compound according to the above item (1'), having characteristic peaks at diffraction angles (2θ) of 7.9°±0.2°, 9.3°±0.2°, 12.9°±0.2°, 15.8°±0.2°, 17.2°±0.2°, 19.4°±0.2°, 21.7°±0.2°, 23.9°±0.2°, 25.4°±0.2° and 27.8°±0.2° in a powder X-ray diffraction spectrum.

(3") An anhydrous crystal Form I of the compound according to the above item (1'), having absorption peaks at 829 cm$^{-1}$±2 cm$^{-1}$, 989 cm$^{-1}$±2 cm$^{-1}$, 1013 cm$^{-1}$±2 cm$^{-1}$, 1128 cm$^{-1}$±2 cm$^{-1}$, and 1370 cm$^{-1}$±2 cm$^{-1}$ in Raman spectrum.

(4') A dihydrate crystal of the compound according to the above item (1'), having characteristic peaks at diffraction angles (2θ) of 5.7°±0.2°, 7.7°±0.2°, 11.8°±0.2°, 15.2°±0.2°, and 17.7°±0.2° in a powder X-ray diffraction spectrum.

(5') A dihydrate crystal of the compound according to the above item (1'), having characteristic peaks at diffraction angles (2θ) of 5.7°±0.2°, 7.7°±0.2°, 11.8°±0.2°, 15.2°±0.2°, 17.7°±0.2°, 20.6°±0.2°, 20.8°±0.2°, 26.5°±0.2°, 27.1°±0.2°, and 29.1°±0.2° in a powder X-ray diffraction spectrum.

(5") A dihydrate crystal of the compound according to the above item (1'), having absorption peaks at 871 cm$^{-1}$±2 cm$^{-1}$, 996 cm$^{-1}$±2 cm$^{-1}$, 1114 cm$^{-1}$±2 cm$^{-1}$, 1234 cm$^{-1}$±2 cm$^{-1}$, 1340 cm$^{-1}$±2 cm$^{-1}$, and 1577 cm$^{-1}$±2 cm$^{-1}$ in Raman spectrum.

(6') A pharmaceutical composition containing the crystal according to any one of the above items (1'), (2'), (2'A), (2'B), (3'), (3'A), (3'B), (4'), (5'), (3"), and (5").

(7') A method for producing the crystal according to any one of the above items (1'), (2'), (2'A), (2'B), (3'), (3'A), (3'B), (4'), (5'), (3"), and (5").

(8') The pharmaceutical composition according to the above item (6'), the pharmaceutical composition being a P2X$_3$ and/or P2X$_{2/3}$ antagonist.

(9') The pharmaceutical composition according to the above item (6'), the pharmaceutical composition being used for treating and/or preventing chronic cough.

(10') The pharmaceutical composition according to the above item (6'), the pharmaceutical composition being used for treating and/or preventing refractory chronic cough.

(11') A P2X$_3$ and/or P2X$_{2/3}$ antagonist, characterized by containing a crystal according to any one of the above items (1'), (2'), (2'A), (2'B), (3'), (3'A), (3'B), (4'), (5'), (3"), and (5").

(12') A therapeutic and/or preventive agent for chronic cough, characterized by containing the crystal according to any one of the above items (1'), (2'), (2'A), (2'B), (3'), (3'A), (3'B), (4'), (5'), (3"), and (5").

(13') A therapeutic and/or preventive agent for refractory chronic cough, characterized by containing the crystal according to any one of the above items (1'), (2'), (2'A), (2'B), (3'), (3'A), (3'B), (4'), (5'), (3"), and (5").

(14') A method for treatment and/or prevention of chronic cough, the method being characterized by administering a pharmaceutical composition containing the crystal according to any one of the above items (1'), (2'), (2'A), (2'B), (3'), (3'A), (3'B), (4'), (5'), (3"), and (5").

(15') A method for treatment and/or prevention of refractory chronic cough, the method being characterized by administering a pharmaceutical composition containing the crystal according to any of the above items (1'), (2'), (2'A), (2'B), (3'), (3'A), (3'B), (4'), (5'), (3"), and (5").

(16') Use of the crystal according to any one of the above items (1'), (2'), (2'A), (2'B), (3'), (3'A), (3'B), (4'), (5'), (3"), and (5") for producing a medicament for treatment and/or prevention of chronic cough.

(17') Use of the crystal according to any one of the above items (1'), (2'), (2'A), (2'B), (3'), (3'A), (3'B), (4'), (5'), (3"), and (5") for producing a medicament for treatment and/or prevention of refractory chronic cough.

(18') The crystal according to any one of the above items (1'), (2'), (2'A), (2'B), (3'), (3'A), (3'B), (4'), (5'), (3"), and (5") for treatment and/or prevention of chronic cough.

(19') The crystal according to any one of the above items (1'), (2'), (2'A), (2'B), (3'), (3'A), (3'B), (4'), (5'), (3"), and (5") for treatment and/or prevention of refractory chronic cough.

(20') The crystal according to the above item (1'), characterized by a powder X-ray diffraction spectrum substantially identical to that shown in FIG. 1.

(21') The crystal according to the above item (2'), characterized by a powder X-ray diffraction spectrum substantially identical to that shown in FIG. 1.

(22') The crystal according to the above item (2'A), characterized by a powder X-ray diffraction spectrum substantially identical to that shown in FIG. 1.

(23') The crystal according to the above item (2'B), characterized by a powder X-ray diffraction spectrum substantially identical to that shown in FIG. 1.

(24') The crystal according to the above item (3'), characterized by a powder X-ray diffraction spectrum substantially identical to that shown in FIG. 1.

(25') The crystal according to the above item (3'A), characterized by a powder X-ray diffraction spectrum substantially identical to that shown in FIG. 1.

(26') The crystal according to the above item (3'B), characterized by a powder X-ray diffraction spectrum substantially identical to that shown in FIG. 1.

(27') The crystal according to the above item (4'), characterized by a powder X-ray diffraction spectrum substantially identical to that shown in FIG. 4.

(28') The crystal according to the above item (5'), characterized by a powder X-ray diffraction spectrum substantially identical to that shown in FIG. 4.

(29') The crystal according to the above item (1'), characterized by Raman spectrum substantially identical to that shown in FIG. 2.

(30') An anhydrous crystal Form I of the compound according to the above item (1'), characterized by one or more physicochemical properties selected from the group consisting of the following (i) and (ii):
  (i) having, in a powder X-ray diffraction spectrum, characteristic peaks at:
    diffraction angles (2θ) of 15.8°±0.2°, 19.4°±0.2°, 21.7°±0.2°, 23.9°±0.2°, and 25.4°±0.2°, or
    diffraction angles (2θ) of 7.9°±0.2°, 9.3°±0.2°, 12.9°±0.2°, 15.8°±0.2°, and 19.4°±0.2°; and
  (ii) having absorption peaks at 829 cm$^{-1}$±2 cm$^{-1}$, 989 cm$^{-1}$±2 cm$^{-1}$, 1013 cm$^{-1}$±2 cm$^{-1}$, 1128 cm$^{-1}$±2 cm$^{-1}$, and 1370 cm$^{-1}$±2 cm$^{-1}$ in Raman spectrum.

(31') An anhydrous crystal Form I of the compound according to the above item (1'), characterized by one or more physicochemical properties selected from the group consisting of the following (i) and (ii):
  (i) having characteristic peaks at diffraction angles (2θ) of 15.8°±0.2°, 19.4°±0.2°, 21.7°±0.2°, 23.9°±0.2°, and 25.4°±0.2° in a powder X-ray diffraction spectrum; and (ii) having absorption peaks at 829 cm$^{-1}$±2 cm$^{-1}$, 989 cm$^{-1}$±2 cm$^{-1}$, 1013 cm$^{-1}$±2 cm$^{-1}$, 1128 cm$^{-1}$±2 cm$^{-1}$, and 1370 cm$^{-1}$±2 cm$^{-1}$ in Raman spectrum.

(32') An anhydrous crystal Form I of the compound according to the above item (1'), characterized by one or more physicochemical properties selected from the group consisting of the following (i) and (ii):
  (i) having characteristic peaks at diffraction angles (2θ) of 7.9°±0.2°, 9.3°±0.2°, 12.9°±0.2°, 15.8°±0.2°, and 19.4°±0.2° in a powder X-ray diffraction spectrum; and
  (ii) having absorption peaks at 829 cm$^{-1}$±2 cm$^{-1}$, 989 cm$^{-1}$±2 cm$^{-1}$, 1013 cm$^{-1}$±2 cm$^{-1}$, 1128 cm$^{-1}$±2 cm$^{-1}$, and 1370 cm$^{-1}$±2 cm$^{-1}$ in Raman spectrum.

(33') An anhydrous crystal Form I of the compound according to the above item (1'), characterized by one or more physicochemical properties selected from the group consisting of the following (i) and (ii):
  (i) having, in a powder X-ray diffraction spectrum, characteristic peaks at: diffraction angles (2θ) of 12.6°±0.2°, 12.9°±0.2°, 15.8°±0.2°, 19.4°±0.2°, 21.7°±0.2°, 23.9°±0.2°, 25.4°±0.2°, 26.6°±0.2°, 27.8°±0.2°, and 32.8°±0.2°, or
  diffraction angles (2θ) of 7.9°±0.2°, 9.3°±0.2°, 12.9°±0.2°, 15.8°±0.2°, 17.2°±0.2°, 19.4°±0.2°, 21.7°±0.2°, 23.9°±0.2°, 25.4°±0.2°, and 27.8°±0.2°; and
  (ii) having absorption peaks at 829 cm$^{-1}$±2 cm$^{-1}$, 989 cm$^{-1}$±2 cm$^{-1}$, 1013 cm$^{-1}$±2 cm$^{-1}$, 1128 cm$^{-1}$±2 cm$^{-1}$, and 1370 cm$^{-1}$±2 cm$^{-1}$ in Raman spectrum.

(34') An anhydrous crystal Form I of the compound according to the above item (1'), characterized by one or more physicochemical properties selected from the group consisting of the following (i) and (ii):
  (i) having characteristic peaks at diffraction angles (2θ) of 12.6°±0.2°, 12.9°±0.2°, 15.8°±0.2°, 19.4°±0.2°, 21.7°±0.2°, 23.9°±0.2°, 25.4°±0.2°, 26.6°±0.2°, 27.8°±0.2°, and 32.8°±0.2° in a powder X-ray diffraction spectrum; and
  (ii) having absorption peaks at 829 cm$^{-1}$±2 cm$^{-1}$, 989 cm$^{-1}$±2 cm$^{-1}$, 1013 cm$^{-1}$±2 cm$^{-1}$, 1128 cm$^{-1}$±2 cm$^{-1}$, and 1370 cm$^{-1}$±2 cm$^{-1}$ in Raman spectrum.

(35') An anhydrous crystal Form I of the compound according to the above item (1'), characterized by one or more physicochemical properties selected from the group consisting of the following (i) and (ii):
  (i) having characteristic peaks at diffraction angles (2θ) of 7.9°±0.2°, 9.3°±0.2°, 12.9°±0.2°, 15.8°±0.2°, 17.2°±0.2°, 19.4°±0.2°, 21.7°±0.2°, 23.9°±0.2°, 25.4°±0.2°, and 27.8°±0.2° in a powder X-ray diffraction spectrum; and
  (ii) having absorption peaks at 829 cm$^{-1}$±2 cm$^{-1}$, 989 cm$^{-1}$±2 cm$^{-1}$, 1013 cm$^{-1}$±2 cm$^{-1}$, 1128 cm$^{-1}$±2 cm$^{-1}$, and 1370 cm$^{-1}$±2 cm$^{-1}$ in Raman spectrum.

(36") An anhydrous crystal Form I of the compound according to the above item (1'), characterized by one or more spectra and/or curves selected from the group consisting of the following (a) and (b):
  (a) a powder X-ray diffraction spectrum substantially identical to that shown in FIG. 1; and
  (b) Raman spectrum substantially identical to that shown in FIG. 2.

(37") The crystal according to the above item (1'), characterized by Raman spectrum substantially identical to that shown in FIG. 6.

(38") A dihydrate crystal of the compound according to the above item (1'), characterized by one or more physicochemical properties selected from the group consisting of the following (i) and (ii):
  (i) having characteristic peaks at diffraction angles (2θ) of 5.7°±0.2°, 7.7°±0.2°, 11.8°±0.2°, 15.2°±0.2°, and 17.7°±0.2° in a powder X-ray diffraction spectrum; and
  (ii) having absorption peaks at, 871 cm$^{-1}$±2 cm$^{-1}$, 996 cm$^{-1}$±2 cm$^{-1}$, 1114 cm$^{-1}$±2 cm$^{-1}$, 1234 cm$^{-1}$±2 cm$^{-1}$, 1340 cm$^{-1}$±2 cm$^{-1}$, and 1577 cm$^{-1}$±2 cm$^{-1}$ in Raman spectrum.

(39") A dihydrate crystal of the compound according to the above item (1'), characterized by one or more physicochemical properties selected from the group consisting of the following (i) and (ii):
  (i) having characteristic peaks at diffraction angles (2θ) of 5.7°±0.2°, 7.7°±0.2°, 11.8°±0.2°, 15.2°±0.2°, 17.7°±0.2°, 20.6°±0.2°, 20.8°±0.2°, 26.5°±0.2°, 27.1°±0.2°, and 29.1°±0.2° in a powder X-ray diffraction spectrum; and
  (ii) having absorption peaks at, 871 cm$^{-1}$±2 cm$^{-1}$, 996 cm$^{-1}$±2 cm$^{-1}$, 1114 cm$^{-1}$±2 cm$^{-1}$, 1234 cm$^{-1}$±2 cm$^{-1}$, 1340 cm$^{-1}$±2 cm$^{-1}$, and 1577 cm$^{-1}$±2 cm$^{-1}$ in Raman spectrum.

(40") A dihydrate crystal of the compound according to the above item (1'), characterized by one or more spectra and/or curves selected from the group consisting of the following (a) and (b):
  (a) a powder X-ray diffraction spectrum substantially identical to that shown in FIG. 4; and
  (b) Raman spectrum substantially identical to that shown in FIG. 6.

(41") An anhydrous crystal Form I of the compound of the above item (1'), which when measured at 298.15 K is substantially in accordance with the following crystallographic data:

Space group: P1
a=9.8720 (5) Å
b=10.9952 (5) Å
c=12.2781 (6) Å
α=67.712 (4)°
β=80.870 (4)°
γ=80.870 (4)°

(42") An anhydrous crystal Form I of the compound of the above item (1'), above, which when measured at 298.15 K is characterized by the following crystallographic data:

Space group: P1
a=9.9 Å±0.5 Å
b=11.0 Å±0.5 Å
c=12.3 Å±0.5 Å
α=67.7°±0.5°
β=80.9°±0.5°
γ=86.9°±0.5°

The present invention also relates to the following items (1) to (34).

(1) A crystal of a compound represented by Formula (I):

[Chemical formula 8]

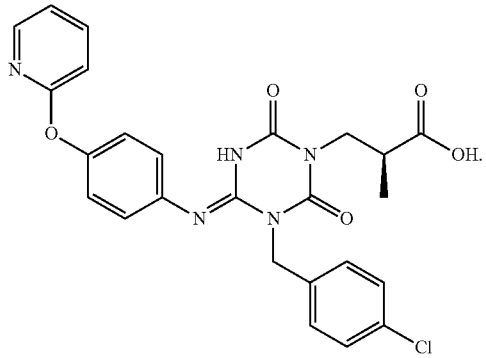

(I)

or a solvate thereof.

(2) A crystal of the compound according to the above item (1), having characteristic peaks at diffraction angles (2θ) of 15.8°±0.2°, 19.4°±0.2°, 21.7°±0.2°, 23.9°±0.2°, 25.4°±0.2° or 7.9°±0.2°, 9.3°±0.2°, 12.9°±0.2°, 15.8°±0.2°, and 19.4°±0.2° in a powder X-ray diffraction spectrum.

(3) A crystal of the compound according to the above item (1), having, in a powder X-ray diffraction spectrum, characteristic peaks at:
diffraction angles (2θ) of 12.6°±0.2°, 12.9°±0.2°, 15.8°±0.2°, 19.4°±0.2°, 21.7°±0.2°, 23.9°±0.2°, 25.4°±0.2°, 26.6°±0.2°, 27.8°±0.2°, and 32.8°±0.2°; or
differential angles (2θ) of 7.9°±0.2°, 9.3°±0.2°, 12.9°±0.2°, 15.8°±0.2°, 17.2°±0.2°, 19.4°±0.2°, 21.7°±0.2°, 23.9°±0.2°, 25.4°±0.2°, and 27.8°±0.2°.

(4) A pharmaceutical composition containing the crystal according to any one of the above items (1) to (3).

(5) A process for producing the crystal according to any one of the above items (1) to (3).

(6) A process for producing a compound represented by Formula (IV):

[Chemical Formula 9]

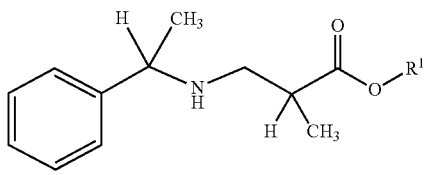

(IV)

wherein R¹ is C1-C4 alkyl,
or a salt thereof,
characterized by causing a reaction between a compound represented by Formula (II):

[Chemical Formula 10]

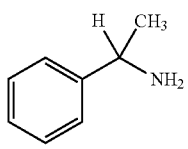

(II)

or a salt thereof, and a compound represented by Formula (III):

[Chemical Formula 11]

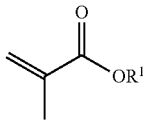

(III)

wherein $R^1$ is C1-C4 alkyl,
or a salt thereof,
under the presence of one or more additives selected from the group consisting of lithium chloride, calcium chloride, magnesium chloride, lithium bromide, p-toluenesulfonic acid, methanesulfonic acid, and trifluoromethanesulfonic acid.

(7) The process according to the above item (6), wherein the additive is lithium chloride.

(8) A process for producing a p-toluenesulfonic acid salt of a compound represented by Formula (IV-A):

[Chemical formula 12]

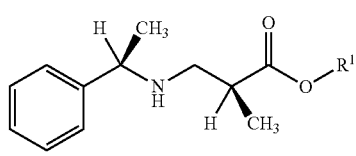

(IV-A)

wherein $R^1$ is C1-C4 alkyl,
characterized by:
obtaining a compound represented by Formula (IV) or a salt thereof by the process according to the above item (6) or (7), and
adding p-toluenesulfonic acid thereto.

(9) A process for producing a p-toluenesulfonic acid salt of a compound represented by Formula (IV-A):

[Chemical formula 13]

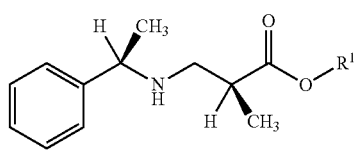

(IV-A)

wherein $R^1$ is a C1-C4 alkyl,
characterized in that the additive is p-toluenesulfonic acid in the process according to item (6).

(10) The process according to any one of the above items (6) to (9), wherein $R^1$ is methyl.

(11) A p-toluenesulfonic acid salt of a compound represented by Formula (IV-B):

[Chemical formula 14]

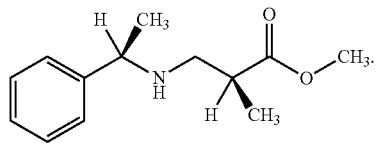

(IV-B)

(12) A process for producing a ½ sulfuric acid salt of a compound represented by Formula (V):

[Chemical formula 15].

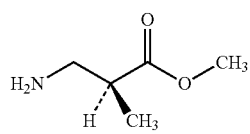

(V)

characterized by:
subjecting a p-toluenesulfonic acid salt of a compound represented by Formula (IV-B):

[Chemical formula 16]

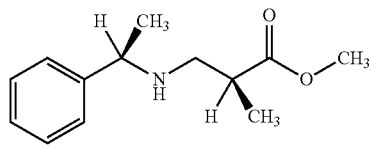

(IV-B)

to a hydrogenolysis reaction; and
adding sulfuric acid thereto.

(13) A ½ sulfuric acid salt of a compound represented by Formula (V):

[Chemical formula 17]

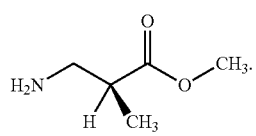

(V)

(14) A process for producing a compound represented by Formula (I):

[Chemical formula 18]

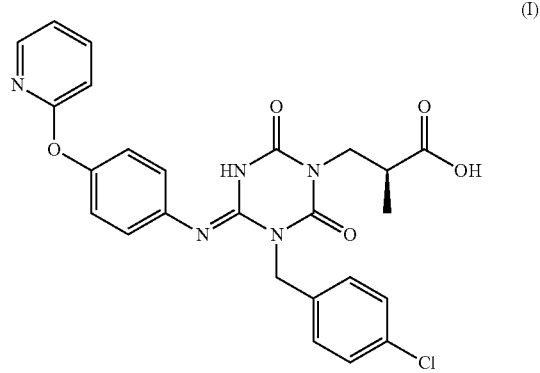

(I)

or a salt thereof,
characterized by:
subjecting a compound represented by Formula (VI):

[Chemical formula 19]

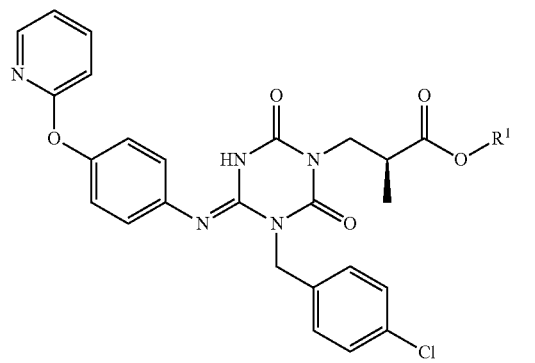

(VI)

wherein $R^1$ is C1-C4 alkyl,
or a salt thereof,
to a hydrolysis reaction under the presence of one or more solvents selected from the group consisting of isopropyl alcohol, tetrahydrofuran, and t-butanol.

(15) The process according to the above item (14), wherein $R^1$ is methyl.

(16) A process for producing a compound represented by Formula (VI):

[Chemical formula 20]

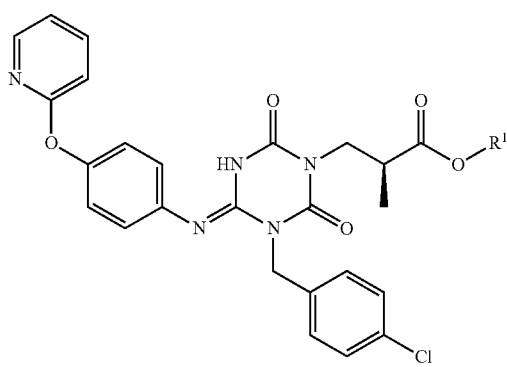

(VI)

wherein $R^1$ is methyl,
or a salt thereof,
wherein the process comprises the step of:
  producing a p-toluenesulfonic acid salt of a compound represented by Formula (IV-B):

[Chemical formula 21]

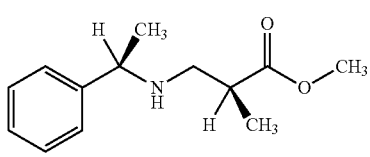

(IV-B)

by the process according to any one of the above items (6) to (10).

(17) A process for producing a compound represented by Formula (VI):

[Chemical formula 22]

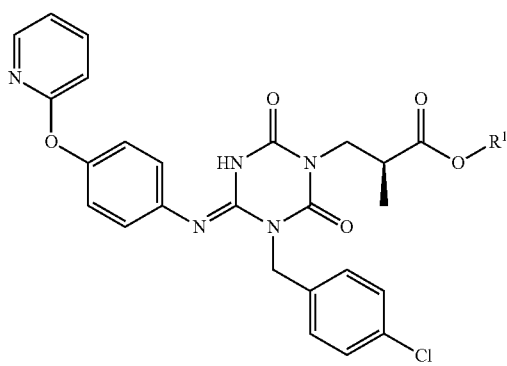

(VI)

wherein $R^1$ is methyl,
or a salt thereof,
wherein the process comprises the step of:
  producing a ½ sulfuric acid salt of a compound represented by Formula (V):

[Chemical formula 23]

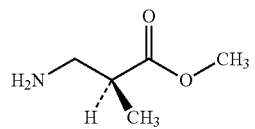

(V)

by the process according to the item (12):

(18) A process for producing a compound represented by Formula (VI):

[Chemical formula 24]

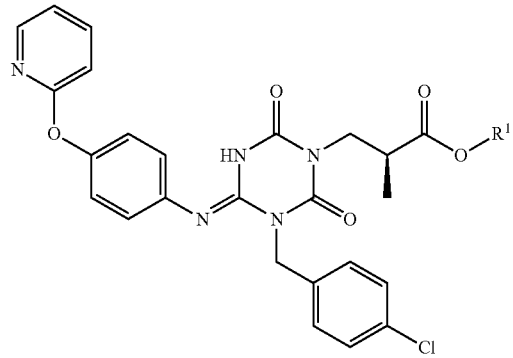

(VI)

wherein $R^1$ is methyl,
or a salt thereof,
wherein the process comprises the steps of:
  producing a p-toluenesulfonic acid salt of a compound represented by Formula (IV-B):

[Chemical formula 25]

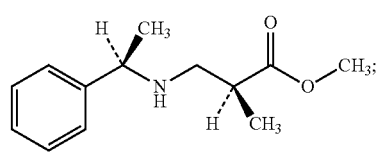

(IV-B)

by the process according to any one of the above items (6) to (10); and
  producing a ½ sulfuric acid salt of a compound represented by Formula (V):

[Chemical formula 26]

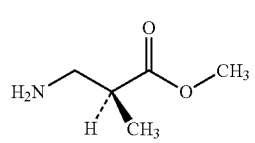

(V)

by the process according to the item (12).

(19) A process for producing a compound represented by Formula (I):

[Chemical formula 27]

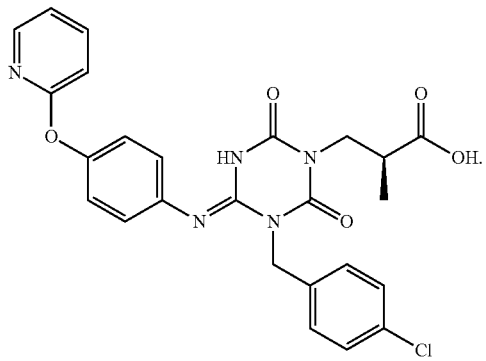

(I)

or a salt thereof,
characterized by:
obtaining a compound represented by Formula (VI):

[Chemical formula 28]

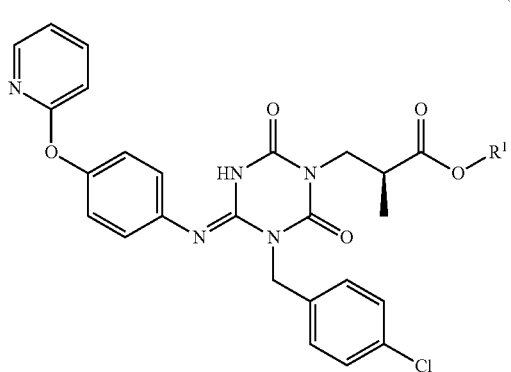

(VI)

wherein $R^1$ is methyl,
or a salt thereof, by the process according to any one of the above items (16) to (18); and
subjecting the compound represented by Formula (VI) or a salt thereof thus obtained to a hydrolysis reaction under the presence of one or more solvents selected from the group consisting of isopropyl alcohol, tetrahydrofuran, and t-butanol.

(20) The pharmaceutical composition according to the above item (4), the pharmaceutical composition being a $P2X_3$ and/or $P2X_{2/3}$ antagonist.

(21) The pharmaceutical composition according to the above item (4), the pharmaceutical composition being used for treating and/or preventing chronic cough.

(22) The pharmaceutical composition according to the above item (4), the pharmaceutical composition being used for treating and/or preventing refractory chronic cough.

(23) A $P2X_3$ and/or $P2X_{2/3}$ antagonist, characterized by containing a crystal according to any one of the above items (1) to (3).

(24) A therapeutic and/or preventive agent for chronic cough, characterized by containing the crystal according to any one of the above items (1) to (3).

(25) A therapeutic and/or preventive agent for refractory chronic cough, characterized by containing the crystal according to any one of the above items (1) to (3).

(26) A method for treatment and/or prevention of chronic cough, the method being characterized by administering a pharmaceutical composition containing the crystal according to any one of the above items (1) to (3).

(27) A method for treatment and/or prevention of refractory chronic cough, the method being characterized by administering a pharmaceutical composition containing the crystal according to any one of the above items (1) to (3).

(28) Use of the crystal according to any one of the above items (1) to (3) for producing a medicament for treatment and/or prevention of chronic cough.

(29) Use of the crystal according to any one of the above items (1) to (3) for producing a medicament for treatment and/or prevention of refractory chronic cough.

(30) The crystal according to any one of the above items (1) to (3) for treatment and/or prevention of chronic cough.

(31) The crystal according to any one of the above items (1) to (3) for treatment and/or prevention of refractory chronic cough.

(32) The crystal according to the above item (1), characterized by a powder X ray diffraction spectrum substantially identical to that shown in FIG. 1.

(33) The crystal according to the above item (2), characterized by a powder X ray diffraction spectrum substantially identical to that shown in FIG. 1.

(34) The crystal according to the above item (3), characterized by a powder X ray diffraction spectrum substantially identical to that shown in FIG. 1.

(35) The crystal according to the above item (1), characterized by Raman spectrum substantially identical to that shown in FIG. 2.

(36) The crystal according to the above item (2), characterized by Raman spectrum substantially identical to that shown in FIG. 2.

(37) The crystal according to the above item (3), characterized by Raman spectrum substantially identical to that shown in FIG. 2.

Effect of the Invention

A crystal of the present invention is useful as an active pharmaceutical ingredient of a compound represented by Formula (I). That is, the pharmaceutical composition containing a crystal of the present invention is very useful as a therapeutic agent or a prophylactic agent for chronic cough or refractory chronic cough.

Among the crystals of the present invention, an anhydrous crystal Form I and a dihydrate crystal are useful as active pharmaceutical ingredients.

Further, the anhydrous crystal Form I has the following characteristics:

(i) having a low Compressibility index (%) of the crystal and has a favorable crystal fluidity;
(ii) having a crystalline form containing none of residual solvents listed in the ICH Q3C guideline; and
(iii) having high solid stability, and generating few kinds of analog substances during storage of the active pharmaceutical ingredient.

In addition, the dihydrate crystal has the characteristics of the above (ii) and (iii).

In addition, a process method of the present invention can produce compounds useful as process intermediates, represented by Formula (IV) and Formula (V), and a compound represented by Formula (I) and a crystal thereof.

The present process method is an industrially excellent process method, and the characteristics of the process method of the present invention can include the following points:
 (a) in the step of producing the compound represented by Formula (IV), the aza-Michael addition reaction can be accelerated by adding LiCl or the like;
 (b) in the step of producing the compound represented by Formula (V), by obtaining a product as a ½ sulfate, the product can be obtained in a high yield; and
 (c) in the step of producing the compound represented by Formula (I), racemization can be suppressed by using isopropyl alcohol or the like as a reaction solvent.

BRIEF DESCRIPTION OF THE DRAWINGS

FIG. 1 shows a powder X-ray diffraction pattern of an anhydrous crystal Form I of a compound represented by Formula (I). The horizontal axis represents 2θ(°), and the vertical axis represents an intensity (Count).

FIG. 2 shows a Raman spectrum of the anhydrous crystal Form I of the compound represented by Formula (I). The horizontal axis represents a Raman shift ($cm^{-1}$), and the vertical axis represents a peak intensity.

FIG. 3 shows DSC analysis results of the anhydrous crystal Form I of the compound represented by Formula (I).

FIG. 4 shows a powder X-ray diffraction pattern of a dihydrate crystal of the compound represented by Formula (I). The horizontal axis represents 2θ(°), and the vertical axis represents an intensity (Count).

FIG. 5 shows TG/DTA analysis results of the dihydrate crystal of the compound represented by Formula (I). The vertical axis represents a calorie (μV) or a weight change (%), and the horizontal axis represents temperature (° C.). "Cel" in the figure means a degree Celsius (° C.).

FIG. 6 shows a Raman spectrum of the dihydrate crystal of the compound represented by Formula (I). The horizontal axis represents a Raman shift ($cm^{-1}$), and the vertical axis represents a peak intensity.

FIG. 7 shows a molecular structural diagram of the anhydrous crystal Form I of the compound represented by Formula (I) (showing a molecule containing N3).

FIG. 8 shows a molecular structural diagram of the anhydrous crystal Form I of the compound represented by Formula (I) (showing a molecule containing N8).

FIG. 9 shows NMR of an ethyl acetate/hexane solvate crystal of the compound represented by Formula (I). The horizontal axis represents a chemical shift (δ) value, and the vertical axis represents a relative intensity of a proton signal.

FIG. 10 shows a powder X-ray diffraction pattern of the ethyl acetate/hexane solvate crystal of the compound represented by Formula (I). The horizontal axis represents 2θ(°), and the vertical axis represents an intensity (Count).

FIG. 11 shows a Raman spectrum of the ethyl acetate/hexane solvate crystal of the compound represented by Formula (I). The horizontal axis represents a Raman shift ($cm^{-1}$), and the vertical axis represents a peak intensity.

FIG. 12 shows a powder X-ray diffraction pattern of an anhydrous crystal Form II of a compound represented by Formula (I). The horizontal axis represents 2θ(°), and the vertical axis represents an intensity (Count).

FIG. 13 shows TG/DTA analysis results of the ethyl acetate/hexane solvate crystal of the compound represented by Formula (I). The vertical axis represents a calorie (μV) or a weight change (%), and the horizontal axis represents temperature (° C.). "Cel" in the figure means a degree Celsius (° C.).

MODE FOR CARRYING OUT THE INVENTION

The selection and control of the solid form is important, especially for a compound as a drug. Careful selection and control of the solid form can reduce problems in production, formulation, or administration related with the compound.

If there is no reference in particular, a numerical value in the present specification and claims is an approximate value. A numerical change originates from a device calibration, a device error, substance purity, a crystal size, a sample size, temperature, and other factors.

The term "crystal" used in the present specification means a solid in which atoms, ions, molecules, and the like constituting the crystal are three-dimensionally and regularly arranged, and is distinguished from an amorphous solid not having such a regular internal structure. The crystal of the present invention may be a single crystal, a twin crystal, a polycrystal, or the like.

Furthermore, crystal polymorphs may be present in "crystals". They are collectively referred to as "crystalline forms" and are intended to be included in the present invention.

In addition, the "compound represented by Formula (I)" can form a solvate with water (that is, a hydrate) or a solvate with a general organic solvent, and such a solvate is also intended to be included within the scope of the present invention.

The crystalline form and the crystallinity can be measured by many techniques including, for example, powder X-ray diffractometry, Raman spectroscopy, infrared absorption spectroscopy, moisture adsorption/desorption measurement, differential scanning calorimetry, and dissolution characteristics.

The term "salt" used in the present specification means, for example, that the "compound represented by Formula (I)" and counter molecules are regularly arranged in the same crystal lattice, and any number of counter molecules may be included. The term refers to one in which an ionic bonding is mediated by proton transfer between a compound and a counter molecule in a crystal lattice.

Studies on salt formation provide a means to alter physicochemical characteristics of an agent and resulting biological characteristics without altering its chemical structure. Salt formation can have a dramatic impact on properties of the agent. In the selection of a suitable salt, hygroscopicity, stability, solubility and processing properties of the salt are also important aspects. A solubility of a salt can affect its suitability for use as an agent. If the aqueous solubility is low, the dissolution rate in in vivo administration is limited by the absorption process and may result in low bioavailability. In addition, the low aqueous solubility may make it difficult to administer by injection, and therefore, the selection of an appropriate administration route may be limited.

The "compound represented by Formula (I)" may be converted into a solvate, a pharmaceutically acceptable salt, or a solvate of a salt. In one aspect of the present invention, the compound is in the form of a base addition salt. Examples of the base addition salt include salts made from pharmaceutically acceptable non-toxic bases including inorganic and organic bases. Examples of the salt derived from inorganic bases include, but are not limited to, salts of aluminum, calcium, lithium, potassium, magnesium, sodium, zinc, and other metal salts. Examples of a pharmaceutically acceptable salt based on a non-toxic base include salts of primary, secondary or tertiary amines, and substituted amines including naturally occurring substituted amines, cyclic amines and basic ion exchange resins, such as, arginine, betaine, benzathine, caffeine, choline, chloroprocaine, cycloprocaine, N'N'-dibenzylethylenediamine, diethanolamine, diethylamine, 2-diethyl-aminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, meglumine, morpholine, piperazine, piperidine, polyamine resins, procaine, purines, tertiary butylamine (2-methylpropane-2-amine), theobromine, triethylamine, trimethylamine, tripropylamine, and tromethamine; as well as nontoxic ammonium and quaternary ammonium, and salts of cations including, but not limited to, ammonium, tetramethylammonium, and tetraethylammonium.

Examples of the acid addition salts of "the compound represented by Formula (I)", "the compound represented by Formula (II)", "the compound represented by Formula (IV)", "the compound represented by Formula (IV-A)", "the compound represented by Formula (IV-B)" and "the compound represented by Formula (V)" include a compound having:
  an inorganic acid such as hydrochloric acid, hydrobromic acid, orthophosphoric acid, nitric acid, phosphoric acid or sulfuric acid; or
  an organic acid such as formic acid, methanesulfonic acid, ethanesulfonic acid, p-toluenesulfonic acid, acetic acid, propionic acid, lactic acid, citric acid, fumaric acid, malic acid, succinic acid, salicylic acid, maleic acid, glycerophosphoric acid, tartaric acid, benzoic acid, glutamic acid, aspartic acid, benzenesulfonic acid, naphthalenesulfonic acid such as 2-naphthalenesulfonic acid, hexanoic acid, and acetylsalicylic acid.

The term "solvate" used in the present specification refers to, for example, one that is regularly arranged with an arbitrary number of solvent molecules with respect to the "compound represented by Formula (I)".

Examples of the solvent molecule include acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethylene glycol, formamide, hexane, methanol, 2-methoxyethanol, methylbutyl ketone, methylcyclohexane, N-methylpyrrolidone, nitromethane, pyridine, sulfolane, tetralin, toluene, 1,1,2-trichloroethene, xylene, acetic acid, anisole, 1-butanol, 2-butanol, t-butanol, n-butyl acetate, t-butyl methyl ether, cumene, dimethyl sulfoxide, ethyl acetate, diethyl ether, ethyl formate, formic acid, heptane, isobutyl acetate, isopropyl acetate, methyl acetate, 3-methyl-1-butanol, methyl ethyl ketone, methyl isobutyl ketone, 2-methyl-1-propanol, pentane, 1-pentanol, 1-propanol, 2-propanol, propyl acetate, tetrahydrofuran, water (i.e., hydrate), ethanol, acetone, 1,1-diethoxypropane, 1,1-dimethoxymethane, 2,2-dimethoxypropane, isooctane, isopropyl ether, methyl isopropyl ketone, methyl tetrahydrofuran, petroleum ether, trichloroacetic acid, and trifluoroacetic acid.

Preferred examples include acetic acid, anisole, 1-butanol, 2-butanol, n-butyl acetate, t-butyl methyl ether, cumene, dimethyl sulfoxide, ethyl acetate, diethyl ether, ethyl formate, formic acid, heptane, isobutyl acetate, isopropyl acetate, methyl acetate, 3-methyl-1 butanol, methyl ethyl ketone, methyl isobutyl ketone, 2-methyl-1-propanol, pentane, 1-pentanol, 1-propanol, 2-propanol, propyl acetate, tetrahydrofuran, water (i.e., hydrate), ethanol, acetone, 1,1-diethoxypropane, 1,1-dimethoxymethane, 2,2-dimethoxypropane, isooctane, isopropyl ether, methyl isopropyl ketone, methyl tetrahydrofuran, petroleum ether, trichloroacetic acid and trifluoroacetic acid.

More preferred examples thereof include water (i.e., hydrate), ethanol, acetone, 1,1-diethoxypropane, 1,1-dimethoxymethane, 2,2-dimethoxypropane, isooctane, isopropyl ether, methyl isopropyl ketone, methyl tetrahydrofuran, petroleum ether, trichloroacetic acid, and trifluoroacetic acid.

When the "compound represented by Formula (I)" is left to stand in the atmosphere, moisture is absorbed, and adsorbed water may adhere thereto, or a hydrate may be formed.

Also, for the "compound represented by Formula (II)", the "compound represented by Formula (III)", the "compound represented by Formula (IV)", the "compound represented by Formula (IV-A)", the "compound represented by Formula (IV-B)", the "compound represented by Formula (V)" and the "compound represented by Formula (VI)", solvates can be formed.

The hydrate of the present invention or the crystal thereof contains, for example, about 2 molar equivalents of water molecules with respect to "the compound represented by Formula (I)". Preferable examples of the hydrate crystal of the present invention include a dihydrate.

The hydrate of the present invention or the crystal thereof has a water content of, for example, 4.7 to 9.7 wt %. Preferably, the water content is about 5.6 to 7.6 wt % (the theoretical value of the dihydrate is 6.6%, but the moisture content may increase due to the influence of water adhering to the crystal, or a part of water in the crystal may be desorbed before measurement whereby the moisture content may decrease).

The crystal of the present invention may be a deuterium conversion product. The crystal of the present invention may be labeled with an isotope (examples: $^{3}H$, $^{14}C$, $^{35}S$, $^{125}I$).

The term "anhydride" used in the present specification is synonymous with "ansolvate", "non-solvate," "anhydrate," and "non-hydrate".

The compound represented by Formula (I) is a $P2X_3$ and/or $P2X_{2/3}$ antagonist described in Patent Document 9:

[Chemical formula 29]

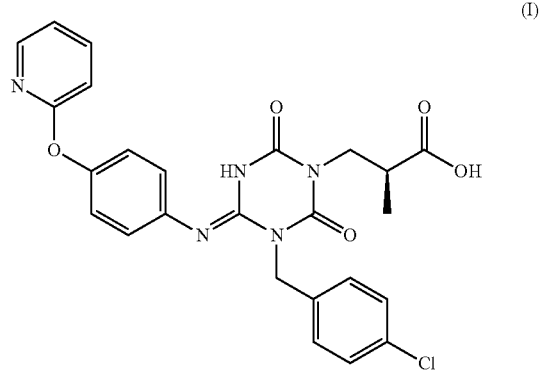 [SMILES: C[C@@H](Cn1c(=O)[nH]/c(=N\c2ccc(Oc3ccccn3)cc2)n(Cc2ccc(Cl)cc2)c1=O)C(=O)O]

(I)

It is very useful as a therapeutic agent or a prophylactic agent for chronic cough. The compound represented by Formula (I) can be prepared with reference to Examples of the present application.

A tautomer of the compound represented by Formula (I) is a compound (amino form) represented by Formula (I'):

[Chemical formula 30]

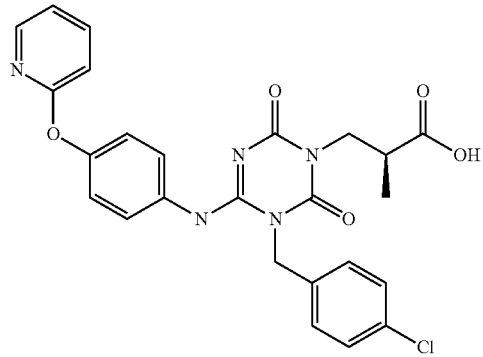

(I')

This compound has a P2X$_3$ and/or P2X$_{2/3}$ receptor antagonistic action, like the compound represented by Formula (I).

In addition, the compound represented by Formula (VI) can also take tautomers in the same manner as described above.

[Chemical formula 31]

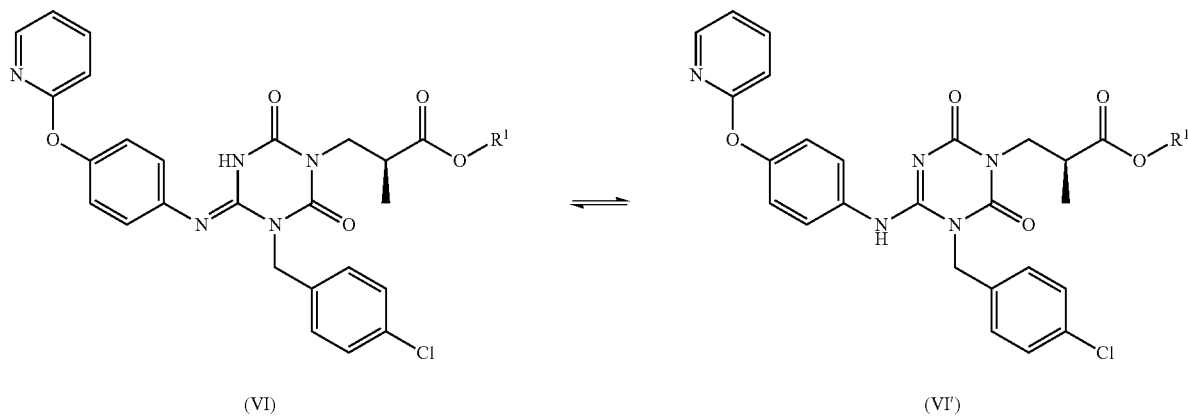

(VI)   (VI')

The compound represented by Formula (I) may also include a mixture of the compound represented by Formula (I) (imino form) and the compound represented by Formula (I') (amino form), and they may be mixed at an arbitrary ratio. The same applies to the compound represented by Formula (VI).

As a result of single crystal structure analysis, the anhydrous crystal Form I of the compound represented by Formula (I) was confirmed to have the following molecular structure (imino form) (details are described in Example 3).

[Chemical formula 32]

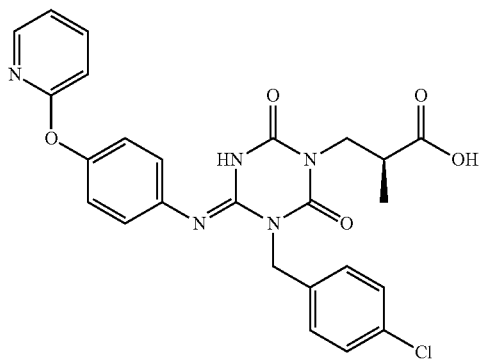

For the dihydrate crystal of the compound represented by Formula (I) and the anhydrous crystal Form II of the compound represented by Formula (I), the molecular structure (amino form/imino form) has not been identified.

Powder X-Ray Diffraction (XRPD)

In general, a crystalline organic compound is composed of a large number of molecules arranged periodically in a three-dimensional space. Structural periodicity typically develops physical properties that are clearly distinguishable by most spectroscopic probes (for example, X-ray diffraction, infrared spectrum, Raman spectrum, and solid-state NMR). Among them, powder X-ray diffraction (XRPD) is one of the most sensitive analysis methods for measuring the crystallinity of a solid. When the crystal is irradiated with X-rays, the X-rays are reflected by the crystal lattice planes and interfere with each other, and only the diffraction rays in the direction satisfying the condition predicted by Bragg's law have increased in intensities, whereby ordered diffraction rays corresponding to the period of the structure are shown. On the other hand, for an amorphous solid, an ordered diffraction ray is not observed. An amorphous solid usually does not have an ordered repetition period in its structure, so that a diffraction phenomenon does not occur and shows a featureless broad XRPD pattern (also referred to as a halo pattern).

The crystalline form of the anhydride of the compound represented by Formula (I) can be characterized by a powder X-ray diffraction pattern and characteristic peaks. The crystalline form of the anhydride of the compound represented by Formula (I) can be distinguished from other crystalline forms (for example, a hydrate crystal) by the presence of characteristic diffraction peaks. Characteristic diffraction peaks used in the present specification are those selected from the observed diffraction patterns. In distinguishing a plurality of crystals, a peak that is observed in a crystal and is not observed in the other crystals, rather than the size of the peak, is a preferred characteristic peak in specifying the crystal. With such a characteristic peak, even one or two peaks can characterize the crystal. When the charts obtained by the measurement are compared and these characteristic peaks coincide with each other, it can be said that the powder X-ray diffraction spectra substantially coincide with each other.

In general, since the diffraction angle (2θ) in powder X-ray diffraction may have an error within a range of ±0.2°, the value of the diffraction angle of powder X-ray diffraction needs to be understood as including a numerical value within a range of about ±0.2°. Therefore, the present invention encompasses not only crystals in which the diffraction angles of peaks in powder X-ray diffraction completely coincide with each other, but also crystals in which the diffraction angles of peaks coincide with each other with an error of about ±0.2°.

It is generally known that the intensities of the peaks displayed in the following tables and figures can vary depending on many factors, for example, the effect of a selective orientation of a crystal on X-ray beam, the effect of coarse particles, the purity of a material to be analyzed or the crystallinity of a sample. The peak position can also be shifted based on the height variation of the sample. Further, different shifts are obtained according to the Bragg equation (nλ=2d sin θ) when measurement is carried out using a different wavelength, and such a different XRPD pattern obtained by using a different wavelength is also within the scope of the present invention.

Single crystal structure analysis (See Toshio SAKURAI, "X-sen Kozo Kaiseki no Tebiki (Guide to X-ray Structural Analysis)", published by Shokabo Co., Ltd. (1983), and Stout & Jensen, "X-Ray Structure Determination: A Practical Guide", Macmillan Co., New York (1968), etc.) is one of methods for determining a crystal, and it is possible to obtain crystallographic parameters in the crystal, atomic coordinates (values indicating a spatial positional relationship of each atom), and a three-dimensional structure model. Single crystal structure analysis is useful for identifying the structure of the crystal of the composite as in the present invention.

Raman Spectroscopy

A Raman spectrum shows vibrational features of molecules or a complex system. Its origin lies in inelastic collisions between molecules and photons as particles of light including light rays. The collision of molecules with photons leads to an exchange of energy, which results in a change in energy, which in turn changes the wavelength of the photons. That is, since the Raman spectrum are spectral line that are emitted when photons are incident on a target molecule and have an extremely narrow wavelength, a laser or the like is used as a light source. The wavelength of each Raman line is represented by a wavenumber shift from an incident light, which is a difference between an inverse of the wavelength of the Raman line and that of the incident light. The Raman spectrum is used for measuring a vibrational state of a molecule, which is determined by its molecular structure.

In general, since an absorption band ($cm^{-1}$) in a Raman spectrum may have an error within a range of ±2 $cm^{-1}$, the value of the absorption peak should be understood as including a numerical value within a range of about ±2 $cm^{-1}$. Therefore, the present invention encompasses not only crystals in which the peaks in the absorption bands in the Raman spectra completely coincide with each other, but also crystals in which the peaks in the absorption bands coincide with each other with an error of about ±2 cm$^{-1}$.

Infrared Absorption Spectroscopy (IR Method)

The infrared absorption spectroscopy is a method for measuring, for each wavenumber, a degree of absorption of infrared rays when the infrared rays pass through a sample. The infrared absorption spectrum is typically represented by a graph in which the horizontal axis represents a wavenumber and the vertical axis represents a transmittance or an absorbance. The wavenumber and transmittance (or absorbance) of the absorption peak can be read on a graph, and values calculated by a data processing device can be used. The infrared absorption spectrum is determined by the chemical structure of the substance. Therefore, absorption at various wavenumbers can be measured to confirm or quantify a substance. The discrimination of a crystal polymorph can be performed by comparing absorption bands of functional groups characteristic of crystal polymorphs, that is, a functional group mainly involved in a hydrogen bond in the crystal structure such as a C=O bond, an OH bond, and an NH bond, as well as other characteristic functional groups such as a C—X (halogen) bond, a C=C bond, and a C≡C bond. The absorption bands for characteristic functional group are selected from about 20 absorption peaks, more preferably about 10 absorption peaks, and most preferably about 5 absorption peaks corresponding to the characteristic functional groups. Typically, an absorption spectrum of a sample is measured in a wavenumber range of 4000 cm$^{-1}$ to 400 cm$^{-1}$. The absorption spectrum is measured under the same operating conditions as those when the resolution, the wavenumber scale, and the wavenumber accuracy of the apparatus were confirmed.

In general, since an absorption band (cm$^{-1}$) in infrared absorption spectroscopy may have an error within a range of ±2 cm$^{-1}$, the value of the absorption peak should be understood as including a numerical value within a range of about ±2 cm$^{-1}$. Therefore, the present invention encompasses not only crystals in which the peaks in the absorption bands in the infrared absorption spectroscopy completely coincide with each other, but also crystals in which the peaks in the absorption bands coincide with each other with an error of about ±2 cm$^{-1}$.

Examples of the method for measuring an infrared absorption spectrum include the potassium bromide tablet method, the solution method, the paste method, a liquid film method, the thin film method, the gas sample measurement method, the ATR method, and the diffuse reflection method. Among them, the attenuated total reflection (ATR) method is called the total reflection measurement method and is one of the reflection methods. In this method, a sample is brought into close contact with a surface of a prism made of a substance having a high refractive index such as KRS-5, light is incident on the prism at an angle equal to or larger than a critical angle, and light totally reflected at a boundary between the prism and the sample is measured to obtain an absorption spectrum. One of the conditions enabling the measurement by the ATR method is that the refractive index of the prism is larger than that of the sample, and thus it is necessary to change the material of the prism depending on the sample. In addition, as another condition, the prism and the sample must be in close contact with each other. Therefore, it is suitable for measurement of liquid, powder, plastic, soft rubber, and the like, and there is an advantage that measurement can be performed without chemically or physically treating the sample. On the other hand, the diffuse reflection method is a method of measuring a powder sample as it is without forming a potassium bromide tablet. When light is applied to a sample, light that is specularly reflected on the powder surface and exits to the outside and diffusely reflected light (scattered light) that enters the sample, repeats transmission and diffusion, and then exits to the surface are generated. In the diffuse reflection method, the latter is used to obtain an absorption spectrum.

Solid $^{13}$C-NMR (Nuclear Magnetic Resonance)

Solid state $^{13}$C-NMR is useful for specifying a crystal form because (i) the number of spectra coincides with the number of carbon atoms of a target compound, (ii) the chemical shift range is wider than that of $^1$H-NMR, (iii) a signal is sharper than that of solid state $^1$H-NMR, and (iv) even if an additive is contained, the chemical shift does not change when there is no interaction. Note that an observed chemical shift is expected to vary slightly depending on the particular spectrometer used and the analyst's sample preparation technique. The error range in the solid $^{13}$C-NMR spectrum is approximately ±0.5 ppm.

Differential Scanning Calorimetry (DSC)

DSC is one of the main measurement methods of thermal analysis, and is a method for measuring thermal properties of a substance as an aggregate of atoms and molecules.

A differential scanning calorimetry curve is obtained by measuring a change in heat quantity with respect to temperature or time of the pharmaceutically active ingredient by DSC and plotting the obtained data with respect to temperature or time. From the differential scanning calorimetry curve, it is possible to obtain information on the onset temperature when the pharmaceutically active ingredient is melted, the maximum value of the endothermic peak curve associated with melting, and enthalpy.

For DSC, it is known that the observed temperature may depend on temperature change rate as well as a sample preparation technique and specific equipment used. Thus, the "melting point" in DSC refers to onset temperature that is less susceptible to sample preparation techniques. An error range at the onset temperature obtained from the differential scanning calorimetry curve is approximately ±2° C. In recognition of the identity of crystals, not only the melting point but also the overall pattern is important, and the overall pattern may slightly vary depending on measurement conditions and a measuring instrument.

Thermogravimetry/Differential Thermal Analysis (TG/DTA)

TG/DTA is one of the main measurement methods of thermal analysis, and is a method for measuring weight and thermal properties of a substance as an aggregate of atoms and molecules.

TG/DTA is a method for measuring changes in weight and heat quantity of a pharmaceutically active ingredient with respect to temperature or time, and curves of TG (thermogravimetry) and DTA (differential thermal analysis) are obtained by plotting the obtained data with respect to temperature or time. From the TG/DTA curves, it is possible to obtain information on weight and heat quantity change regarding decomposition, dehydration, oxidation, reduction, sublimation, and evaporation of the pharmaceutically active ingredient.

For TG/DTA, it is known that the observed temperature and weight change may depend on temperature change rate as well as a sample preparation technique and specific equipment used. Thus, the "melting point" in TG/DTA refers to onset temperature that is less susceptible to sample preparation techniques. In recognition of the identity of crystals, not only the melting point but also the overall pattern is important, and the overall pattern may slightly vary depending on measurement conditions and a measuring instrument.

Moisture Sorption/Desorption Isotherm Measurement Method (DVS)

The moisture adsorption/desorption isotherm measurement is a measurement method for measuring the adsorption and desorption behavior of moisture by measuring a weight change in a solid as a measurement target under each relative humidity condition.

As a basic measurement method, based on the dry weight at 0% RH (relative humidity 0%), the relative humidity is increased every 5% or 10%, and after the weight is stabilized at each relative humidity, the amount of adsorbed water can be determined from the weight increase from the reference value. Similarly, the desorption amount of water can be measured by decreasing the relative humidity every 5% or 10% from 100% RH.

By plotting the value of the weight change at each relative humidity, an adsorption/desorption isotherm can be obtained. From this result, it is possible to consider a phenomenon of adsorption and desorption of adhering moisture at each humidity. In addition, when an anhydride crystal and a hydrate crystal mutually undergo crystal transition due to humidity, it is possible to calculate the humidity at which the crystal transition occurs and the amount of crystal water.

Sorption and desorption of adhering water and crystal water are affected by particle size, crystallinity, crystal habit, and the like, so that the measurement results may slightly change.

The pharmaceutical composition containing a crystal of the present invention is very useful as a therapeutic agent or a prophylactic agent for chronic cough.

The crystal of the present invention can be administered to a human patient by itself, or can be administered as a pharmaceutical composition in which the crystal is mixed with an appropriate carrier or excipient. Techniques for drug formulation and administration can be appropriately selected and used in combination with pharmaceutical formulations and techniques known to those skilled in the art.

Examples of administration route of the crystal of the present invention or the pharmaceutical composition containing the crystal can include, but is not limited to, oral, rectal, transmucosal, or intestinal administration, or intramuscular, subcutaneous, intraspinal, intrathecal, direct intraventricular, intravenous, intravitreal, intraperitoneal, intranasal, and intraocular, injection. A preferred route of administration is oral administration.

The pharmaceutical composition of the present invention can be produced by a method well known in the art, for example, a process of conventional mixing, dissolving, granulating, sugar-coating, powdering, emulsifying, encapsulating, enclosing, or lyophilizing.

The crystal of the present invention or the pharmaceutical composition containing the crystal can be administered by injection using an aqueous solution, preferably a physiologically compatible buffer such as Ringer's solution or physiological saline.

The crystal of the present invention or the pharmaceutical composition containing the crystal can be administered transmucosally using a penetrant suitable for a barrier to be permeated. As the penetrant, one generally known in the art can be used.

The crystal of the present invention or the pharmaceutical composition containing the crystal may be combined with a pharmaceutically acceptable carrier well known in the art so as to be orally administered. The carrier allows the crystal of the invention to be administered as tablets, pills, lozenges, sugar-coated tablet, capsules, solution, gel, syrups, or suspensions. Pharmaceutical compositions for oral administration can be made by adding solid excipients and, if desired, other suitable auxiliaries, followed by grinding the resulting mixture and processing the mixture of granules to obtain tablets or sugar-coated tablet cores.

Useful excipients are, in particular, fillers such as sugars, including lactose, sucrose, mannitol, or sorbitol, for example, cellulose preparations such as corn starch, wheat starch, rice starch, and potato starch, gelatin, gum tragacanth, methyl cellulose, hydroxypropylmethylcellulose, and/or sodium carboxymethylcellulose. If necessary, a disintegrant such as agar or alginic acid can be added. A salt such as sodium alginate can also be used.

Examples of the pharmaceutical composition that can be used for oral administration include push-fit capsules made of gelatin, and sealed capsules made of gelatin and a plasticizer such as glycerol or sorbitol. The push-fit capsule can contain an active ingredient mixed with a filler such as lactose, a binder such as starch, and/or a lubricant such as talc or magnesium stearate.

The pharmaceutical composition can also contain a suitable solid or a gel phase carrier or excipient. Examples of such a carrier or excipient include calcium carbonate, calcium phosphate, various sugars, starch, cellulose derivatives, gelatin, and polymers such as polyethylene glycol.

For the crystals of the invention or pharmaceutical compositions thereof, a therapeutically effective amount can first be estimated from cell culture assay. Then, a dosage of a large amount can then be formulated for use in animal models to achieve a circulating concentration range that covers IC 50 (that is, a concentration of the crystal of the present invention or pharmaceutical composition thereof with which half maximal inhibition of PK activity is achieved) as determined in cell culture. Such information can then be used to more accurately determine a useful amount of the same in humans.

Therapeutic effects of the crystal of the present invention or the pharmaceutical composition thereof can be measured by a standard pharmaceutical method in cell culture or experimental animals. For example, evaluation may be performed according to a biological test method described in Patent Document 9. The data obtained from these cell culture assays and animal experiments can be used to formulate a range of dosages for use in humans. The dosage can be varied depending on the form of administration used and the route of administration utilized. The exact administration route of formulation and dosage can be selected by the individual physician in view of the patient's condition.

It is also an aspect of the present invention that the crystals of the present invention or pharmaceutical compositions thereof can be combined with other agents for the treatment of diseases and disorders.

The present invention provides an anhydride crystal or a hydrate crystal of the compound represented by Formula (I). The crystalline solid has at least one of the following characteristics:

(1) having good stability against heat, humidity, solvent, light and the like, and high storage stability;
(2) having good coloring stability;
(3) having good solubility in water or organic solvents;
(4) having a high dissolution rate with respect to water or organic solvents;
(5) having high purity;
(6) having a low rate of residual organic solvent;
(7) having excellent operability in filtration, centrifugation, and formulation;
(8) having a small specific volume;
(9) being hardly charged;
(10) being produced at a high yield under conditions with reduced loads on the environment, and being able to be mass-produced;
(11) being useful as a pharmaceutically active ingredient for an injection, or an active material for the production thereof;
(12) being controllable to a pH range suitable for intravenous injection without vascular pain, thereby being advantageous for liquid amount control, reduction of excipients, etc. at the time of formulation;
(13) having good fluidity; and
(14) having a low Compressibility index (%).

In particular, the crystalline solid of the present invention has high stability even in a wide humidity range (for example, 25 to 99% RH or the like) and a severe environment (for example, under high humidity).

The meaning of each term used in the present specification will be described below. Unless otherwise specified, each term is used in the same meaning when used alone or in combination with another term.

The term "consisting of" means having only the components.

The term "including" means being not limited to the components, but not excluding elements that are not described.

Hereinafter, the present invention will be described with reference to embodiments. It is to be understood that throughout the specification, the singular forms of expression also include the concept of the plural forms thereof, unless otherwise stated. Thus, it is to be understood that the singular article (for example, in English, "a", "an", "the", and the like) also includes the plural concept thereof unless otherwise stated.

It is also to be understood that the terms used in the present specification are used in the sense commonly used in the art, unless otherwise stated. Thus, unless defined otherwise, all technical and scientific terms used in the present specification have the same meanings as those commonly understood by those skill in the art to which this invention belongs. In case of conflict, the present specification (including definitions) will control.

The term "halogen" encompasses a fluorine atom, a chlorine atom, a bromine atom, and an iodine atom. In particular, a fluorine atom and a chlorine atom are preferable.

The term "alkyl" encompasses a linear or branched hydrocarbon group having 1 to 15 carbon atoms, preferably 1 to 10 carbon atoms, more preferably 1 to 6 carbon atoms, and still more preferably 1 to 4 carbon atoms. Examples thereof include methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, and n-decyl.

Preferred embodiments of the "alkyl" include methyl, ethyl, n-propyl, isopropyl, n-butyl, isobutyl, sec-butyl, tert-butyl, and n-pentyl. More preferred embodiments include methyl, ethyl, n-propyl, isopropyl, and tert-butyl.

Examples of the "C1-C4 alkyl" include methyl, ethyl, n-propyl, isopropyl, n-butyl, isobutyl, sec-butyl, and tert-butyl.

The present invention includes a step of producing a compound represented by Formula (IV):

[Chemical formula 33]

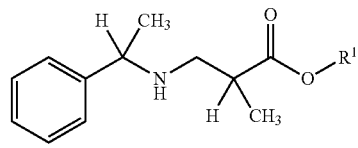

(IV)

wherein $R^1$ is C1-C4 alkyl,
or a salt thereof,
characterized by causing a reaction between a compound represented by Formula (II):

[Chemical formula 34]

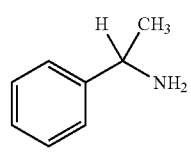

(II)

or a salt thereof,
and a compound represented by Formula (III):

[Chemical formula 35]

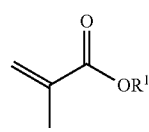

(III)

wherein $R^1$ is C1-C4 alkyl,
or a salt thereof,
under the presence of one or more additives selected from the group consisting of lithium chloride, calcium chloride, magnesium chloride, lithium bromide, p-toluenesulfonic acid, methanesulfonic acid, and trifluoromethanesulfonic acid.

The compound represented by Formula (II) or a salt thereof and the compound represented by Formula (III) or a salt thereof can be produced according to a known method from commercially available reagents, or a commercially available product can be used as these compounds and salts.

The solvent is not particularly limited as long as the reaction is not inhibited, but methanol, ethanol, isopropyl alcohol, t-butanol, or a mixed solvent thereof can be used as the solvent. For example, methanol can be used.

Regarding a reaction temperature, the reaction is usually carried out in a range of room temperature to a temperature at which the solvent is refluxed. For example, the reaction can be performed in a range of −10° C. to a temperature at which the solvent is refluxed. For example, it can be performed at 80° C.

The reaction time is 1 to 20 hours, for example, 5 to 7 hours.

The use amount of the compound represented by Formula (III) with respect to the compound represented by Formula (II) can be usually 1.0 to 10.0 equivalents, for example, 2.0 to 4.0 equivalents, for example, 3.0 equivalents.

As an additive, lithium chloride, calcium chloride, magnesium chloride, lithium bromide, p-toluenesulfonic acid, methanesulfonic acid, trifluoromethanesulfonic acid, or the like can be used. A plurality of these additives can be selected and used simultaneously.

The use amount of the additive with respect to the compound represented by Formula (II) can be usually 0.1 to 5.0 equivalents, for example, 1.0 to 2.0 equivalents, for example, 1.0 to 1.5 equivalents.

The present invention includes a step of producing a p-toluenesulfonic acid salt of a compound represented by Formula (IV-A):

[Chemical formula 36]

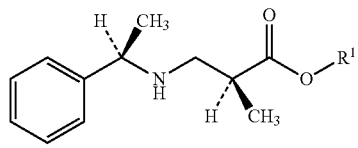

(IV-A)

wherein $R^1$ is C1-C4 alkyl,
characterized by:
adding p-toluenesulfonic acid to a compound represented by Formula (IV):

[Chemical formula 37]

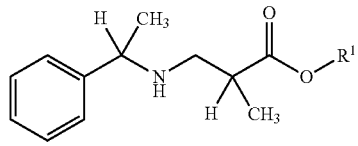

(IV)

wherein $R^1$ is C1-C4 alkyl,
or a salt thereof.

The use amount of p-toluenesulfonic acid monohydrate (or aqueous p-toluenesulfonic acid solution) with respect to the compound represented by Formula (II) can be usually 0.5 to 2.0 equivalents, for example, 0.8 to 1.0 equivalents.

The present invention includes a step of producing a ½ sulfuric acid salt of a compound represented by Formula (V):

[Chemical formula 38]

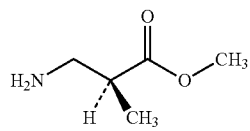

(V)

characterized by:
subjecting a p-toluenesulfonic acid salt of a compound represented by Formula (IV-B):

[Chemical formula 39]

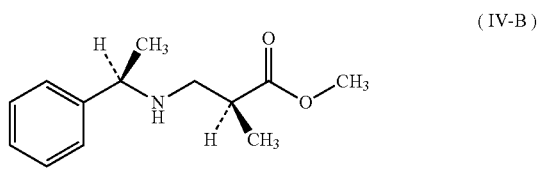

(IV-B)

to a hydrogenolysis reaction; and
adding sulfuric acid thereto.

The compound represented by Formula (IV-B) can be produced according to the above-described step.

The solvent is not particularly limited as long as the reaction is not inhibited, but methanol, ethanol, 1-propanol, isopropyl alcohol, t-butanol, tetrahydrofuran, or a mixed solvent thereof can be used. For example, methanol can be used.

Regarding a reaction temperature, the reaction is usually carried out in a range of room temperature to a temperature at which the solvent is refluxed. For example, the reaction can be performed in a range of room temperature to a temperature at which the solvent is refluxed. For example, it can be performed at 30 to 50° C.

The reaction time is 30 minutes to 20 hours, for example, 1 to 3 hours.

As a hydrolysis reaction catalyst, palladium carbon, palladium hydroxide, palladium black, or the like can be used.

The use amount of the hydrolysis reaction catalyst with respect to the compound represented by Formula (IV-B) can be usually 0.01 to 1 w/w, for example, 0.1 to 0.3 w/w.

The use amount of concentrated sulfuric acid with respect to the compound represented by Formula (IV-B) can be usually 0.01 to 5.0 equivalents, for example, 0.3 to 0.4 equivalents.

The present method includes a step of producing a compound represented by Formula (I):

[Chemical formula 40]

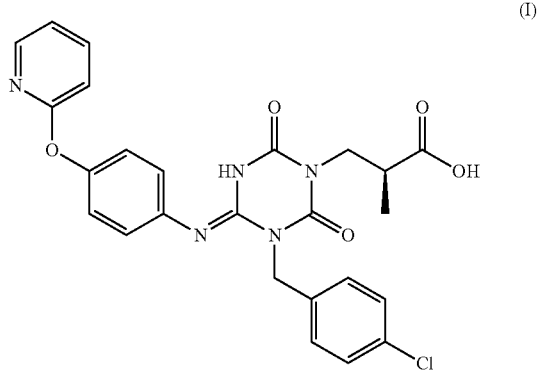 [SMILES: C[C@@H](Cn1c(=O)[nH]/c(=N\c2ccc(Oc3ccccn3)cc2)n(Cc2ccc(Cl)cc2)c1=O)C(=O)O]

(I)

or a salt thereof,
characterized by:
subjecting the compound represented by Formula (VI):

[Chemical formula 41]

(VI)

wherein $R^1$ is C1-C4 alkyl,
or the salt thereof,
to a hydrolysis reaction under the presence of one or more solvents selected from the group consisting of isopropyl alcohol, tetrahydrofuran, and t-butanol.

The compound represented by Formula (VI) can be produced according to the above-mentioned steps and the methods described in Patent Documents 6, 7, 8 and 9.

The solvent is not particularly limited as long as the reaction is not inhibited, but isopropyl alcohol (2-propanol), tetrahydrofuran, and t-butanol, or a mixed solvent thereof can be used. For example, isopropyl alcohol (2-propanol) can be used.

Regarding a reaction temperature, the reaction is usually carried out in a range of −10° C. to a temperature at which the solvent is refluxed. For example, it can be performed at 30° C. to 40° C.

The reaction time is 0.1 to 20 hours, for example, 1 to 5 hours.

As a base, sodium hydroxide, potassium hydroxide, lithium hydroxide, or the like can be used. For example, sodium hydroxide can be used.

The use amount of a base with respect to the compound represented by Formula (VI) can be usually 2.0 to 5.0 equivalents, for example, 2.0 to 3.0 equivalents.

EXAMPLES

The present invention will be described in more detail by the following examples. These do not limit the present invention. For numerical values (For example, the amount, temperature, and the like), some error and deviation should be considered.

Unless otherwise noted, "%" means % by weight of the component and % by weight of the total weight of the composition, and "pressure" means a pressure at or near atmospheric pressure.

Measurement of Powder X-Ray Diffraction Pattern

Powder X-ray diffraction measurement of a crystal obtained in each Example was performed according to the powder X-ray diffraction measurement method described in "General Tests, Processes, and Apparatus" of Japanese Pharmacopoeia. The measurement conditions are shown below.

Method 1

Apparatus

SmartLab manufactured by Rigaku Corporation

Operation Method

Measurement method: reflection method
Used wavelength: CuKα ray
Tube current: 200 mA
Tube voltage: 45 kV
Sample plate: glass
Incident angle of X-ray: 2.5°
Sampling width: 0.02°
Detector: HyPix-3000 (two-dimensional detection mode)

Method 2

Apparatus

D-8 Discover manufactured by Bruker Corporation

Operation Method

Measurement method: reflection method
Used wavelength: CuKα ray
Tube current: 40 mA
Tube voltage: 40 kV
Sample plate: aluminum
Incident angle of X-ray: 3° and 12°

Method 3

D-8 Discover manufactured by Bruker Corporation

Operation Method

Measurement method: reflection method
Used wavelength: CuKα ray
Tube current: 40 mA
Tube voltage: 40 kV
Sample plate: aluminum
Incident angle of X-ray: 3°

Measurement of Raman Spectrum

A Raman spectrum of a crystal obtained in each Example was measured. The measurement conditions are shown below.

Method 1

Measurement apparatus: LabRAM ARAMIS (manufactured by HORIBA Jobin Yvon SAS)
Measurement method: micro laser Raman spectroscopy
Laser wavelength: 633 nm (He—Ne laser)
Diffraction grating: 600 grooves/mm
Detector: CCD detector
Objective lens: 20×(NA 0.25)
Number of integrations: 5 times
Exposure time: 5 seconds Method 2

Measuring instrument: RAMANTouch Vis2-NIR-SNU (manufactured by Nanophoton Corporation)
Measurement method: micro laser Raman spectroscopy
Laser wavelength: 532 nm
Diffraction grating: 1200 grooves/mm
Detector: CCD detector
Objective lens: 20×(NA 0.45)
Number of integrations: 1 time
Exposure time: 3 seconds Measurement of Differential Scanning Calorimetry (DSC)

A DSC of a crystal obtained in each Example was measured. About 4.199 mg of a sample was weighed in an aluminum pan, and the weight was measured by simple sealing. The measurement conditions are shown below. Incidentally, an error may occur within a range of ±2° C. in the measurement by differential scanning calorimetry (DSC).
Apparatus: TA Instruments Discovery
Measurement temperature range: 0° C. to 220° C.
Heating rate: 10° C./min
Atmosphere: $N_2$ 50 mL/min NMR Measurement When NMR data are shown, all measured peaks may not be described.

HPLC Measurement

Method A

Column: XBridge C18, φ 4.6×150 mm, 3.5 μm (Waters)
Column oven: 40° C.
Flow rate: 1.0 mL per minute
UV detection wavelength: 254 nm
Mobile phase A: 0.1% trifluoroacetic acid aqueous solution
Mobile phase B: acetonitrile for liquid chromatography
The gradient program is shown in Table 1.

TABLE 1

| Time after injection (min) | Mobile phase A (vol %) | Mobile phase B (vol %) |
| --- | --- | --- |
| 0-4 | 85 | 15 |
| 4-10 | 85 → 60 | 15 → 40 |
| 10-13 | 60 → 10 | 40 → 90 |
| 13-17 | 10 | 90 |
| 17-17.01 | 10 → 85 | 90 → 15 |
| 17.01-27 | 85 | 15 |

Method B

Column: CHIRALPACK AS-RH, φ 4.6×150 mm, 5 μm (Daicel Chemical Industries, Ltd.)
Column oven: 35° C.
Flow rate: 1.0 mL per minute
UV detection wavelength: 254 nm
Mobile phase A: purified water for liquid chromatography
Mobile phase B: acetonitrile for liquid chromatography
The gradient program is shown in Table 2.

TABLE 2

| Time after injection (min) | Mobile phase A (vol %) | Mobile phase B (vol %) |
| --- | --- | --- |
| 0-14 | 80 | 20 |
| 14-18 | 80 → 10 | 20 → 90 |
| 18-24 | 10 | 90 |
| 24-24.01 | 10 → 80 | 90 → 20 |
| 24.01-30 | 80 | 20 |

Method C

Column: CHIRALPACK IC, φ 4.6×250 mm, 5 μm (Daicel Chemical Industries, Ltd.)
Column oven: 35° C.
Flow rate: 1.0 mL per minute
UV detection wavelength: 262 nm
Mobile phase: 0.1% formic acid aqueous solution/acetonitrile mixture solution for liquid chromatography (3:2)

Method D

Column: Cadenza CD-C18, φ 3.0×150 mm, 3 μm
Column oven: 50° C.
Flow rate: 0.55 mL per minute
UV detection wavelength: 262 nm
Mobile phase A: 0.1% TFA aqueous solution
Mobile phase B: Acetonitrile
The gradient program is shown in Table 3.

TABLE 3

| Time (min) | Mobile phase A (%) | Mobile phase B (%) |
| --- | --- | --- |
| 0 | 80 | 20 |
| 1 | 80 | 20 |
| 10 | 45 | 55 |
| 15 | 45 | 55 |
| 20 | 10 | 90 |
| 25 | 10 | 90 |
| 25.01 | 80 | 20 |
| 30 | 80 | 20 |

The retention time of HPLC should be understood as including some errors.

Measurement of TG/DTA

About 4.4 mg of the crystal obtained in Example 7 was weighed, was put in an aluminum pan, and was measured in an open system. The measurement conditions are as follows.
Apparatus: Hitachi High-Technologies TG/DTA STA7200RV
Measurement temperature range: room temperature to 300° C.
Heating rate: 10° C./min Measurement and Analysis Method of Single Crystal Structure Analysis Measurement conditions and analysis methods for single crystal structure analysis are shown below.

Apparatus

XtaLAB P 200 MM007 manufactured by Rigaku Corporation

Measurement Conditions

Measurement temperature: 25° C.

Used wavelength: CuKα ray (λ=1.5418 Å)

Software: CrysAlisPro 1.171.39.46e (Rigaku Oxford Diffraction, 2018)

Data Processing

Software: CrysAlisPro 1.171.39.46e (Rigaku Oxford Diffraction, 2018)

The data were subjected to Lorentz, and polarization correction, and absorption correction.

Crystal Structure Analysis

The phase determination was performed using the direct method program ShelXT (Sheldrick, G. M., 2015), and was refined by the full-matrix least squares method using ShelXL (Sheldrick, G. M., 2015). All temperature factors of non-hydrogen atoms were refined with anisotropy. A hydrogen atom H5 on an oxygen O5 was derived from a difference Fourier map and refined. The remaining hydrogen atoms were introduced by calculation using default parameters of ShelXL and treated as riding atoms. All hydrogen atoms were refined with isotropic parameters. R1 (I>2.00s(I)) was 0.0470, and it was confirmed from the final difference Fourier that there was neither lacking nor erroneous electron density.

PLUTON (Spek, 1991)/ORTEP (Johnson, 1976) was used to plot FIGS. 7 and 8 (50% PROBABILITY level).

Example 1

Synthesis of Compound (3)

[Chemical formula 42]

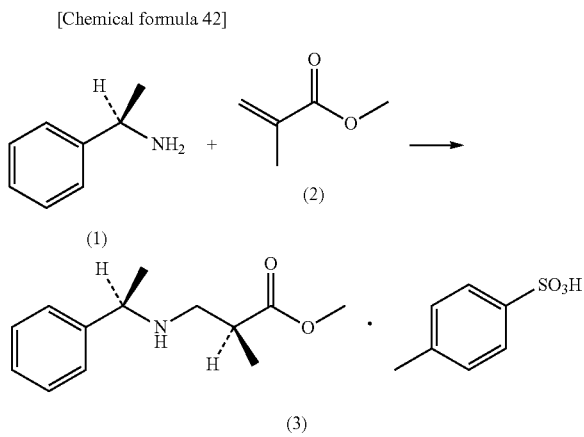

[1] Synthesis of Compound (3)

Methanol (20 mL) and methyl methacrylate (2) (49.64 g, 495.8 mmol) were added to (R)-(+)-1-phenylethylamine (1) (20.01 g, 165.1 mmol) at room temperature. After cooling to −10° C., lithium chloride (7.07 g, 167 mmol) was added. The reaction solution was heated to 80° C. and stirred for 6 hours. The reaction solution was cooled to 25° C., a 9.1% sodium chloride aqueous solution (77.03 g) was added thereto, and an aqueous layer was removed by liquid separation. Toluene (61.04 g) was added to the obtained aqueous layer at room temperature, and an aqueous layer was removed by liquid separation. The obtained two organic layers were combined, toluene (16.99 g) was added, and the mixture was concentrated under reduced pressure at 50° C.

Ethanol (16.00 g) and p-toluenesulfonic acid monohydrate (28.91 g, 152.0 mmol) were mixed together, to give an ethanol solution (44.91 g) of p-toluenesulfonic acid.

Toluene (155.91 g) was added to the concentrate prepared above. The ethanol solution (5.88 g) of p-toluenesulfonic acid prepared above and a slurry of seed crystal (19.95 mg, 0.05070 mmol) in toluene (63 μL) were added to the mixture at room temperature to give a slurry of the compound (3). Remaining ethanol solution (39.93 g) of the p-toluenesulfonic acid prepared above was added to the obtained slurry, and ethanol (10 mL) was added thereto. The resulting mixture was stirred for 2 hours and allowed to stand overnight. The mixture was cooled to 0° C. and stirred for 2 hours, and a solid was collected by filtration, to give the compound (3) (20.75 g, 31.9%) as a crude product.

Toluene (1.92 g), ethyl acetate (21.70 g) and methanol (2.90 g) were added to a part (5.00 g) of the crude product of the compound (3), and the mixture was stirred at 50° C. for 3 hours. The mixture was cooled to 0° C., and a solid was collected by filtration, whereby the compound (3) (4.65 g) was obtained.

Elemental analysis: C, 61.22%, H, 7.09%, N, 3.56%, S, 8.12%

$^1$H-NMR (DMSO-d6) δ ppm: 1.12 (d, J=7.0 Hz, 3H), 1.55 (br d, J=6.7 Hz, 3H), 2.29 (s, 3H), 2.50 (s, 2H), 2.83 (br dd, J=13.2 Hz, 6.9 Hz, 1H), 2.90 (m, 2H), 3.62 (s, 3H), 7.13 (m, 2H), 7.47 (m, 7H)

[2] Synthesis of Seed Crystal of Compound (3)

(R)-(+)-1 phenylethylamine (1) (2.00 g, 16.5 mmol), methanol (1.59 g), methyl methacrylate (2) (4.97 g, 49.6 mmol) and lithium chloride (0.70 g, 17 mmol) were mixed at room temperature, and the mixture was heated to 80° C. and stirred for 4 hours. The reaction solution was cooled to 25° C., a 9.1% sodium chloride aqueous solution (7.70 g) was added thereto, and an aqueous layer was removed by liquid separation. After toluene (5.21 g) was added to the organic layer obtained, a methanol solution (4.46 g) of p-toluenesulfonic acid prepared by dissolving p-toluenesulfonic acid monohydrate (2.88 g, 15.1 mmol) in methanol (1.58 g) was added thereto. This reaction solution was added to toluene (6.94 g) cooled to 0° C., and the mixture was stirred at 0° C. for 30 minutes. The precipitated solid was collected by filtration to obtain a seed crystal (1.60 g, 24.6%) of the compound (3).

Example 1-1

Synthesis of Compound (3)

[Chemical formula 43]

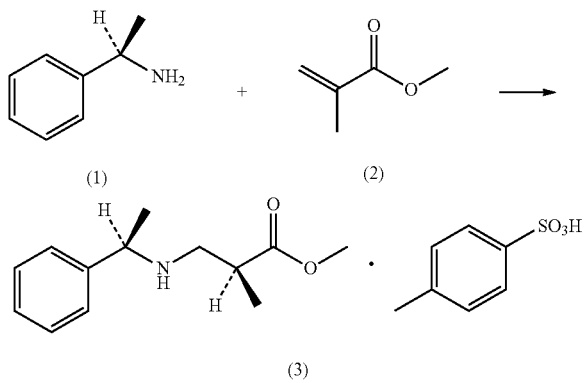

At room temperature, p-toluenesulfonic acid monohydrate (1.57 g, 8.25 mmol) and methyl methacrylate (2, 49.57 g, 495.1 mmol) were added to (R)-(+)-1 phenylethylamine (1) (20.00 g, 165.0 mmol), and the mixture was heated to 99° C. and stirred at 99° C. for 16 hours. After the mixture was cooled to 25° C., methanol (8 mL) was added thereto, and the this was mixed with a solution of p-toluenesulfonic acid prepared by dissolving p-toluenesulfonic acid monohydrate (27.31 g, 143.6 mmol) in ethyl acetate (40 mL) and methanol (4 mL). Ethyl acetate (100 mL) was added to this reaction solution at 25° C., and the precipitated solid was collected by filtration to obtain the compound (3) (28.14 g) as a crude product.

Ethyl acetate (15 mL) and methanol (30 mL) were added to the crude product (28.14 g) of the compound (3), and the mixture was heated to 60° C. and then cooled to 40° C. Slurry of seed crystal (20.0 mg, 0.308 mmol) of the compound (3) in ethyl acetate (60 μL) was added to the foregoing mixture at 40° C. After the obtained slurry was stirred at 40° C. for 30 minutes, then cooled to 22° C., ethyl acetate (218 mL) was added thereto, and the mixture was cooled to 0° C. and stirred for 1 hour. The precipitated solid was collected by filtration to obtain the compound (3) (22.29 g, 34.32%).

Example 2

Synthesis of Compound (4)

[Chemical formula 44]

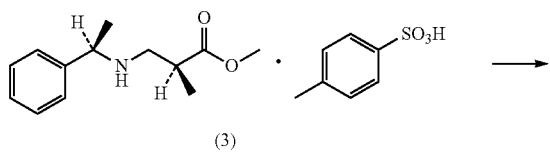

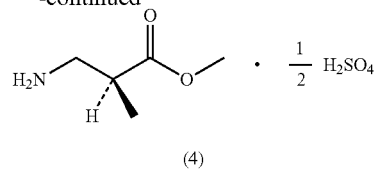

Toluene (95.26 g) and water (44.00 g) were added to the compound (3) (22.00 g, 55.91 mmol) so that the compound (3) was suspended, a 8% sodium hydroxide aqueous solution (27.54 g) and water (4.40 g) were added thereto, and an aqueous layer was removed by liquid separation. Water (11.00 g) was added to the obtained organic layer, and an aqueous layer was removed by liquid separation. An operation of concentration of the resulting organic layer under reduced pressure at 50° C. and adding methanol was repeated so that the solvent was replaced with methanol. Concentrated sulfuric acid (2.04 g, 19.8 mmol), 10% palladium on carbon (2.20 g, about 40% wet) and methanol (17.41 g) were added to the obtained concentrated solution. The reaction solution was heated to 40° C. and stirred for 90 minutes under a hydrogen atmosphere. Palladium on carbon was removed by filtration, and methanol (52.24 g) and concentrated sulfuric acid (0.67 g, 6.5 mmol) were added to the obtained filtrate. The operation of adding acetonitrile to the obtained reaction solution and concentration under reduced pressure was repeated so that the solvent was replaced with acetonitrile, and the reaction solution was cooled to 0° C. The precipitated solid was collected by filtration to obtain the compound (4) (8.58 g, 92.3%).

Elemental analysis: C, 35.72%, H, 7.18%, N, 8.55%, S, 9.63%

$^1$H-NMR (DMSO-d6) δ ppm: 1.10 (d, J=7.1 Hz, 3H), 2.62 (m, 1H), 2.75 (dd, J=12.7H, 5.9 Hz, 1H), 2.89 (dd, J=12.7 Hz, 7.3 Hz, 1H), 3.63 (s, 3H)

(Reference Example 1) Synthesis of Compound (5)

[Chemical formula 45]

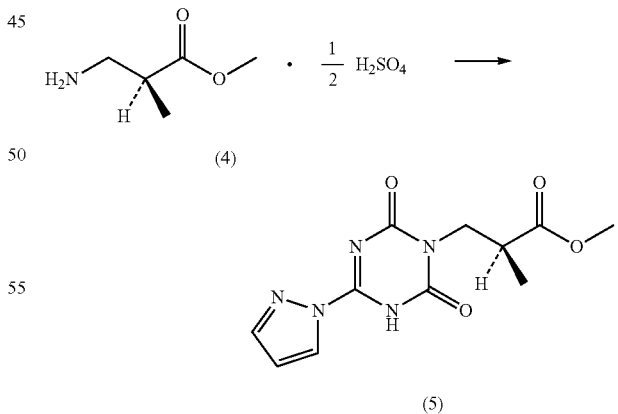

The compound (4) (19.00 g, 114.3 mmol) was suspended in acetonitrile (45.00 g). At 2° C., 1,8-diazabicyclo[5.4.0]-7-undecene (19.10 g, 125.5 mmol) and acetonitrile (3.00 g) were added thereto, and the mixture was stirred at 2° C. for 30 minutes. The reaction solution was added, at 2° C., to a slurry obtained by suspending N,N-carbonyldiimidazole (21.30 g, 131.4 mmol) in acetonitrile (75.00 g). Acetonitrile (15.00 g) was added to the reaction solution, and the mixture was stirred at 2° C. for 1 hour and 22 minutes. At 2° C., 1,8-diazabicyclo[5.4.0]-7-undecene (17.40 g, 114.3 mmol) and acetonitrile (3.00 g) were added to the reaction solution, and the mixture was cooled to 1° C. To the reaction solution, 1H-pyrazole-1-carboxamidine hydrochloride (16.80 g, 114.6 mmol) and acetonitrile (3.00 g) were added. The reaction solution was heated to 60° C. and stirred for 2 hours and 10 minutes. The reaction solution was cooled to 20° C. At 2° C., 1,8-diazabicyclo[5.4.0]-7-undecene (27.80 g, 182.6 mmol) and acetonitrile (3.00 g) were added to the reaction solution, and the mixture was cooled to −10° C. To the reaction solution, N,N-carbonyldiimidazole (29.70 g, 183.2 mmol) and acetonitrile (3.00 g) were added. The reaction solution was stirred at 2° C. for 1 hours and 20 minutes. To the reaction solution, methanol (7.50 g), acetic acid (4.80 g, 79.9 mmol), and acetonitrile (3.00 g) were added at 2° C. The reaction solution was concentrated under reduced pressure at 50° C. N, N-Dimethylacetamide (27.00 g) was added to the obtained concentrated solution, the mixture was cooled to 10° C., and 17% aqueous sulfuric acid (204.1 g) and water (19.00 g) were added thereto. To the reaction solution, 17% aqueous sulfuric acid (31.30 g) and water (2.50 g) were added at 25° C., and the mixture was stirred for 1 hour and 48 minutes. The reaction solution was concentrated under reduced pressure at 50° C. Water (190 mL) was added to the obtained concentrated solution and cooled to 2° C., and then 17% aqueous sulfuric acid (3.30 g) and water (1.30 g) were added thereto. The reaction solution was stirred at 2° C. for 1 hour and 15 minutes, and the precipitated solid was collected by filtration to obtain a compound (5) (27.13 g, 85.0%).

$^1$H-NMR (CDCl$_3$) δ ppm: 1.24 (d, J=7.1 Hz, 3H), 3.02 (m, 1H), 3.68 (s, 3H), 4.02 (dd, J=13.4 Hz, 6.3 Hz, 1H), 4.24 (dd, J=13.3 Hz, 8.4 Hz, 1H), 6.60 (dd, J=2.8 Hz, 1.6 Hz, 1H), 7.85 (d, J=1.6 Hz, 1H), 8.48 (dd, J=2.9 Hz, 0.6 Hz, 1H), 9.70 (brs, 1H).

(Reference Example 2) Synthesis of Compound (8)

(14.10 g, 129.2 mmol) and N-methyl-2-pyrrolidone (16.00 g) were added thereto. The reaction solution was heated to 100° C., and 2-bromopyridine (6) (19.50 g, 123.4 mmol) and N-methyl-2-pyrrolidone (4.00 g) were added thereto. The reaction solution was stirred at 115° C. for 8 hours and 20 minutes, and was cooled to 50° C. Water (29.00 g) was added to the reaction solution at 50° C., the reaction solution was cooled to 25° C., and water (107.00 g) was added thereto. A seed crystal (8, 20 mg) of the compound (8) and water (195 mg) were added to the reaction solution, and the mixture was stirred at 20° C. for 50 minutes. Water (156.00 g) was added to the reaction solution at 25° C., the reaction solution was cooled to 5° C., and was stirred for 1 hour and 30 minutes. The precipitated solid was collected by filtration to obtain the compound (8) (17.81 g, 77.5%).

$^1$H-NMR (CDCl$_3$) δ ppm: 3.60 (s, 2H), 6.69-6.73 (m, 2H), 6.83 (ddd, J=8.4 Hz, 0.8 Hz, 0.8 Hz, 1H), 6.92-6.96 (m, 3H), 7.63 (ddd, J=8.0 Hz, 7.2 Hz, 2.0 Hz, 1H), 8.18 (ddd, J=5.2 Hz, 2.0 Hz, 0.8 Hz, 1H)

[2] Synthesis of Seed Crystal of Compound (8)

Sodium tert-butoxide (3.20 g, 33.3 mmol) was suspended in N-methyl-2-pyrrolidone (16.42 g), and 4-aminophenol (7) (3.64 g, 33.4 mmol) and N-methyl-2-pyrrolidone (4.12 g) were added thereto. The reaction solution was heated to 100° C., and 2-bromopyridine (6) (5.01 g, 31.7 mmol) and N-methyl-2-pyrrolidone (1.10 g) were added thereto. The reaction solution was stirred at 115° C. for 6 hours, and sodium tert-butoxide (1.07 g, 11.1 mmol) was added thereto. The mixture was stirred at 115° C. for 2 hours and 35 minutes, and then cooled to 50° C. Water (7.50 g) was added to the reaction solution at 50° C., and thereafter the reaction solution was cooled to 25° C. Water (67.54 g) was added thereto, and was cooled to 1° C. for crystallization. After the obtained slurry was stirred at 5° C. for 30 minutes, the precipitated solid was collected by filtration to obtain a seed crystal (3.84 g, 65.2%) of the compound (8).

(Reference Example 3) Synthesis of Compound (9)

[Chemical formula 46]

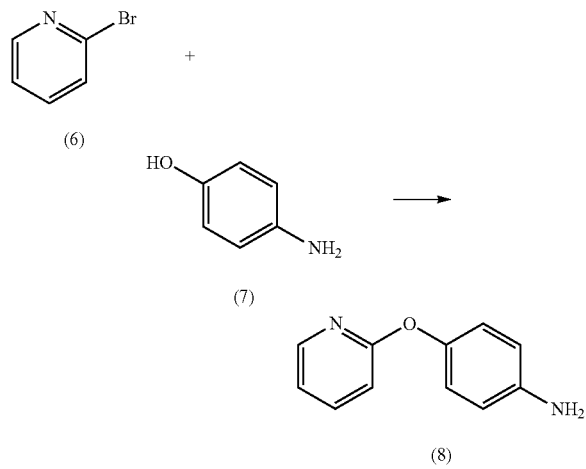

[1] Synthesis of Compound (8)

Sodium tert-butoxide (12.50 g, 130.1 mol) was suspended in N-methyl-2-pyrrolidone (64.00 g), and 4-aminophenol (7)

[Chemical formula 47]

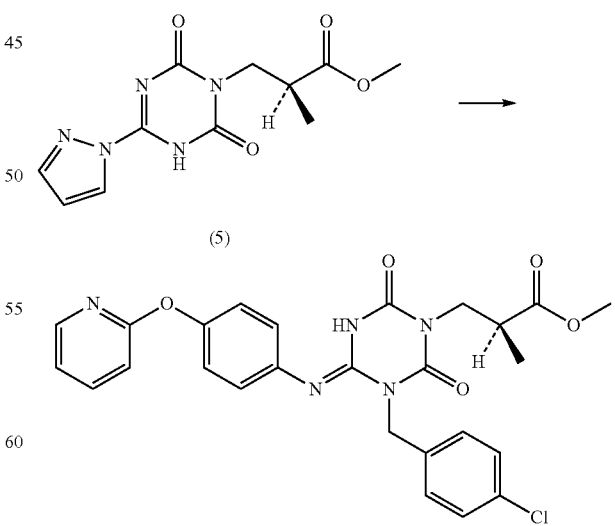

[1] Synthesis of Compound (9)

Sodium bromide (4.1 g, 39.9 mmol) and N, N-dimethylacetamide (27.70 g) were added to the compound (5) (10.13 g, 36.27 mmol). N, N-diisopropylethylamine (5.16 g, 39.9 mmol) and N, N-dimethylacetamide (0.96 g) were added to the reaction solution, and the mixture was heated to 75° C. To the reaction solution, an N,N-dimethylacetamide solution of 4-chlorobenzyl chloride prepared by dissolving 4-chlorobenzyl chloride (6.43 g, 39.9 mmol) in N,N-dimethylacetamide (9.56 g) was added at 75° C., and N,N-dimethylacetamide (9.56 g) was added. The reaction solution was stirred at 75° C. for 5 hours and 15 minutes. The reaction solution was cooled to 25° C., acetic acid (0.65 g, 11 mmol) was added thereto, and the mixture was heated to 40° C. To the reaction solution, an N,N-dimethylacetamide solution of the compound (8) prepared by dissolving the compound (8) (7.43 g, 39.9 mmol) in N, N-dimethylacetamide (9.55 g) was added, and N, N-dimethylacetamide (9.55 g) was added. The reaction solution was stirred at 40° C. for 3 hours, and was cooled to room temperature. To the reaction solution, acetone (27.94 g) and water (35.46 g) were added. A seed crystal (10.13 mg) of the compound (9), water (0.40 g), and acetone (0.08 g) were added to the reaction solution, and the mixture was stirred at room temperature for 3 hours and 25 minutes and then left overnight. After the reaction solution was stirred at room temperature for 1 hour, then water (30.39 g) was added thereto, and the mixture was stirred for 3 hours and 25 minutes. The precipitated solid was collected by filtration to obtain the compound (9) (16.72 g, 88.3%).

$^1$H-NMR (CDCl$_3$) δ ppm: 1.19 (d, J=7.1 Hz, 3H), 2.91 (m, 1H), 3.61 (s, 3H), 3.90 (dd, J=13.6 Hz, 6.2 Hz, 1H), 4.12 (dd, J=13.6 Hz, 8.4 Hz, 1H), 5.18 (d, J=14.2 Hz, 1H), 5.22 (d, J=14.2 Hz, 1H), 6.85 (m, 2H), 6.96 (m, 1H), 7.00 (m, 1H), 7.14 (m, 2H), 7.31 (m, 2H), 7.50 (m, 2H), 7.70 (m, 1H), 7.89 (brs, 1H), 8.14 (m, 1H)

[2] Synthesis of Seed Crystal of Compound (9)

Sodium bromide (2.00 g, 19.4 mmol) and N,N-dimethylacetamide (13.67 g) were added to the compound (5) (5.01 g, 17.9 mmol). N, N-diisopropylethylamine (2.55 g, 19.7 mmol) and N, N-dimethylacetamide (0.47 g) were added to the reaction solution, and the mixture was heated to 75° C. To the reaction solution, an N,N-dimethylacetamide solution of 4-chlorobenzyl chloride prepared by dissolving 4-chlorobenzyl chloride (3.16 g, 19.6 mmol) in N,N-dimethylacetamide (4.71 g) was added at 75° C., and N,N-dimethylacetamide (4.71 g) was added. The reaction solution was stirred at 75° C. for 4 hours and 30 minutes. The reaction solution was cooled to 25° C., acetic acid (0.32 g, 5.3 mmol) was added thereto, and the mixture was heated to 40° C. To the reaction solution, an N,N-dimethylacetamide solution of the compound (8) prepared by dissolving the compound (8) (3.66 g, 19.7 mmol) in N, N-dimethylacetamide (4.71 g) was added, and N, N-dimethylacetamide (4.71 g) was added. The reaction solution was stirred at 40° C. for 3 hours and 25 minutes, and was cooled to room temperature. To the reaction solution, acetone (13.79 g) and water (17.54 g) were added. The reaction solution was allowed to stand overnight at room temperature. After the reaction solution was heated to 25° C. and stirred for 5 hours, then water (15.00 g) was added thereto, and the mixture was stirred at 25° C. for 2 hours. The precipitated solid was collected by filtration to obtain a seed crystal of the compound (9) (8.17 g, 87.2%).

Example 3

Synthesis of Compound Represented by Formula (I)

[Chemical formula 48]

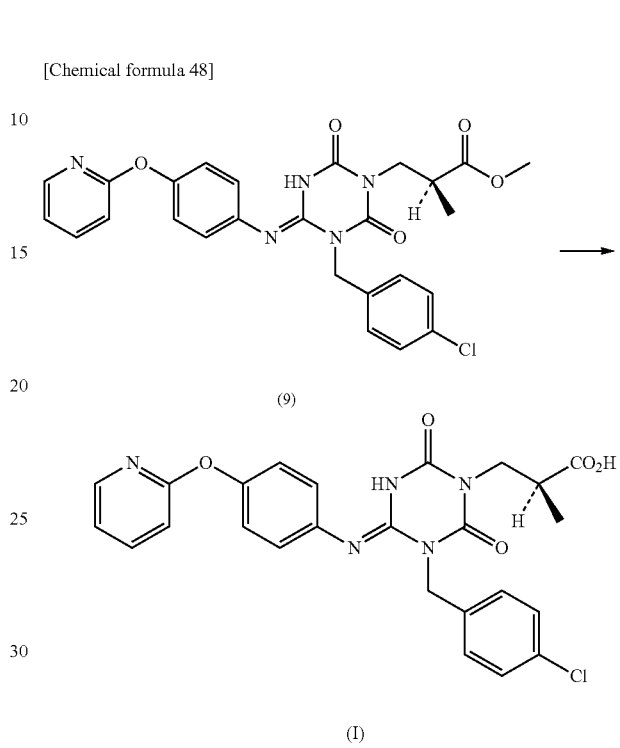

[1] Synthesis of Compound Represented by Formula (I)

To the compound (9) (70.00 g, 134.1 mmol), 2-propanol (109.91 g), water (63.00 g), and a 48% sodium hydroxide aqueous solution (27.94 g, 335.3 mmol) were added. The reaction solution was heated to 35° C. and stirred for 4 hours and 10 minutes. To the reaction solution, 2-propanol (32.97 g), methanol (177.30 g) and water (63.00 g) were added, and the mixture was heated to 50° C. Formic acid (18.52 g, 402.3 mmol) and the seed crystal of the compound represented by Formula (I) (70.00 mg) were added to the reaction solution, and the mixture was stirred at 50° C. for 1 hour and 10 minutes. Thereafter, water (280.00 g) was added thereto, and the mixture was cooled to 25° C. The precipitated solid was collected by filtration to obtain an anhydrous crystal Form I of the compound represented by Formula (I) (62.86 g, 92.3%).

$^1$H-NMR (CDCl$_3$) δ ppm: 1.13 (d, J=7.0 Hz, 3H), 2.76 (m, 1H), 3.83 (dd, J=13.5 Hz, 6.1 Hz, 1H), 4.03 (dd, J=13.5 Hz, 8.5 Hz, 1H), 5.14 (m, 1H), 5.25 (d, J=14.4 Hz, 1H), 6.82 (d, J=8.6 Hz, 2H), 7.00 (m, 2H), 7.08 (m, 2H), 7.25 (m, 2H), 7.43 (d, J=8.3 Hz, 2H), 7.72 (m, 1H), 8.06 (dd, J=5.4 Hz, 1.8 Hz, 1H), 8.67 (brs, 1H)

[2] Synthesis of Crystal Seed of Compound Represented by Formula (I)

To the compound (9) (1.50 g, 2.87 mmol), methanol (5.95 g), water (3.00 g), and a 48% sodium hydroxide aqueous solution (0.60 g, 7.20 mmol) were added. The reaction solution was heated to 40° C. and stirred for 1 hours and 30 minutes. The reaction solution was cooled to room temperature, formic acid (0.40 g, 8.62 mmol), ethyl acetate (10.5 mL) and water (9 mL) were added thereto at room temperature, and an aqueous layer was removed by liquid separation. Water (3 mL) was added to the obtained organic layer, an aqueous layer was removed by liquid separation, 2-propanol (90 mL) was added to the organic layer, and the mixture was concentrated under reduced pressure at 40° C. Water (7.5 mL) and 2-propanol (7.5 mL) were added to the obtained concentrated residue, and the mixture was stirred at 25° C. for 1 hour and 30 minutes. Water (7.5 mL) and methanol (7.5 mL) were added, then the mixture was heated to 60° C. and stirred for 2 hours, and cooled to 25° C. The precipitated solid was collected by filtration to obtain a seed crystal (10, 1.25 g, 85.6%) of an anhydrous crystal Form I crystal of the compound represented by Formula (I).

The results of powder X-ray diffraction of the anhydrous crystal Form I of the compound represented by Formula (I) are shown in FIG. 1 (Method 1).

In the powder X-ray diffraction spectrum, peaks are recognized at:

diffraction angles (2θ) of: 12.6°±0.2°, 12.9°±0.2°, 15.8°±0.2°, 19.4°±0.2°, 21.7°±0.2°, 23.9°±0.2°, 25.4°±0.2°, 26.6°±0.2°, 27.8°±0.2°, and 32.8°±0.2°; or diffraction angles (2θ) of 7.9°±0.2°, 9.3°±0.2°, 12.9°±0.2°, 15.8°±0.2°, 17.2°±0.2°, 19.4°±0.2°, 21.7°±0.2°, 23.9°±0.2°, 25.4°±0.2°, and 27.8°±0.2°.

In the powder X-ray diffraction spectrum, the peaks at the following diffraction angles (2θ) are particularly characteristic of the anhydrous crystal Form I of the compound represented by Formula (I):

15.8°±0.2°, 19.4°±0.2°, 21.7°±0.2°, 23.9°±0.2°; and 25.4°±0.2°; or 7.9°±0.2°, 9.3°±0.2°, 12.9°±0.2°, 15.8°±0.2°, and 19.4°±0.2°.

The results of Raman spectrum of the anhydrous crystal Form I of the compound represented by Formula (I) are shown in FIG. 2 (Method 1).

Main absorption peaks are recognized at 829 cm$^{-1}$±2 cm$^{-1}$, 989 cm$^{-1}$±2 cm$^{-1}$, 1013 cm$^{-1}$±2 cm$^{-1}$, 1093 cm$^{-1}$±2 cm$^{-1}$, 1128 cm$^{-1}$±2 cm$^{-1}$, 1243 cm$^{-1}$±2 cm$^{-1}$, 1370 cm$^{-1}$±2 cm$^{-1}$, 1599 cm$^{-1}$±2 cm$^{-1}$, 1659 cm$^{-1}$±2 cm$^{-1}$, 1735 cm$^{-1}$±2 cm$^{-1}$, 2938 cm$^{-1}$±2 cm$^{-1}$, and 3067 cm$^{-1}$±2 cm$^{-1}$.

In one embodiment, the anhydrous crystal Form I of the compound represented by Formula (I) has absorption peaks at 829 cm$^{-1}$±2 cm$^{-1}$, 989 cm$^{-1}$±2 cm$^{-1}$, 1013 cm$^{-1}$±2 cm$^{-1}$, 1128 cm$^{-1}$±2 cm$^{-1}$, and 1370 cm$^{-1}$±2 cm$^{-1}$.

In one embodiment, the anhydrous crystal Form I of the compound represented by Formula (I) has an absorption peak at 829 cm$^{-1}$±2 cm$^{-1}$.

In one embodiment, the anhydrous crystal Form I of the compound represented by Formula (I) has an absorption peak at 989 cm$^{-1}$±2 cm$^{-1}$.

In one embodiment, the anhydrous crystal Form I of the compound represented by Formula (I) has an absorption peak at 1013 cm$^{-1}$±2 cm$^{-1}$.

In one embodiment, the anhydrous crystal Form I of the compound represented by Formula (I) has an absorption peak at 1128 cm$^{-1}$±2 cm$^{-1}$.

In one embodiment, the anhydrous crystal Form I of the compound represented by Formula (I) has an absorption peak at 1370 cm$^{-1}$±2 cm$^{-1}$.

In one embodiment, the anhydrous crystal Form I of the compound represented by Formula (I) has one or more absorption peaks selected from the group consisting of an absorption peak at 829 cm$^{-1}$±2 cm$^{-1}$, an absorption peak at 989 cm$^{-1}$±2 cm$^{-1}$, an absorption peak at 1013 cm$^{-1}$±2 cm$^{-1}$, an absorption peak at 1128 cm$^{-1}$±2 cm$^{-1}$, and an absorption peak at 1370 cm$^{-1}$±2 cm$^{-1}$.

DSC analysis results of the anhydrous crystal Form I of the compound represented by Formula (I) are shown in FIG. 3. The onset temperature was about 196° C.

The results of single crystal structure analysis of the anhydrous crystal Form I of the compound represented by Formula (I) are shown below.

Crystallographic data are shown in Table 4.

TABLE 4

| Space group | P1 |
|---|---|
| a (Å) | 9.8720 (5) |
| b (Å) | 10.9952 (5) |
| c (Å) | 12.2781 (6) |
| α (°) | 67.712 (4) |
| β (°) | 80.870 (4) |
| γ (°) | 86.935 (4) |
| V (Å$^3$) | 1217.50 (11) |
| Z | 2 |
| Density (calculated value) (g/cm$^3$) | 1.386 |
| Measured temperature (K) | 298.15 |

Here, V represents a volume of a unit lattice, and Z represents the number of molecules in the unit lattice.

Atomic coordinates of non-hydrogen atoms are shown in Tables 5 to 7. Here, U (eq) means an equivalent isotropic temperature factor.

TABLE 5

| Atom | x | y | z | U(eq) |
|---|---|---|---|---|
| Cl2 | 2485 (2) | 7006 (2) | −759.2 (19) | 104.9 (7) |
| Cl1 | 7426.0 (16) | 2947.5 (18) | 10766.8 (15) | 88.8 (5) |
| N5 | 2089 (4) | 2884 (4) | 7834 (3) | 46.5 (9) |
| N9 | 7630 (4) | 7464 (4) | 4017 (4) | 50.4 (9) |
| N2 | 1056 (4) | 4687 (4) | 8118 (4) | 51.9 (10) |
| C16 | 3580 (5) | 2450 (5) | 9435 (4) | 44.5 (10) |
| O5 | 5867 (3) | 1451 (3) | 5338 (3) | 63.8 (8) |
| N8 | 8842 (4) | 5752 (4) | 3669 (4) | 50.7 (10) |
| C9 | 394 (5) | 5906 (5) | 7725 (5) | 48.6 (11) |
| O2 | 1151 (4) | 4145 (4) | 4553 (3) | 65.3 (10) |
| O6 | 11217 (6) | 534 (5) | 3496 (4) | 86.5 (15) |
| C12 | 1387 (5) | 4061 (5) | 7442 (4) | 44.9 (10) |
| C21 | 4123 (5) | 1390 (5) | 10288 (4) | 48.7 (11) |
| O3 | 3152 (4) | 1150 (4) | 7525 (4) | 69.7 (11) |
| O7 | 8862 (4) | 6055 (4) | 5375 (4) | 73.6 (12) |
| O8 | 6672 (5) | 8973 (4) | 2517 (4) | 76.4 (12) |
| N3 | 1081 (4) | 4424 (4) | 6293 (3) | 47.9 (9) |
| C6 | −895 (6) | 8306 (6) | 7034 (5) | 61.0 (14) |
| O4 | 5488 (6) | 3422 (5) | 5303 (5) | 122 (2) |
| O1 | −1611 (5) | 9501 (4) | 6620 (4) | 72.8 (12) |
| N4 | 2263 (4) | 2677 (4) | 5979 (3) | 46.6 (9) |
| N1 | −2337 (5) | 11398 (4) | 6748 (4) | 61.2 (11) |
| C11 | −1514 (6) | 7271 (6) | 7984 (5) | 62.9 (14) |
| C39 | 7334 (5) | 7962 (5) | 2859 (5) | 53.8 (12) |
| C26 | 11309 (6) | −350 (6) | 2949 (6) | 61.7 (14) |
| N10 | 7785 (4) | 7278 (4) | 2156 (4) | 54 (1) |
| C13 | 1468 (4) | 3771 (5) | 5546 (4) | 46.8 (11) |
| C27 | 10625 (6) | −195 (6) | 2050 (5) | 62.2 (14) |
| N7 | 8777 (5) | 5455 (4) | 1869 (4) | 56.6 (11) |
| C19 | 5944 (5) | 2756 (5) | 10236 (5) | 56.2 (12) |
| C15 | 2220 (5) | 2247 (5) | 9106 (4) | 50.8 (12) |
| C35 | 8767 (6) | 3165 (6) | 3297 (5) | 59.7 (13) |
| C20 | 5306 (6) | 1541 (5) | 10695 (5) | 58.4 (14) |
| C43 | 4464 (7) | 6225 (6) | 638 (6) | 77.4 (18) |
| C10 | −861 (6) | 6078 (6) | 8345 (5) | 60.8 (14) |

TABLE 6

| Atom | x | y | z | U(eq) |
|---|---|---|---|---|
| C14 | 2559 (5) | 2162 (5) | 7135 (4) | 47.9 (11) |
| C3 | −797 (7) | 11219 (6) | 8455 (6) | 71.5 (16) |
| C42 | 5646 (7) | 6422 (6) | 1043 (6) | 68.7 (16) |
| C25 | 5201 (4) | 2540 (5) | 5041 (5) | 59.2 (11) |
| C33 | 10562 (6) | 3952 (6) | 1643 (5) | 63.7 (14) |
| C45 | 4543 (5) | 8455 (6) | −693 (6) | 61.4 (14) |
| C36 | 9349 (7) | 1932 (6) | 3659 (6) | 67.0 (14) |
| C37 | 8488 (5) | 6084 (5) | 2556 (4) | 48.2 (11) |
| C22 | 2781 (6) | 1991 (5) | 5167 (5) | 58.0 (13) |
| C8 | 1001 (5) | 6986 (5) | 6771 (5) | 57.1 (12) |
| C38 | 8481 (5) | 6386 (5) | 4415 (5) | 51.8 (12) |
| C23 | 4057 (6) | 2625 (6) | 4312 (5) | 70.8 (15) |
| C40 | 7634 (6) | 7882 (6) | 887 (5) | 60.1 (13) |
| C17 | 4243 (6) | 3641 (6) | 8995 (6) | 67.1 (16) |
| C2 | −706 (6) | 10229 (6) | 8011 (5) | 61.3 (14) |
| C48 | 5436 (6) | 7790 (5) | 5213 (6) | 75.3 (15) |
| C47 | 7008 (5) | 8083 (5) | 4823 (5) | 57.3 (13) |
| C7 | 357 (6) | 8178 (5) | 6432 (6) | 62.8 (14) |
| C29 | 11615 (9) | −2201 (10) | 1989 (10) | 102 (3) |
| C5 | −2364 (7) | 12341 (6) | 7181 (7) | 75.4 (17) |
| N6 | 12158 (7) | −1341 (7) | 3399 (7) | 101 (2) |
| C4 | −1580 (7) | 12266 (7) | 8041 (6) | 76.8 (17) |
| C44 | 3942 (6) | 7268 (6) | −236 (6) | 67.4 (16) |
| C34 | 9370 (5) | 4183 (5) | 2302 (4) | 50.9 (12) |
| C28 | 10776 (8) | −1146 (8) | 1577 (7) | 87 (2) |
| C46 | 5696 (6) | 8637 (5) | −274 (5) | 55.9 (13) |
| C18 | 5428 (6) | 3801 (6) | 9379 (6) | 72.0 (17) |
| C1 | −1548 (6) | 10380 (5) | 7151 (5) | 55.8 (12) |
| C32 | 11169 (7) | 2719 (7) | 2022 (6) | 72.8 (17) |
| C31 | 10575 (7) | 1732 (6) | 3028 (5) | 64.7 (15) |
| C41 | 6282 (5) | 7645 (5) | 579 (4) | 50.7 (12) |
| C24 | 4458 (8) | 1956 (11) | 3447 (7) | 116 (3) |
| C30 | 12262 (10) | −2294 (9) | 2895 (10) | 108 (3) |
| O10 | 4974 (11) | 6061 (7) | 4658 (8) | 178 (4) |
| C50 | 5087 (8) | 6417 (7) | 5478 (7) | 95 (2) |

TABLE 7

| Atom | x | y | z | U(eq) |
|---|---|---|---|---|
| O9 | 5280(20) | 5578(9) | 6379(9) | 328(10) |
| C49 | 4896(8) | 8186(9) | 6272(10) | 121(3) |

Atomic coordinates of hydrogen atoms are shown in Tables 8 and 9. Here, U (iso) means an isotropic temperature factor. The numbers of hydrogen atoms in Table 8 and 9 were assigned in relation to the numbers of non-hydrogen atoms bonded thereto.

TABLE 8

| Atom | x | y | z | U(eq) |
|---|---|---|---|---|
| H8 | 9346.77 | 5068.7 | 3913.78 | 61 |
| H21 | 3688.72 | 574.05 | 10586.55 | 58 |
| H3 | 605.17 | 5124.26 | 6028.82 | 58 |
| H11 | −2369.74 | 7373.12 | 8382.1 | 75 |
| H27 | 10069.67 | 531.08 | 1757.55 | 75 |
| H15A | 2067.68 | 1310.62 | 9351.81 | 61 |
| H15B | 1497.97 | 2573.94 | 9556.73 | 61 |
| H35 | 7956.48 | 3311.88 | 3730.76 | 72 |
| H20 | 5667.21 | 833.82 | 11271.28 | 70 |
| H43 | 4035.48 | 5405.74 | 950.95 | 93 |
| H10A | −1260.54 | 5381.3 | 9009.97 | 73 |
| H3A | −297.7 | 11150.91 | 9057.25 | 86 |
| H42 | 6008.86 | 5728.15 | 1629.39 | 82 |
| H33 | 10953.5 | 4619.29 | 949.33 | 76 |
| H45 | 4185.23 | 9145.91 | −1286.06 | 74 |
| H36 | 8922.52 | 1244.53 | 4318.29 | 80 |
| H22A | 2066.94 | 1977.02 | 4712.78 | 70 |
| H22B | 2984.22 | 1087.66 | 5637.74 | 70 |
| H8A | 1852.43 | 6897.22 | 6360.72 | 69 |
| H23 | 3869.03 | 3552.19 | 3869.51 | 85 |

TABLE 8-continued

| Atom | x | y | z | U(eq) |
|---|---|---|---|---|
| H40A | 8359.19 | 7555.79 | 439.33 | 72 |
| H40B | 7769.65 | 8823.57 | 624.36 | 72 |
| H17 | 3883.02 | 4354.24 | 8424.64 | 81 |
| H2 | −128.04 | 9513.17 | 8265.23 | 74 |
| H48 | 4971.94 | 8339.68 | 4545.7 | 90 |
| H47A | 7150.32 | 9026.02 | 4438.25 | 69 |
| H47B | 7459.01 | 7775.33 | 5525.24 | 69 |
| H7 | 769.29 | 8894.74 | 5794.62 | 75 |
| H29 | 11730.8 | −2832.7 | 1649.99 | 122 |
| H5A | −2923.15 | 13066.86 | 6898.98 | 90 |
| H4 | −1599.17 | 12938.91 | 8326.23 | 92 |
| H28 | 10297.82 | −1073.81 | 960.63 | 105 |
| H46 | 6096.11 | 9469.21 | −582.57 | 67 |
| H18 | 5876.37 | 4610.88 | 9061.11 | 86 |
| H32 | 11978.74 | 2566.14 | 1591.72 | 87 |

TABLE 9

| Atom | x | y | z | U(eq) |
|---|---|---|---|---|
| H24A | 5221.96 | 2413.89 | 2873.1 | 175 |
| H24B | 3696.38 | 1963.34 | 3045.27 | 175 |
| H24C | 4710.68 | 1064.7 | 3868.09 | 175 |
| H30 | 12805.06 | −3025.75 | 3202.32 | 130 |
| H10 | 4972.25 | 5256.08 | 4903.89 | 267 |
| H49A | 5188.95 | 7556.53 | 6980.6 | 182 |
| H49B | 3912.1 | 8211.16 | 6373.01 | 182 |
| H49C | 5249.84 | 9039.79 | 6125.23 | 182 |
| H5 | 6580(60) | 1560(80) | 5680(70) | 140(30) |

Further, interatomic bond distances (unit: angstrom) are shown in Tables 10 to 11.

TABLE 10

| Atom | Atom | Length/Å | Atom | Atom | Length/Å |
|---|---|---|---|---|---|
| Cl2 | C44 | 1.744(6) | C26 | C27 | 1.336(8) |
| Cl1 | C19 | 1.746(5) | C26 | N6 | 1.337(8) |
| N5 | C12 | 1.387(6) | N10 | C37 | 1.403(6) |
| N5 | C15 | 1.474(6) | N10 | C40 | 1.473(7) |
| N5 | C14 | 1.390(6) | C27 | C28 | 1.368(9) |
| N9 | C39 | 1.389(6) | N7 | C37 | 1.271(7) |
| N9 | C38 | 1.390(6) | N7 | C34 | 1.423(6) |
| N9 | C47 | 1.448(7) | C19 | C20 | 1.381(8) |
| N2 | C9 | 1.405(6) | C19 | C18 | 1.370(8) |
| N2 | C12 | 1.262(6) | C35 | C36 | 1.381(8) |
| C16 | C21 | 1.388(6) | C35 | C34 | 1.380(8) |
| C16 | C15 | 1.513(7) | C43 | C42 | 1.396(9) |
| C16 | C17 | 1.370(8) | C43 | C44 | 1.383(8) |
| O5 | C25 | 1.288(5) | C3 | C2 | 1.384(8) |
| N8 | C37 | 1.371(6) | C3 | C4 | 1.329(9) |
| N8 | C38 | 1.344(6) | C42 | C41 | 1.387(8) |
| C9 | C10 | 1.391(7) | C25 | C23 | 1.527(7) |
| C9 | C8 | 1.392(8) | C33 | C34 | 1.388(7) |
| O2 | C13 | 1.216(6) | C33 | C32 | 1.392(8) |
| O6 | C26 | 1.367(7) | C45 | C44 | 1.339(9) |
| O6 | C31 | 1.386(7) | C45 | C46 | 1.375(8) |
| C12 | N3 | 1.391(6) | C36 | C31 | 1.385(9) |
| C21 | C20 | 1.382(7) | C22 | C23 | 1.514(8) |
| O3 | C14 | 1.194(5) | C8 | C7 | 1.369(7) |
| O7 | C38 | 1.210(6) | C23 | C24 | 1.501(9) |
| O8 | C39 | 1.222(6) | C40 | C41 | 1.505(8) |
| N3 | C13 | 1.364(6) | C17 | C18 | 1.372(8) |
| C6 | O1 | 1.412(6) | C2 | C1 | 1.401(8) |
| C6 | C11 | 1.368(9) | C48 | C47 | 1.563(8) |
| C6 | C7 | 1.365(8) | C48 | C50 | 1.467(8) |
| O4 | C25 | 1.191(6) | C48 | C49 | 1.532(10) |
| O1 | C1 | 1.364(6) | C29 | C28 | 1.368(12) |
| N4 | C13 | 1.375(5) | C29 | C30 | 1.337(13) |
| N4 | C14 | 1.388(6) | C5 | C4 | 1.381(9) |
| N4 | C22 | 1.481(6) | N6 | C30 | 1.398(12) |

TABLE 11

| Atom | Atom | Length/Å | Atom | Atom | Length/Å |
|------|------|----------|------|------|----------|
| N1   | C5   | 1.331(7) | C46  | C41  | 1.371(7) |
| N1   | C1   | 1.309(7) | C32  | C31  | 1.366(10) |
| C11  | C10  | 1.376(8) | O10  | C50  | 1.231(10) |
| C39  | N10  | 1.359(7) | C50  | O9   | 1.178(13) |

In the anhydrous crystal Form I of the compound represented by Formula (I), two molecules of the compound represented by Formula (I) were present in an asymmetric unit. Molecular structural diagrams of the compound represented by Formula (I) are shown in FIGS. 7 and 8, respectively.

The numbers of non-hydrogen atoms in Tables 5 to 7 and Tables 10 and 11 correspond to the numbers shown in FIGS. 7 and 8, respectively.

As shown in Tables 10 to 11, the bond distance of C12-N2 was about 1.26 Å, and the bond distance of C37-N7 was about 1.27 Å.

Since the bond distance of C12-N2 and the bond distance of C37-N7 are shorter than the bond distance of C12-N3 (about 1.39 Å) and the bond distance of C37-N8 (about 1.37 Å), the compounds represented by Formula (I) in the anhydrous crystal Form I were identified to have an imino structure:

[Chemical formula 49]

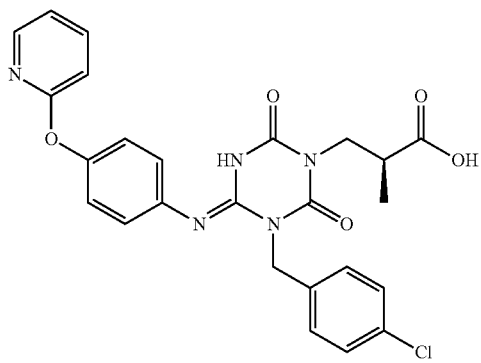

Example 4

Effect Achieved by Additive for Acceleration of Aza-Michael Addition Reaction

[Chemical formula 50]

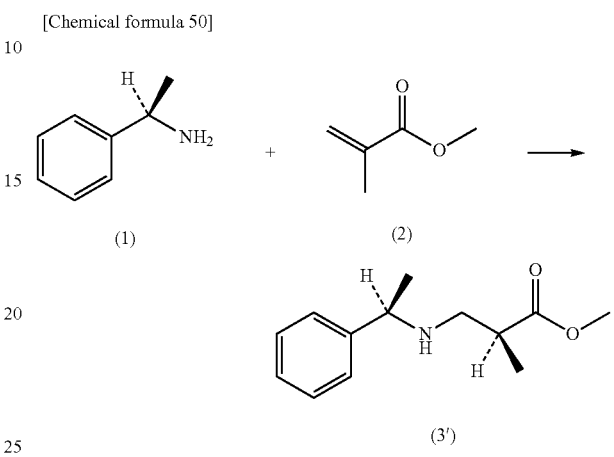

A reaction similar to the above scheme is described in Tetrahedron Asymmetry, Vol. 7, No. 3, pp. 699-708, 1996 (Non-Patent Document 16). In this literature, a product of an aza-Michael addition reaction is obtained by heating and refluxing for 9 days using methanol as a reaction solvent (yield 74%, 1:1 diastereomeric mixture). Methyl methacrylate (the compound 2), which is a raw material, is a compound used as a raw material for polymer synthesis, and may be polymerized when subjected to a reaction at a high temperature for a long time. Therefore, these reaction conditions are not suitable for an industrial process method.

On the other hand, it was found that, in the above-described aza-Michael addition reaction, when lithium chloride, calcium chloride, magnesium chloride, lithium bromide, p-toluenesulfonic acid, methanesulfonic acid, or trifluoromethanesulfonic acid was used as an additive, the reaction was accelerated as shown in Table 12 below.

TABLE 12

| Additive | Equivalent number with respect to compound (1) (eq.) | Reaction temperature (° C.) | Reaction time (h) | Conv. (%)* |
|----------|----|----|----|----|
| Lithium chloride | 1 | 80 | 1.3 | 76 |
| Lithium chloride | 1 | 80 | 6.5 | 96 |
| Calcium chloride | 1 | 80 | 1 | 68 |
| Magnesium chloride | 1 | 80 | 4 | 74 |
| Lithium bromide | 1 | 80 | 6 | 95 |
| p-toluenesulfonic acid | 0.1 | 100 | 4 | 78 |
| p-toluenesulfonic acid | 0.1 | 100 | 7 | 85 |
| Methanesulfonic acid | 0.05 | 100 | 4 | 75 |
| Methanesulfonic acid | 0.05 | 100 | 7 | 84 |
| Trifluoromethanesulfonic acid | 0.05 | 80 | 5 | 77 |

In the same manner as in Example 1, reactions were performed under the respective conditions in Table 12 above. Each reaction solution was sampled while being stirred, about 100 mg of the reaction solution was weighed, methanol for liquid chromatography was added thereto to dilute the solution to 100 mL, 10 µL of the diluted solution was injected, and HPLC (Method A) was measured.

*Conv. (%) was calculated by the following formula.

[Mathematical formula 1]
$$Conv.(\%) = \frac{A3' + A3''}{A1 + A3' + A3''} \times 100$$

Here, A1, A3', and A3" represent peak areas in HPLC measurement, respectively.

A1: Compound (1)
A3': Compound (3')
A3": Compound (3")

The compound (3") has the following chemical structural formula.

[Chemical formula 51]

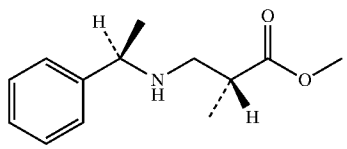

(3")

Until now, only the reaction conditions for heating and refluxing for 9 days as described in Non-Patent Document 16 have been known, but the reaction is accelerated in the presence of these additives, and is completed in a short time of 1 hour to 7 hours, so that it can be said that the present process method is an industrially excellent process method.

In Non-Patent Document 16, after completion of the aza-Michael addition reaction of (S)-1-phenylethylamine ((S)-α-methylbenzylamine) and methyl methacrylate, p-toluenesulfonic acid is added to obtain a p-toluenesulfonic acid salt. On the other hand, in the present application, after completion of the aza-Michael addition reaction of (R)-1-phenylethylamine ((R)-(+)-1-phenylethylamine) and methyl methacrylate, p-toluenesulfonic acid is added to obtain a p-toluenesulfonic acid. That is, in Non-Patent Document 16, the p-toluenesulfonic acid salt of an enantiomer of Formula (IV-B) of the present application is obtained, and thus the present invention is not described in Non-Patent Document 16:

[Chemical formula 52]

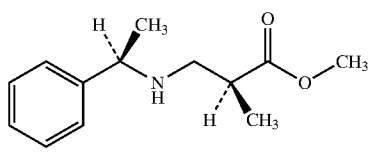

(IV-B)

Example 5

Comparison of Isolation Yields of Sulfate and Hydrochloride of Compound (4')

[Chemical formula 53]

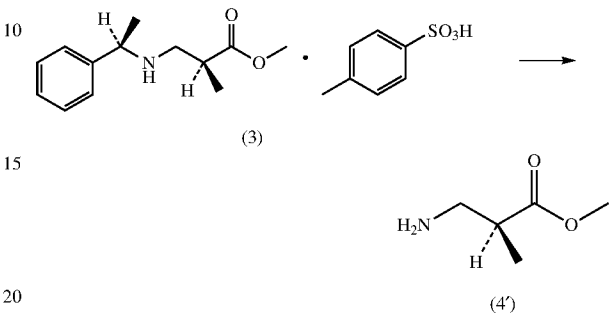

Methanol and a 4 mol/L hydrochloric acid-ethyl acetate solution were added to the filtrate after removal of palladium on carbon in the same manner as in the process method described in Example 2. Ethyl acetate was added as a crystallization solvent, and the operation of concentration under reduced pressure was repeated. The solvent was replaced with ethyl acetate, and the mixture was cooled to 0° C. The precipitated solid was collected by filtration to obtain a hydrochloride of the compound (4'). The sulfate of the compound (4') was synthesized according to Example 2 described above.

Here, regarding the isolation yield of the hydrochloride of the compound (4') or the sulfate of the compound (4') and filtrates after collecting the precipitated solid by filtration, about 200 mg of each were weighed and 15 mL of acetonitrile and 45 µL and triethylamine for liquid chromatography were added, then 15 µL of benzoyl chloride was added, and acetonitrile for liquid chromatography was added to dilute each mixture to 20 mL, then 10 µL of the mixture was injected, and HPLC (Method B) was measured. Separately, as a standard solution for concentration calculation, about 10 mg of an isolated solid of the hydrochloride of the compound (4') or the isolated solid of the sulfate of the compound (4') was weighed, and 15 mL of acetonitrile and 45 µL of triethylamine for liquid chromatography were added, then 15 µL of benzoyl chloride was added, and acetonitrile for liquid chromatography was added to dilute the mixture to 20 mL, then 10 µL of the mixture was injected, HPLC (Method B) was measured, and the concentration of the compound (4') contained in the filtrate was calculated by the following formula.

[Mathematical formula 2]

Filtrate loss (%) =

$$\frac{M_S}{M_L} \times \frac{A_L}{A_S} \times \text{Filtrate weight (g)/Theoretical yield (g)} \times 100$$

Here, $M_S$, $M_L$, $A_S$, and $A_L$ represent peak areas in HPLC measurement, respectively.

$M_S$: weighed amount (mg) of an isolated solid of hydrochloride of compound (4') or sulfate of compound (4') in HPLC measurement $M_L$: weighed amount (mg) of filtrate in HPLC measurement $A_S$: peak area of an isolated solid of hydrochloride of compound (4') or sulfate of compound (4') in HPLC measurement $A_L$: peak area of filtrate in HPLC measurement

TABLE 13

| Entry | Salt | Isolation yield (%) | Filtrate loss (%) | Crystallization solvent |
|---|---|---|---|---|
| 1 | Hydrochloride | 88.0 | — | AcOEt |
| 2 | Hydrochloride | 83.0 | 7.1 | AcOEt |
| 3 | Hydrochloride | 79.0 | 10.3 | AcOEt |
| 4 | Hydrochloride | 82.9 | 6.2 | AcOEt |
| 5 | Hydrochloride | 83.4 | 6.5 | AcOEt |
| 6 | Hydrochloride | 77.0 | 3.0 | AcOEt |
| 7 | Sulfate | 92.4 | 2.5 | MeCN |
| 8 | Sulfate | 94.0 | 3.0 | MeCN |
| 9 | Sulfate | 91.9 | 1.8 | MeCN |
| 10 | Sulfate | 93.4 | 3.0 | MeCN |

As is apparent from Table 13, when the compound (4') was isolated as a hydrochloride (entries 1 to 6), the isolation yield varied from about 77% to about 88%. In addition, about 3% to about 10% of a free form (compound (4')) eluted in the filtrate was confirmed.

On the other hand, when the compound (4') was isolated as a sulfate (entries 7 to 10), a high isolation yield of about 92% to about 94% was achieved. The proportion of the free form eluted into the filtrate was about 2 to about 3%.

From the above results, it can be said that the method for producing the compound (4') as a sulfate is an industrially excellent process method because the amount of the free form eluted in the filtrate is small, which means that the loss during process is small.

Example 6

Racemization Suppressing Effect

[Chemical formula 54]

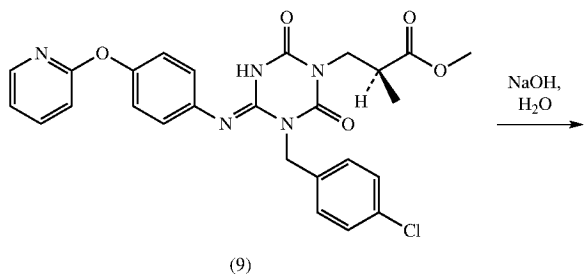

(9)

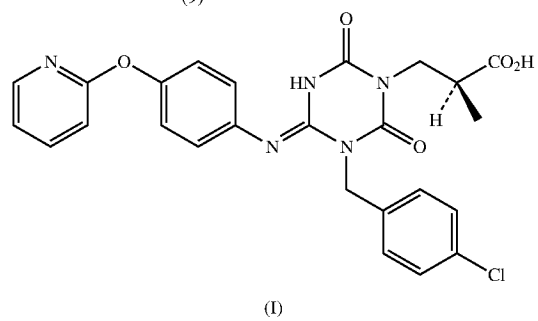

(I)

Patent Documents 6, 7, 8, and 9 disclose a process method for obtaining a carboxylic acid by hydrolyzing an ester, and as a solvent, dioxane, THF, DMSO, a MeOH-THF mixed solution, a THF-EtOH-water mixed solution, a MeOH-water mixed solution, a MeOH-THF-water mixed solution, or the like is used.

On the other hand, when isopropyl alcohol, THF, or t-BuOH was used as a reaction solvent in the hydrolysis reaction, racemization of a product was found to be suppressed as shown in Table 14 below.

TABLE 14

| Solvent | Reaction time (h) | Reaction temperature (° C.) | R form of compound (9) (%)* | R form of compound represented by Formula (I) (%)** |
|---|---|---|---|---|
| MeOH | 1 | 40 | 0.43 | 0.93 |
| EtOH | 1 | 40 | 0.43 | 0.70 |
| EtOH | 2 | 40 | 0.43 | 0.68 |
| Isopropyl alcohol | 1 | 40 | 0.43 | 0.54 |
| Isopropyl alcohol | 2 | 40 | 0.43 | 0.53 |
| THF | 1 | 40 | 0.43 | 0.52 |
| t-BuOH | 0.5 | 50 | 0.44 | 0.48 |

In the same manner as in Example 3, reactions were performed under the respective conditions in the table above. About 100 mg of each reaction solution was weighed, methanol for liquid chromatography was added thereto to dilute the solution to 20 mL, 10 μL of the diluted solution was injected, and HPLC (Method C) was measured.

*The R form amount of the compound (9) was calculated by the following formula. The unit represents a peak area (%).

$$\frac{\text{Area \% of } R \text{ isomer of compound (9)}}{\text{Area \% of compound (9)} + \text{Area \% of } R \text{ isomer of compound (9)}} \times 100 \quad \text{[Mathematical formula 3]}$$

**The R isomer amount of the compound represented by Formula (I) was calculated by the following formula. The unit represents a peak area (%).

[Mathematical formula 4]

$$\frac{\text{Area \% of } R \text{ isomer of compound represented by Formula (I)}}{\text{Area \% of compound represented by Formula (I)} + \text{Area \% of } R \text{ isomer of compound represented by Formula (I)}} \times 100$$

The structural formulae of the R isomer of the compound (9) and the R isomer of the compound represented by Formula (I) are as follows. The molecular structures (amino form/imino form) of the R isomer of the compound (9) and the R isomer of the compound represented by Formula (I) have not been determined.

[Chemical formula 55]

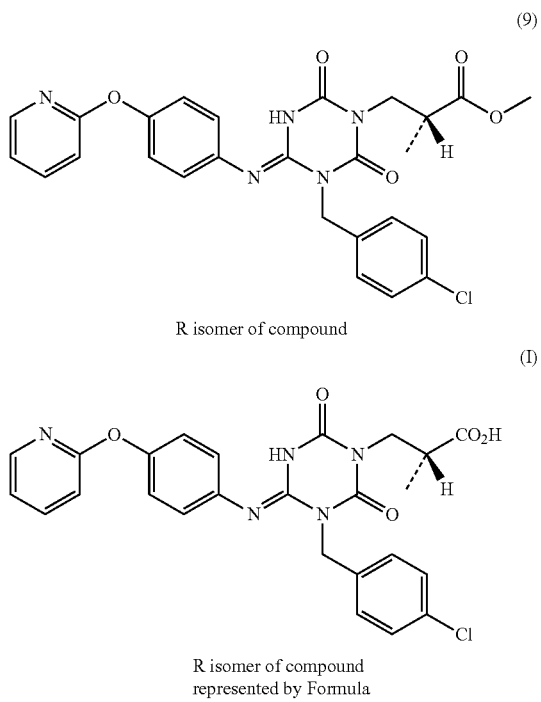

R isomer of compound (9)

R isomer of compound represented by Formula (I)

As described in Table 14 above, it was found that when methanol was used as the reaction solvent, racemization occurred, and the amount of optical isomers increased from 0.43% to 0.93%. Also in the case of ethanol, the amount of optical isomers similarly increased from 0.43% to about 0.7%. On the other hand, when isopropyl alcohol, tetrahydrofuran and t-butanol were used, it increased to about 0.5%.

From the above results, it became clear that when isopropyl alcohol, tetrahydrofuran, and t-butanol were used, the ratio slightly increased from the ratio of the R isomer initially contained in the compound (9) as a starting material, and racemization was suppressed, as compared with the case where methanol and ethanol were used as reaction solvents. Therefore, it can be said that the present process method is an industrially excellent process method.

Example 7

[1] Synthesis of Dihydrate Crystal of Compound Represented by Formula (I)

To an anhydrous crystal Form I (50.00 g, 98.43 mmol) of the compound represented by Formula (I), 2-propanol (314.02 g), water (150.00 g), and 48% sodium hydroxide (20.51 g, 246.1 mmol) were added and dissolved. To the resulting solution, 35% hydrochloric acid (25.64 g, 246.1 mmol) and a seed crystal of a dihydrate of the compound represented by Formula (I) (50.00 mg) were added, then the mixture was stirred at room temperature for 1 hour, and water (250.00 g) was added and stirred for 2 hours. The obtained slurry was cooled to 5° C. and filtered to obtain a dihydrate crystal (49.23 g) of the compound represented by Formula (I).

The dihydrate crystal was confirmed by thermogravimetry/differential thermal analysis (TG/DTA), moisture absorption and desorption measurement (DVS), and powder X-ray diffraction measurement.

A powder X-ray diffraction pattern of the dihydrate crystal of the compound represented by Formula (I) is shown in FIG. 4 (Method 1).

Peaks at diffraction angles of 5.7°±0.2°, 7.7°±0.2°, 11.8°±0.2°, 15.2°±0.2°, 17.7°±0.2°, 20.6°±0.2°, 20.8°±0.2°, 26.5°±0.2°, 27.1°±0.2°, and 29.1°±0.2° are particularly characteristic of the dihydrate crystal of the compound represented by Formula (I).

The results of Raman spectrum of the dihydrate crystal of the compound represented by Formula (I) are shown in FIG. 6 (Method 2).

Main absorption peaks are recognized at 871 cm$^{-1}$±2 cm$^{-1}$, 996 cm$^{-1}$±2 cm$^{-1}$, 1093 cm$^{-1}$±2 cm$^{-1}$, 1114 cm$^{-1}$±2 cm$^{-1}$, 1234 cm$^{-1}$±2 cm$^{-1}$, 1248 cm$^{-1}$±2 cm$^{-1}$, 1340 cm$^{-1}$±2 cm$^{-1}$, 1577 cm$^{-1}$±2 cm$^{-1}$, 1603 cm$^{-1}$±2 cm$^{-1}$, 1662 cm$^{-1}$±2 cm$^{-1}$, 1738 cm$^{-1}$±2 cm$^{-1}$, 2971 cm$^{-1}$±2 cm$^{-1}$, and 3073 cm$^{-1}$±2 cm$^{-1}$.

In one embodiment, the dihydrate crystal of the compound represented by Formula (I) has absorption peaks at 871 cm$^{-1}$±2 cm$^{-1}$, 996 cm$^{-1}$±2 cm$^{-1}$, 1114 cm$^{-1}$±2 cm$^{-1}$, 1234 cm$^{-1}$±2 cm$^{-1}$, 1340 cm$^{-1}$±2 cm$^{-1}$, and 1577 cm$^{-1}$±2 cm$^{-1}$.

In one embodiment, the dihydrate crystal of the compound represented by Formula (I) has an absorption peak at 871 cm$^{-1}$±2 cm$^{-1}$.

In one embodiment, the dihydrate crystal of the compound represented by Formula (I) has an absorption peak at 996 cm$^{-1}$±2 cm$^{-1}$.

In one embodiment, the dihydrate crystal of the compound represented by Formula (I) has an absorption peak at 1114 cm$^{-1}$±2 cm$^{-1}$.

In one embodiment, the dihydrate crystal of the compound represented by Formula (I) has an absorption peak at 1234 cm$^{-1}$±2 cm$^{-1}$.

In one embodiment, the dihydrate crystal of the compound represented by Formula (I) has an absorption peak at 1340 cm$^{-1}$±2 cm$^{-1}$.

In one embodiment, the dihydrate crystal of the compound represented by Formula (I) has an absorption peak at 1577 cm$^{-1}$±2 cm$^{-1}$.

In one embodiment, the dihydrate crystal of the compound represented by Formula (I) has one or more absorption peaks selected from the group consisting of an absorption peak at 871 cm$^{-1}$±2 cm$^{-1}$, an absorption peak at 996 cm$^{-1}$±2 cm$^{-1}$, an absorption peak at 1114 cm$^{-1}$±2 cm$^{-1}$, an absorption peak at 1234 cm$^{-1}$±2 cm$^{-1}$, an absorption peak at 1340 cm$^{-1}$±2 cm$^{-1}$, and an absorption peak at 1577 cm$^{-1}$±2 cm$^{-1}$.

The results of the thermogravimetry/differential thermal analysis (TG/DTA) of the dihydrate crystals of the compound represented by Formula (I) are shown in FIG. 5. As a result, from about 55° C. to about 85° C., a weight loss of 6.4% with an endothermic peak was confirmed. Since the theoretical value of the moisture content of the dihydrate crystal of the compound represented by Formula (I) was 6.6%, it was confirmed to be a dihydrate crystal of the compound represented by Formula (I).

[2] Synthesis of Seed Crystal of Dihydrate of Compound Represented by Formula (I)

To the compound (9) (70.00 g, 134.1 mmol), 2-propanol (109.91 g), water (63.02 g), and a 48% sodium hydroxide (27.95 g, 335.4 mmol) were added, and the mixture was stirred at 25° C. for 4 hours. To the obtained reaction solution, 2-propanol (16.49 g), methanol (127.43 g), and water (217.00 g) were added, then formic acid (9.88 g, 215 mmol) was added thereto at 25° C., and the mixture was stirred at 25° C. for 35 minutes. To the obtained slurry, a formic acid aqueous solution prepared by mixing formic acid (8.64 g, 188 mmol) and water (70.00 g) was added dropwise at 25° C., and then water (7.00 g) and methanol (27.70 g) were added thereto. The obtained slurry was filtered to obtain a seed crystal of a dihydrate (64.04 g) of the compound represented by Formula (I).

Reference Example 4

Synthesis of Compound I-127 Described in Patent Document 9

As described above, each step for producing the compound I-127 is not specifically described in Patent Document 9. The compound I-127 was synthesized in the same manner as the similar compound of the compound I-127 (Reference Example 3 of Patent Document 9). Only the final step is shown below.

[Chemical formula 56]

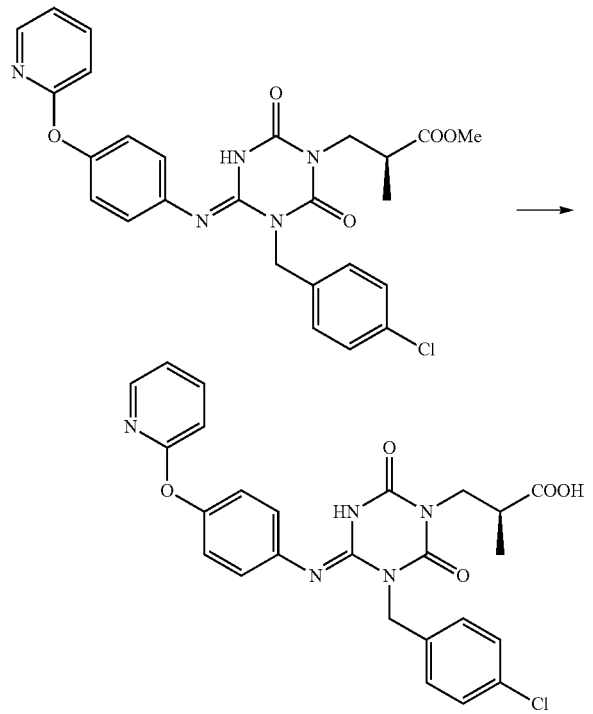

Methyl (S,E)-3-(3-(4-chlorobenzyl)-2,6-dioxo-4-((4-(pyridin-2-yloxy)phenyl)imino)-1,3,5-triazinan-1-yl)-2-methylpropanoate (0.365 g, 0.7 mmol), MeOH (1 mL), THF (1 mL), H$_2$O (1 mL), and a 4 mol/L-LiOH aqueous solution (0.7 mL, 2.80 mmol) were mixed, and the mixture was stirred at room temperature for 2 hours. The reaction solution was added to a half saturated brine (100 mL) and a 5% citric acid solution, and the mixture was extracted with ethyl acetate (100 mL), then an organic layer was washed with a half saturated brine (100 mL). The organic layer was dried over magnesium sulfate and then distilled off under reduced pressure. The obtained residue was purified by column chromatography (ethyl acetate/hexane=50:50 to ethyl acetate/hexane=80:20), then recrystallized with a mixed solvent of ethyl acetate/hexane, collected by filtration, and then dried under reduced pressure at 80° C. for 3 hours to obtain a white powder.

$^1$H NMR (DMSO-d6) δ: 0.86 (1.5H, t, J=6.8 Hz, hexane), 1.03 (3H, d, J=6.8 Hz), 1.18 (0.75H, t, J=7.4 Hz, AcOEt), 1.25 (2H, brs, hexane), 1.99 (0.75H, s, AcOEt), 2.76 (1H, t, J=7.2 Hz), 3.81 (1H, t, J=10.5 Hz), 3.95 (1H, t, J=10.2 Hz), 4.03 (0.5H, q, J=7.4 Hz, AcOEt), 5.29 (2H, s), 7.02-7.12 (4H, m), 7.36-7.45 (6H, m), 7.85 (1H, t, J=7.5 Hz), 8.16 (1H, s), 9.34 (1H, brs).

LC/MS m/z 508 [M+] Retention time 2.02 min

Here, LC/MS was measured under the conditions of Method 1 of Patent Document 9.

The results of $^1$H-NMR are shown in FIG. 9.

In the NMR spectrum chart, peaks of ethyl acetate and hexane are recognized. Since the obtained crystal was dried under reduced pressure at 80° C. for 3 hours, it was presumed that the obtained crystal was not an adhesion solvent on the crystal surface but ethyl acetate and hexane contained in the crystal lattice. In TG/DTA (FIG. 13), weight loss accompanied by endothermy was confirmed, and thus the obtained crystal was suggested to be a solvate crystal of ethyl acetate and hexane.

Furthermore, from the integration ratio of $^1$H-NMR, the abundance molar ratio of the compound represented by the formula:

[Chemical formula 57]

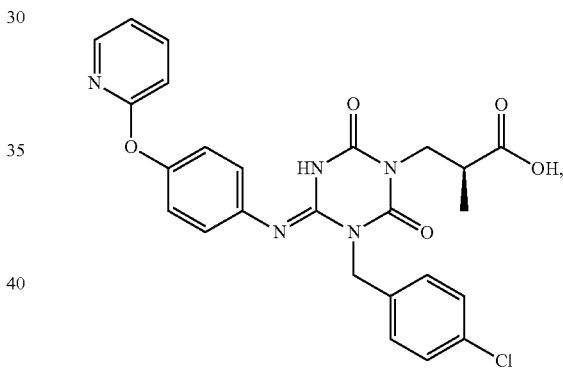

ethyl acetate, and hexane was about 4:1:1.

Therefore, regarding the compound I-127 described in Patent Document 9, an ethyl acetate/hexane solvate crystal of the compound represented by the formula:

[Chemical formula 58]

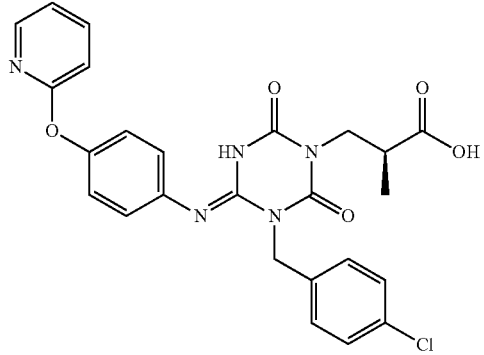

was presumed to have been obtained (however, the molecular structure (amino form/imino form) is unknown).

Next, the powder X-ray diffraction pattern of the obtained white powder is shown in FIG. 10 (Method 2).

In the powder X-ray diffraction spectrum, peaks are recognized at diffraction angles (2θ) of: 8.3°±0.2°, 10.8°±0.2°, 13.4°±0.2°, 17.9°±0.2°, 19.4°±0.2°, 21.7°±0.2°, and 25.6°±0.2°.

The result of the Raman spectrum of the obtained crystal is shown in FIG. 11 (Method 2).

Main absorption peaks are recognized at 821 cm$^{-1}$±2 cm$^{-1}$, 856 cm$^{-1}$±2 cm$^{-1}$, 893 cm$^{-1}$±2 cm$^{-1}$, 1002 cm$^{-1}$±2 cm$^{-1}$, 1094 cm$^{-1}$±2 cm$^{-1}$, 1221 cm$^{-1}$±2 cm$^{-1}$, 1269 cm$^{-1}$±2 cm$^{-1}$, 1575 cm$^{-1}$±2 cm$^{-1}$, 1604 cm$^{-1}$±2 cm$^{-1}$, 1614 cm$^{-1}$±2 cm$^{-1}$, 1649 cm$^{-1}$±2 cm$^{-1}$, 1725 cm$^{-1}$±2 cm$^{-1}$, and 3073 cm$^{-1}$±2 cm$^{-1}$.

Main absorption peaks are recognized at 821 cm$^{-1}$±2 cm$^{-1}$, 1002 cm$^{-1}$±2 cm$^{-1}$, 1269 cm$^{-1}$±2 cm$^{-1}$, 1575 cm$^{-1}$±2 cm$^{-1}$, 1614 cm$^{-1}$±2 cm$^{-1}$, 1649 cm$^{-1}$±2 cm$^{-1}$, and 1725 cm$^{-1}$±2 cm$^{-1}$.

Main absorption peaks are recognized at 1575 cm$^{-1}$±2 cm$^{-1}$, 1614 cm$^{-1}$±2 cm$^{-1}$, and 1649 cm$^{-1}$±2 cm$^{-1}$.

Main absorption peaks are recognized at 1614 cm$^{-1}$±2 cm$^{-1}$, and 1649 cm$^{-1}$±2 cm$^{-1}$.

Example 8

Synthesis of Anhydrous Crystal Form II of Compound Represented by Formula (I)

An anhydrous crystal Form I (about 10 mg) of the compound represented by Formula (I) was weighed in a vial, and 200 μL of CHCl$_3$ was added thereto. The mixture was stirred with a magnetic stirrer at 400 rpm at 25° C. (overnight operation). After 7 days, the mixture was filtered, and the obtained powder was confirmed by powder X-ray diffraction measurement.

The powder X-ray diffraction pattern of the anhydrous crystal Form II of the compound represented by Formula (I) are shown in FIG. 12 (Method 3).

In the powder X-ray diffraction spectrum, peaks are recognized at diffraction angles (2θ) of 8.5°±0.2°, 12.1°±0.2°, 16.4°±0.2°, 17.1°±0.2°, 18.1°±0.2°, 18.5°±0.2°, 20.3°±0.2°, 23.0°±0.2°, and 24.7°±0.2°.

In the powder X-ray diffraction spectrum, peaks are recognized at diffraction angles (2θ) of 8.5°±0.2°, 12.1°±0.2°, 16.4°±0.2°, 17.1°±0.2°, and 18.1°±0.2°.

Example 9

Flowability Test (Compressibility Index and Hausner Ratio)

Measurement Method

1) About 10 g of a sample was gently put into a 50 mL measuring cylinder, and the sample amount was measured.

2) The upper surface of the powder layer was carefully leveled without compaction, and the loose bulk volume ($V_0$) was read.

3) The measuring cylinder was mounted on a support stand of a powder tester (PT-X type, Hosokawa Micron Corporation).

4) The powder sample was tapped 10 times, 500 times, 1250 times, 2500 times and the corresponding bulk volumes ($V_{10}$, $V_{500}$, $V_{1250}$, $V_{2500}$) were read.

5) The process was ended when the volume difference was equal to or less than the minimum scale (0.5 mL), and the final bulk volume was defined as the final tap volume ($V_f$).

6) The steps 1) to 5) were repeated three times and measured, and the average values were adopted for calculation of the Compressibility index and the Hausner ratio.

Compressibility Index and Hausner Ratio Calculation Method

Compressibility index=$(V_0-V_f)/V_0\times100$

Hausner ratio=$V_0/V_f$

Results

The results are shown in Table 15.

TABLE 15

| Specimen | Anhydrous crystal Form I of compound represented by Formula (I) | Ethyl acetate/hexane solvate crystal of compound represented by Formula (I) | Dihydrate crystal of compound represented by Formula (I) |
|---|---|---|---|
| $V_0$ (mL) | 19.0 | 36.8 | 30.7 |
| $V_f$ (mL) | 14.2 | 23.3 | 19.7 |
| Compressibility index (%) | 25.4 | 36.7 | 35.9 |
| Hausner ratio | 1.3 | 1.6 | 1.6 |

As is apparent from Table 15, the anhydrous crystal Form I of the compound represented by Formula (I) was found to have the lowest Compressibility index (%) and better flowability as compared with the other two crystal forms (Reference: PMDA material; Flowability of powder; Compression and Hausner ratio measurements, excerpted in Table 16).

TABLE 16

| Compressibility index (%) | Flow character | Hausner ratio |
|---|---|---|
| ≤10 | Excellent | 1.00-1.11 |
| 11-15 | Good | 1.12-1.18 |
| 16-20 | Fair | 1.19-1.25 |
| 21-25 | Passable | 1.26-1.34 |
| 26-31 | poor | 1.35-1.45 |
| 32-37 | Very Poor | 1.46-1.59 |
| >38 | Very, very poor | >1.60 |

In general, it is known that stable production can be performed when the fluidity of a pharmaceutical powder is high in a pharmaceutical solid formulation process. The low fluidity of pharmaceutical powders can cause a bridge phenomenon in a hopper in a powder processing apparatus, for example, a tablet pressing machine, and an increase in tablet weight deviation. In order to produce a stable pharmaceutical powder, a crystalline form having high fluidity is required, and the anhydrous crystal Form I of the compound represented by Formula (I) was found to be a particularly preferable crystalline form in a pharmaceutical formulation process.

Example 10

Amount of Residual Solvent Listed in the ICH Q3C Guideline

Hexane is a solvent (class 2) whose residual amount in the active pharmaceutical ingredient should be regulated, and ethyl acetate is a low-toxicity solvent (class 3). Therefore, it is necessary to adjust the residual amount of hexane in the active pharmaceutical ingredient to a specified value or less. Table 17 below shows solvents of class 2 listed in the ICH Q3C guideline.

TABLE 17

| Solvent | PDE (mg/day) | Concentration limit value (ppm) |
|---|---|---|
| Acetonitrile | 4.1 | 410 |
| Chlorobenzene | 3.6 | 360 |
| Chloroform | 0.6 | 60 |
| Cyclohexane | 38.8 | 3880 |
| 1,2-dichloroethene | 18.7 | 1870 |
| Dichloromethane | 6.0 | 600 |
| 1,2-dimethoxyethane | 1.0 | 100 |
| N,N-dimethylacetamide | 10.9 | 1090 |
| N,N-dimethylformamide | 8.8 | 880 |
| 1,4-dioxane | 3.8 | 380 |
| 2-ethoxyethanol | 1.6 | 160 |
| Ethylene glycol | 6.2 | 620 |
| Formamide | 2.2 | 220 |
| Hexane | 2.9 | 290 |
| Methanol | 30.0 | 3000 |
| 2-methoxyethanol | 0.5 | 50 |
| Methylbutyl ketone | 0.5 | 50 |
| Methylcyclohexane | 11.8 | 1180 |
| N-methylpyrrolidone | 48.4 | 4840 |
| Nitromethane | 0.5 | 50 |
| Pyridine | 2.0 | 200 |
| Sulfolane | 1.6 | 160 |
| Tetralin | 1.0 | 100 |
| Toluene | 8.9 | 890 |
| 1,1,2-trichloroethene | 0.8 | 80 |
| Xylene | 21.7 | 2170 |

Permitted Daily Exposure (PDE) of hexane is 2.9 mg/day. When the ethyl acetate/hexane solvate crystal of the compound represented by Formula (I) is used as an active pharmaceutical ingredient, the PDE of hexane may be equal to or more than the regulation value depending on the dose.

On the other hand, the anhydrous crystal Form I and the dihydrate crystal of the compound represented by Formula (I) did not contain hexane as a residual solvent, and was found to be excellent as a crystal form used for an active pharmaceutical ingredient.

Example 11

Solid Stability Test

Measurement Method 5 mg sample (n=4) was precisely weighed in 2 mL vial, capped, and stored at a predetermined temperature (sealed storage). Then, each sample was taken out after storage for a predetermined period, and stability (content) was evaluated.

Storage Conditions

80° C. hermetically sealed

Storage Period one week

Test Solution Preparation Conditions

Each vial was washed out into a 25 mL volumetric flask. Diluting medium: acetonitrile/water=1/1

HPLC Measurement Conditions

Method D

Results

The results are shown in Table 18.

TABLE 18

| | Conditions | Residual ratio (%) | Purity (%) | Retention time (min)/Peak area (%) of analogous substance | | | | | | | | | |
|---|---|---|---|---|---|---|---|---|---|---|---|---|---|
| | | | | 3 | 5.8 | 10.1 | 10.5 | 14 | 15.5 | 16.9 | 17.1 | 18.3 | 20.6 |
| Anhydrous crystal Form I of compound represented by Formula (I) | Initial | — | 99.76 | | | | | | 0.16 | | 0.05 | | 0.03 |
| | 80° C. 1W | 99.79 | 99.77 | | | | | | 0.16 | | 0.04 | | 0.03 |
| Ethyl acetate/hexane solvate crystal of compound represented by Formula (I) | Initial | — | 99.71 | 0.06 | 0.01 | | 0.15 | 0.04 | | 0.04 | | | |
| | 80° C. 1W | 99.03 | 99.71 | 0.06 | 0.01 | | 0.14 | 0.04 | | 0.03 | | | |
| Dihydrate crystal of compound represented by Formula (I) | Initial | — | 99.91 | | | | | | 0.09 | | | | |
| | 80° C. 1W | 99.13 | 99.86 | 0.05 | | | | | 0.09 | | | | |

In any of the crystal forms, the residual ratio was 99% or more, and it was found to be a stable crystal form. In the ethyl acetate/hexane solvate crystal of the compound represented by Formula (I), five types of analogous substances were generated. In the anhydrous crystal Form I of the compound represented by Formula (I), three types of analogous substances were generated, and in the dihydrate crystal of the compound represented by Formula (I), two types of analogous substances were generated. From the above, it was found that in the anhydrous crystal Form I and the dihydrate crystal of the compound represented by Formula (I), there are few types of analogous substance to be generated.

The following formulation examples are merely examples, and are not intended to limit the scope of the invention at all.

The compound of the invention can be administered as a pharmaceutical composition by any conventional route, in particular enterally, for example orally, for example in the form of a tablet or a capsule, or parenterally, for example in the form of an injectable or a suspension; topically, for example in the form of a lotion, gel, ointment or cream; or in a nasal or suppository form. A pharmaceutical composition containing the compound of the invention in a free form or in a form of a pharmaceutically acceptable salt together with at least one pharmaceutically acceptable carrier or diluent can be produced in a conventional manner by mixing, granulating or coating. For example, the oral composition can be a tablet, a granule, or a capsule containing an excipient, a disintegrant, a binder, a lubricant, or the like, as well as an active ingredient, or the like. The injectable composition may be a solution or a suspension, may be sterilized, or may contain a preservative, a stabilizer, a buffering agent, or the like.

INDUSTRIAL APPLICABILITY

The crystal of the compound represented by Formula (I) as the present invention is useful as an active pharmaceutical ingredient. The pharmaceutical composition containing the crystal of the compound represented by Formula (I) is very useful as a therapeutic agent or a prophylactic agent for chronic cough.

Further, the present invention is useful as a method for producing the compound represented by Formula (I).

The invention claimed is:

1. An anhydrous crystal Form I of a compound represented by Formula (I),

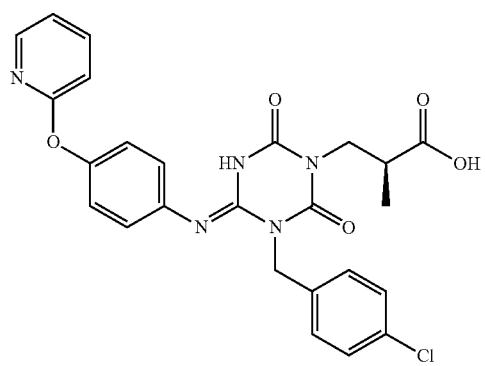

having, in a powder X-ray diffraction spectrum, characteristic peaks at:
diffraction angles (2θ) of 15.8°±0.2°, 19.4°±0.2°, 21.7°±0.2°, 23.9°±0.2°, and 25.4°±0.2°; or
diffraction angles (2θ) of 7.9°±0.2°, 9.3°±0.2°, 12.9°±0.2°, 15.8°±0.2°, and 19.4°±0.2°.

2. The anhydrous crystal Form I according to claim 1, having, in a powder X-ray diffraction spectrum, characteristic peaks at:
diffraction angles (2θ) of 12.6°±0.2°, 12.9°±0.2°, 15.8°±0.2°, 19.4°±0.2°, 21.7°±0.2°, 23.9°±0.2°, 25.4°±0.2°, 26.6°±0.2°, 27.8°±0.2°, and 32.8°±0.2°; or
differential angles (2θ) of 7.9°±0.2°, 9.3°±0.2°, 12.9°±0.2°, 15.8°±0.2°, 17.2°±0.2°, 19.4°±0.2°, 21.7°±0.2°, 23.9°±0.2°, 25.4°±0.2°, and 27.8°±0.2°.

3. The anhydrous crystal Form I according to claim 1, further having absorption peaks at 829 $cm^{-1}$±2 $cm^{-1}$, 989 $cm^{-1}$±2 $cm^{-1}$, 1013 $cm^{-1}$±2 $cm^{-1}$, 1128 $cm^{-1}$±2 $cm^{-1}$, and 1370 $cm^{-1}$±2 $cm^{-1}$ in Raman spectrum.

4. A dihydrate crystal of a compound represented by Formula (I),

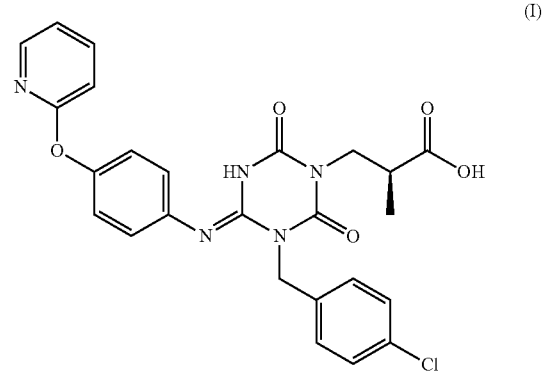 [SMILES: C[C@@H](Cn1c(=O)[nH]/c(=N\c2ccc(Oc3ccccn3)cc2)n(Cc2ccc(Cl)cc2)c1=O)C(=O)O]

having characteristic peaks at diffraction angles (2θ) of 5.7°±0.2°, 7.7°±0.2°, 11.8°±0.2°, 15.2°±0.2°, and 17.7°±0.2° in a powder X-ray diffraction spectrum.

5. The dihydrate crystal according to claim 4, having characteristic peaks at diffraction angles (2θ) of 5.7°±0.2°, 7.7°±0.2°, 11.8°±0.2°, 15.2°±0.2°, 17.7°±0.2°, 20.6°±0.2°, 20.8°±0.2°, 26.5°±0.2°, 27.1°±0.2°, and 29.1°±0.2° in a powder X-ray diffraction spectrum.

6. The dihydrate crystal according to claim 4, further having absorption peaks at 871 $cm^{-1}$±2 $cm^{-1}$, 996 $cm^{-1}$±2 $cm^{-1}$, 1114 $cm^{-1}$±2 $cm^{-1}$, 1234 $cm^{-1}$±2 $cm^{-1}$, 1340 $cm^{-1}$±2 $cm^{-1}$, and 1577 $cm^{-1}$±2 $cm^{-1}$ in Raman spectrum.

7. A pharmaceutical composition comprising the anhydrous crystal Form I according to claim 1.

8. A pharmaceutical composition comprising the dihydrate crystal according to claim 4.

* * * * *